(12) United States Patent
Yoko et al.

(10) Patent No.: US 11,141,290 B2
(45) Date of Patent: Oct. 12, 2021

(54) REVISION KNEE ARTHROPLASTY METHODS AND INSTRUMENTS

(71) Applicant: Zimmer, Inc., Warsaw, IN (US)

(72) Inventors: Tim Yoko, Granger, IN (US); Joseph C. Capek, Granger, IN (US); Amanda Szalkowski, Winona Lake, IN (US); Jeffery A. VanDiepenbos, New Paris, IN (US)

(73) Assignee: Zimmer, Inc., Warsaw, IN (US)

(\*) Notice: Subject to any disclaimer, the term of this patent is extended or adjusted under 35 U.S.C. 154(b) by 125 days.

(21) Appl. No.: 16/156,747

(22) Filed: Oct. 10, 2018

(65) Prior Publication Data

US 2019/0110907 A1 Apr. 18, 2019

Related U.S. Application Data

(60) Provisional application No. 62/572,210, filed on Oct. 13, 2017.

(51) Int. Cl.
*A61F 2/46* (2006.01)
*A61F 2/38* (2006.01)
(Continued)

(52) U.S. Cl.
CPC .......... *A61F 2/4684* (2013.01); *A61B 17/155* (2013.01); *A61B 17/157* (2013.01);
(Continued)

(58) Field of Classification Search
CPC ...... A61F 2/4684; A61F 2/389; A61F 2/3859; A61F 2/461; A61F 2/4603;
(Continued)

(56) References Cited

U.S. PATENT DOCUMENTS 5,282,861 A 2/1994 Kaplan
5,702,461 A 12/1997 Pappas et al.
(Continued)

FOREIGN PATENT DOCUMENTS

CN 101744675 6/2010
CN 104013456 9/2014
(Continued)

OTHER PUBLICATIONS

"International Application Serial No. PCT US2018 055218, International Search Report dated Jan. 30, 2019", 5 pgs.
(Continued)

*Primary Examiner* — Bruce E Snow
*Assistant Examiner* — Melissa A Hoban
(74) *Attorney, Agent, or Firm* — Schwegman Lundberg & Woessner, P.A.

(57) ABSTRACT

According to one example, a for revision knee arthroplasty is disclosed. According to this example, the method can include shaping a bone of a patient to create one or more recesses therein, selecting a stem provisional, disposing the stem provisional within the one or more recesses, and assembling in vivo the stem provisional with both a first provisional component configured to simulate a shape of one of a tibial tray implant or a femoral implant and a second provisional component configured to simulate a shape of at least one of a sleeve component, a cone component or a keel component of an implant.

12 Claims, 54 Drawing Sheets

(51) Int. Cl.
| | |
|---|---|
| *A61B 17/16* | (2006.01) |
| *A61B 17/17* | (2006.01) |
| *A61B 17/15* | (2006.01) |
| *A61F 2/30* | (2006.01) |
| *A61B 17/00* | (2006.01) |

(52) U.S. Cl.
CPC ........ *A61B 17/164* (2013.01); *A61B 17/1659* (2013.01); *A61B 17/1675* (2013.01); *A61B 17/1764* (2013.01); *A61F 2/389* (2013.01); *A61F 2/3859* (2013.01); *A61F 2/461* (2013.01); *A61B 17/1613* (2013.01); *A61B 2017/00477* (2013.01); *A61F 2/4603* (2013.01); *A61F 2002/3069* (2013.01); *A61F 2002/30405* (2013.01); *A61F 2002/30604* (2013.01); *A61F 2002/4681* (2013.01); *A61F 2002/4687* (2013.01)

(58) Field of Classification Search
CPC .... A61F 2002/30604; A61F 2002/4687; A61F 2002/4681; A61F 2002/30405; A61F 2002/3069; A61B 17/1675; A61B 17/157; A61B 17/164; A61B 17/155; A61B 17/1659; A61B 17/1764; A61B 17/1613; A61B 2017/0047
See application file for complete search history.

(56) References Cited

U.S. PATENT DOCUMENTS

| | | | |
|---|---|---|---|
| 6,171,342 | B1 | 1/2001 | O'Neil et al. |
| 6,902,583 | B2 | 6/2005 | Gerbec et al. |
| 6,911,100 | B1 | 6/2005 | Gibbs et al. |
| 7,291,174 | B2 | 11/2007 | German et al. |
| 7,799,085 | B2 | 9/2010 | Goodried et al. |
| 8,187,280 | B2 | 5/2012 | May et al. |
| 8,535,385 | B2 | 9/2013 | Hanssen et al. |
| 8,556,900 | B2 | 10/2013 | Yoko et al. |
| 8,721,733 | B2 | 5/2014 | Bonitati |
| 8,979,847 | B2 | 3/2015 | Belcher et al. |
| 8,998,996 | B2 | 4/2015 | James et al. |
| 9,603,649 | B2 | 3/2017 | Matyas et al. |
| 10,182,830 | B2 | 1/2019 | Amanatullah |
| 2004/0049286 | A1 | 3/2004 | German et al. |
| 2005/0124998 | A1 | 6/2005 | Coon et al. |
| 2009/0306787 | A1 | 12/2009 | Crabtree et al. |
| 2012/0143204 | A1 | 6/2012 | Blaylock et al. |
| 2012/0245700 | A1 | 9/2012 | Sidebotham |
| 2012/0310246 | A1 | 12/2012 | Belcher et al. |
| 2013/0006370 | A1 | 1/2013 | Wogoman et al. |
| 2013/0172892 | A1* | 7/2013 | Servidio ............ A61B 17/1668 606/80 |
| 2013/0304221 | A1 | 11/2013 | Blaylock et al. |
| 2013/0325019 | A1* | 12/2013 | Thomas ............. A61B 17/1735 606/88 |
| 2014/0228846 | A1 | 8/2014 | Roby et al. |
| 2014/0277528 | A1 | 9/2014 | Mines et al. |
| 2014/0277540 | A1 | 9/2014 | Leszko et al. |
| 2014/0277546 | A1 | 9/2014 | Major |
| 2015/0216667 | A1 | 8/2015 | Monaghan |
| 2016/0081758 | A1 | 3/2016 | Bonutti |
| 2016/0367381 | A1 | 12/2016 | Chaney et al. |
| 2017/0000503 | A1 | 1/2017 | Keefer et al. |
| 2017/0172748 | A1 | 6/2017 | Angibaud et al. |
| 2019/0038417 | A1 | 2/2019 | Yoko et al. |
| 2019/0105159 | A1 | 4/2019 | Dees et al. |
| 2019/0110906 | A1 | 4/2019 | Yoko et al. |
| 2020/0289290 | A1 | 9/2020 | Yoko et al. |

FOREIGN PATENT DOCUMENTS

| | | |
|---|---|---|
| CN | 104042303 | 9/2014 |
| CN | 104042368 | 9/2014 |
| CN | 104042369 | 9/2014 |
| CN | 111212616 A | 5/2020 |
| JP | 2014176658 | 9/2014 |
| JP | 2020536670 A | 12/2020 |
| WO | 2014063084 | 4/2014 |
| WO | 2019075066 | 4/2019 |
| WO | 2019075078 | 4/2019 |

OTHER PUBLICATIONS

"International Application Serial No. PCT US2018 055218, Written Opinion dated Jan. 30, 2019", 5 pgs.

"U.S. Appl. No. 16/047,463, Response filed May 21, 2020 to Non Final Office Action dated Feb. 21, 2020", 18 pgs.

"International Application Serial No. PCT US2018 055232, Invitation to Pay Additional Fees and Partial Search Report dated Jan. 24, 2019", 14 pgs.

"International Application Serial No. PCT US2018 055232, International Search Report dated Mar. 19, 2019", 8 pgs.

"International Application Serial No. PCT US2018 055232, Written opinion dated Mar. 19, 2019", 12 pgs.

"U.S. Appl. No. 16/047,463, Non Final Office Action dated Feb. 21, 2020", 18 pages.

"Smith and Nephew", Legion Cones Surgical Technique V1, (Jan. 2017), 36 pages.

"U.S. Appl. No. 16/652,896, Preliminary Amendment Filed Apr. 1, 2020", 8 pages.

"International Application Serial No. PCT US2018 055232, International Preliminary Report on Patentability dated Apr. 23, 2020", 12 pages.

"International Application Serial No. PCT US2018 055218, International Preliminary Report on Patentability dated Apr. 23, 2020", 7 pages.

"U.S. Appl. No. 16/047,463, Final Office Action dated Sep. 4, 2020", 15 pgs.

"U.S. Appl. No. 16/047,463, Notice of Allowance dated Dec. 14, 2020", 5 pgs.

"U.S. Appl. No. 16/047,463, Response filed Oct. 28, 2020 to Final Office Action dated Sep. 4, 2020", 12 pgs.

"U.S. Appl. No. 16/156,728, Non Final Office Action dated Dec. 23, 2020", 22 pgs.

"U.S. Appl. No. 16/156,728, Response filed Oct. 12, 2020 to Restriction Requirement dated Aug. 21, 2020", 9 pgs.

"U.S. Appl. No. 16/156,728, Restriction Requirement dated Aug. 21, 2020", 7 pgs.

"Australian Application Serial No. 2018347354, First Examination Report dated Dec. 14, 2020", 6 pgs.

"European Application Serial No. 18796230.3, Response to Communication pursuant to Rules 161(1) and 162 EPC filed Nov. 30, 2020", 22 pgs.

"European Application Serial No. 18797274.0, Response to Communication pursuant to Rules 161(1) and 162 EPC filed Dec. 9, 2020", 18 pgs.

"Canadian Application Serial No. 3,078,736, Office Action dated Apr. 29, 2021", 5 pages.

"Japanese Application Serial No. 2020-520521, Notification of Reasons for Refusal dated May 25, 2021", with English translation, 9 pages.

"Chinese Application Serial No. 201880066636.2, Office Action dated May 31, 2021", with English translation, 14 pages.

"U.S. Appl. No. 16/156,728, Non Final Office Action dated Jul. 7, 2021", 19 pages.

\* cited by examiner

REVISION KNEE ARTHROPLASTY METHODS AND INSTRUMENTS

CLAIM OF PRIORITY

This application claims the benefit of U.S. Provisional Patent Application Ser. No. 62/572,210, filed on Oct. 13, 2017, the benefit of priority of which is claimed hereby, and which is incorporated by reference herein in its entirety.

FIELD

The present subject matter relates to orthopedic instruments, systems methods and techniques. More particularly, the present application relates to instruments, systems, methods and techniques that can be used in revision knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides and other instruments are used to guide the removal of the articular surfaces that are to be replaced. Prostheses are used to replicate the articular surfaces. Knee prostheses can include a femoral component implanted on the distal end of the femur, which articulates with a tibial beating component and a tibial component implanted on the proximal end of a tibia to replicate the function of a healthy natural knee. Various types of arthroplasties are known including a total knee arthroplasty, where all of the articulating compartments of the joint are repaired with prosthetic components and a revision knee arthroplasty where a physician removes a previously implanted knee prosthesis and replaces it with a new prosthesis.

OVERVIEW

This disclosure pertains generally to surgical instruments, systems, methods and techniques for a knee arthroplasty such as a revision knee arthroplasty. The present inventors have recognized, among other things, provisional components, instrument designs, systems and processes that simplify, reduce the cost and/or improve the efficacy of a knee surgery. For example, the present application discloses provisional systems that can be coupled together and positionally adjusted in vivo to better match the anatomy of the patient. More particularly, a stem provisional assembly is disclosed that can be configured to be moveable in vivo to position the stem provisional assembly within a bone recess.

To reduce cost and the number of components, the stem provisional assembly can comprise a system that can include a plurality of adaptors and a plurality of stem extensions. Each of the plurality of adaptors can have a longitudinal axis extending between a proximal end and a distal end. The plurality of adaptors include at least a first adaptor with no offset of the longitudinal axis and at least a second adaptor with some amount of offset of the longitudinal axis. Each of the plurality of stem extensions can be configured to interchangeably couple with the plurality of adaptors. The plurality of stem extensions each can have a different longitudinal extent between a proximal end and a distal end.

In a further aspect that can save time, reduce costs and simplify the procedure, systems of provisional components are disclosed that can be assembled in vivo and then removed. More particularly, after being assembled in vivo the assembly can then be removed from the patient with the positions of each component maintained relative to one another. This can allow permanent implants to more easily and timely be created based upon the provisional assembly as the positions of the individual provisional components need not be documented or otherwise indicated in great detail. Rather, the entire provisional assembly with relative desired positions for each part relative to the others can be maintained for easy reference. These and other aspects of the present application that will be discussed in further detailed subsequently. It will be evident to one of ordinary skill in the art that the present application includes various other inventive concepts that can simplify, reduce cost and improve the efficacy of the knee surgery.

To further illustrate the apparatuses, systems and methods disclosed herein, the following non-limiting examples are provided:

In Example 1, a provisional system for a knee arthroplasty is disclosed. The system can include a first provisional component having a proximal surface and a distal surface opposing the proximal surface, one of the distal surface and the proximal surface configured to be disposed on a resected surface of a bone. The system can include a second provisional component configured to be disposed in a first recess beneath the resected surface of the bone, wherein the second provisional component is configured to simulate a shape of at least one of a sleeve component, a cone component or a keel component of an implant. The system can include a stem provisional assembly configured to be disposed in a second recess, the stem provisional assembly configured to be engageable in vivo to position the first provisional component on the resected surface of the bone. The system can include a fastener configured to couple the first provisional component, the second provisional component and the stem provisional assembly together as an assembly, wherein the fastener includes a passage to allow access to the stem provisional assembly from adjacent the first provisional component.

In Example 2, the system of Example 1, can optionally further include a handle configured to temporarily engage the second provisional component to the stem provisional assembly, wherein when temporarily engaged with the handle the second provisional component and the stem provisional assembly are insertable into the first recess and the second recess of the bone, respectively.

In Example 3, the system of any one or any combination of Examples 1-2, can optionally further include a driver or plurality of drivers configured to at least one of: engage the fastener to thread the fastener into a threaded recess of the stem provisional assembly; and pass through the passage in the fastener to engage the stem provisional assembly, wherein engagement between the driver and the stem provisional assembly rotates the stem provisional assembly in vivo and positions the first provisional component on the resected surface.

In Example 4, the system of any one or any combination of Examples 1-3, wherein the first provisional component can optionally include a first taper and a second taper, the second provisional component includes a third taper and a fourth taper and the stem provisional assembly all includes a fifth taper, and wherein the first taper is configured to engage with the third taper, the second taper is configured to engage with the fifth taper, and the fourth taper is configured to engage with the fifth taper when the fastener couples the first provisional component, the second provisional component and the stem provisional assembly together as the assembly.

In Example 5, the system of Example 4, wherein the first taper and the fifth taper can optionally comprise external tapers and the second taper, the third taper and the fourth taper comprise internal tapers.

In Example 6, the system of any one or any combination of Examples 1-5, wherein the fastener, the first provisional component, the second provisional component and the stem provisional assembly can optionally be removable from the bone together as the assembly with the positions of each component maintained relative to one another.

In Example 7, the system of any one or any combination of Examples 1-6, wherein the stem provisional assembly can optionally be a system comprising: a plurality of adaptors each having a longitudinal axis extending between a proximal end and a distal end, wherein the plurality of adaptors include at least a first adaptor with no offset of the longitudinal axis and at least a second adaptor with some amount of offset of the longitudinal axis; a plurality of stem extensions each configured to interchangeably couple with the plurality of adaptors, wherein the plurality of stem extensions each have a different longitudinal extent between a proximal end and a distal end.

In Example 8, the system of Example 7, wherein the at least a second adaptor can optionally comprise two adaptors one adaptor with a first amount of offset and another adaptor with a second amount of offset that differs from the first amount of offset.

In Example 9, the system of any one or any combination of Examples 1-6, wherein the stem provisional assembly can optionally be one a sub-system comprising a plurality of monolithic single piece assemblies, and wherein each of the plurality of monolithic single piece assemblies includes an adaptor part and a stem extension part.

In Example 10, the system of any one or any combination of Examples 1-9, wherein the first provisional component can optionally comprise a femoral component having an elongated slot configured to receive a pin therein, wherein the elongated slot is configured to allow proximal-distal movement of the femoral component relative to the pin.

In Example 11, the system of any one or any combination of Examples 1-10, wherein second provisional component can optionally comprise a broach configured to remove bone to create the first recess.

In Example 12, a tibial or femoral provisional system for a knee arthroplasty is disclosed. The system can include a first provisional component having a proximal surface and a distal surface opposing the proximal surface, the one of the proximal or distal surface configured to be disposed on a resected surface of a bone comprising a tibia or a femur. The system can include a second provisional component configured to be disposed in a first recess beneath the resected surface, wherein the second provisional component is a provisional to simulate a shape of at least one of a sleeve component, a cone component or a keel component of an implant. The system can include a stem provisional assembly configured to be disposed in a second recess of the tibia or femur, the stem provisional assembly configured to be engageable in vivo to reposition the first provisional component on the resected surface. The system can include a fastener configured to couple the first provisional component, the second provisional component and the stem provisional assembly together as an assembly.

In Example 13, the system of Example 12, wherein the fastener can optionally include a passage to allow access to engage the stem provisional assembly.

In Example 14, the system of Example 12, optionally can further comprise a driver or plurality of drivers configured to at least one of: engage the fastener to thread the fastener into a threaded recess of the stem provisional assembly; and pass through passage in the fastener to engage the stem provisional assembly, wherein engagement between the driver and the stem provisional assembly rotates the stem provisional assembly in vivo.

In Example 15, the system of any one or any combination of Examples 12-14, wherein the fastener, the first provisional component, the second provisional component and the stem provisional assembly can optionally be removable from the tibia together as the assembly with the positions of each maintained relative to one another.

In Example 16, the system of any one or any combination of Examples 12-15, wherein the stem provisional assembly can optionally comprise a system that includes: a plurality of adaptors each having a longitudinal axis extending between a proximal end and a distal end, wherein the plurality of adaptors include at least a first adaptor with no offset of the longitudinal axis and at least a second adaptor with some amount of offset of the longitudinal axis; and a plurality of stem extensions each configured to interchangeably couple with the plurality of adaptors, wherein the plurality of stem extensions each have a different longitudinal extent between a proximal end and a distal end.

In Example 17, the system of any one or any combination of Examples 12-15, wherein the stem provisional assembly can optionally be one a sub-system comprising a plurality of monolithic single piece assemblies, and wherein each of the plurality of monolithic single piece assemblies includes an adaptor part and a stem extension part.

In Example 18, a method for revision knee arthroplasty can optionally comprise: shaping a bone of a patient to create one or more recesses therein; selecting a stem provisional; disposing the stem provisional within the one or more recesses; and assembling in vivo the stem provisional with both a first provisional component configured to simulate a shape of one of a tibial tray implant or a femoral implant and a second provisional component configured to simulate a shape of at least one of a sleeve component, a cone component or a keel component of an implant.

In Example 19, the method of Example 18, can optionally further comprise: temporarily coupling the second provisional component and the stem provisional assembly together with a handle configured to insert over a post extension; and inserting the stem provisional assembly and the second provisional component together into the one or more recesses.

In Example 20, the method of any one or any combination of Examples 18-19, can further optionally comprise: identifying an axis of the bone; and determining if an offset construct for the stem provisional assembly is desirable.

In Example 21, the method of any one or any combination of Examples 18-20, wherein selecting the stem provisional can optionally comprise: selecting a monolithic stem provisional having an adaptor part and an stem extension part; or selecting the adaptor from a plurality of adaptors each of the plurality of adaptors having a longitudinal axis extending between a proximal end and a distal end, wherein the plurality of adaptors include at least a first adaptor with no offset of the longitudinal axis and at least a second adaptor with some amount of offset of the longitudinal axis; and selecting the stem extension from a plurality of stem extensions each configured to couple with the plurality of adaptors, wherein the plurality of stem extensions each have a different longitudinal extent between a proximal end and a distal end.

In Example 22, the method of any one or any combination of Examples 18-21, wherein the step of assembling in vivo the stem provisional assembly with both the first provisional component configured to simulate the shape of one of the tibial tray implant or the femoral implant and the second provisional component configured to simulate the shape of at least one of the sleeve component or the keel component of the implant can optionally include one or both of: engaging a fastener to thread the fastener into a threaded recess of the stem provisional assembly; and passing a tool through a passage in the fastener to engage the stem provisional assembly distal of the threaded recess.

In Example 23, the method of any one or any combination of Examples 18-22, can further optionally comprise engaging the stem provisional assembly in vivo to position the first provisional component in a desired location on a resected surface of the bone.

In Example 24, the method of any one or any combination of Examples 18-23, can further optionally comprise removing at least the first provisional component, the second provisional component and the stem provisional assembly, together from the bone and the one or more recesses with the positions of each maintained relative to one another.

In Example 25, the method of Example 24, optionally further including constructing an implant assembly based upon the positions of the first provisional component, the second provisional component and the stem provisional assembly.

In Example 26, the system of any one or any combination of Examples 1-17, can further optionally comprise a multi-purpose handle configured to couple with one or more of the second provisional component and an offset broach, wherein the multi-purpose handle has a cannulated shaft and includes a slap hammer that is configured to be moveable along the shaft of the handle and fixable thereto.

In Example 27, the system of Example 26, wherein the offset broach can optionally have cutting surface along only a first side thereof and a second side thereof opposing the first side is configured to receive and interface with a reamer, wherein the offset broach is configured to offset the first recess relative to the second recess.

In Example 28, the method of any one or any combination of Examples 18-25, can further optionally comprise: coupling a multi-purpose handle to one or more of the second provisional component and an offset broach; and extracting the offset broach from the bone using movement of a slap hammer of the multi-purpose handle.

In Example 29, the method of Example 28, wherein the offset broach has cutting surface along only a first side thereof and a second side thereof opposing the first side is configured to receive and interface with a reamer, wherein the offset broach is configured to offset a first portion of the one or more recesses relative to a second portion of the one or more recesses.

In Example 30, the system of any one or any combination of Examples 1-17 and 26-27, can optionally further comprise a drill guide configured to be mountable to the stem provisional assembly and configured to pre-drill out the bone prior to broaching for the sleeve component or the cone component.

In Example 31, the method of any one or any combination of Examples 18-25 and 28-29, wherein shaping the bone of the patient to create one or more recesses therein can optionally comprise: coupling a drill guide to the stem provisional assembly, the drill guide having a plurality of apertures configured to receive and guide a drill into the bone; and broaching the bone.

In Example 32, the system of any one or any combination of Examples 1-17, 26-27 and 30, can further optionally comprise a tilt reamer having distal nose portion and a cutting portion with a back angled taper having a decreasing diameter as measured distal-to-proximal along a longitudinal axis of the tilt reamer.

In Example 33, the method of any one or any combination of Examples 18-25, 28-29 and 31, wherein shaping the bone of the patient to create one or more recesses therein can optionally comprise: performing a reaming of the bone with a tilt reamer having distal nose portion and a cutting portion with a back angled taper having a decreasing diameter as measured distal-to-proximal along a longitudinal axis of the tilt reamer.

In Example 34, the system of any one or any combination of Examples 1-17, 26-27, 30 and 32, can optionally further comprise a tibial cut guide assembly, configured to guide a resection that forms the resected surface, wherein the tibial cut guide assembly has a boom arm and a body coupled to the boom arm by a collar, and wherein the collar includes an opening configured to allow for removal of the boom arm from the collar without a position of the body being changed relative to the bone.

The method of any one or any combination of Examples 18-25, 28-29, 31 and 33, can further optionally comprise resecting the bone with a tibial cut guide assembly to form a resected surface, wherein resecting includes: positioning a body of the tibial cut guide assembly adjacent a proximal portion of a tibia with a boom arm; pinning the body to the proximal portion; and removing the boom arm without removing the body from a position pinned to the proximal portion.

In Example 36, the system of any one or any combination of Examples 1-17, 26-27, 30, 32 and 34, can further optionally comprise a stem implant configured with one or more slots along a distal portion thereof to allow for flexing of the stem implant in any direction.

In Example 37, an assembly can optionally comprise: a fastener having a thread portion and a head portion; and a component with a bore, the bore can optionally comprise: a corresponding thread portion configured to couple with the thread portion of the fastener, a pocket portion within the bore adjacent the corresponding thread portion, wherein the pocket is configured to be receive the fastener when the thread portion of the fastener is decoupled from the corresponding thread portion, and a restriction disposed adjacent the pocket portion, wherein the restriction is configured with a diameter substantially equal to or smaller than that of the head portion so as to retain the fastener within the pocket when the thread portion of the fastener is decoupled from the corresponding thread portion.

In Example 38, the assembly of Example 37, wherein the pocket portion can optionally have a diameter greater than that of the head portion.

In Example 39, the assembly of any one or any combination of Examples 37 and 38, wherein one or more of the restriction and the head portion of the fastener can optionally have a chamfer surface configured to act as a ramp to facilitate insertion of the head portion past the restriction.

In Example 40, the apparatuses, systems and methods of any one or any combination of Examples 1 to 39 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates provisional prostheses, tools, systems, and methods.

As discussed above, the provisional prostheses, instruments, systems, and methods can simplify, reduce the cost and/or improve the efficacy of a knee surgery. It is important to note that all the instruments, components, systems, methods and techniques described herein can be used with and are equally applicable to the femur as well as the tibia.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior". The terms "medial" and "lateral" should be given their generally understood anatomical interpretations. Thus, "medial" refers to the opposite direction of "lateral".

Figure 1:
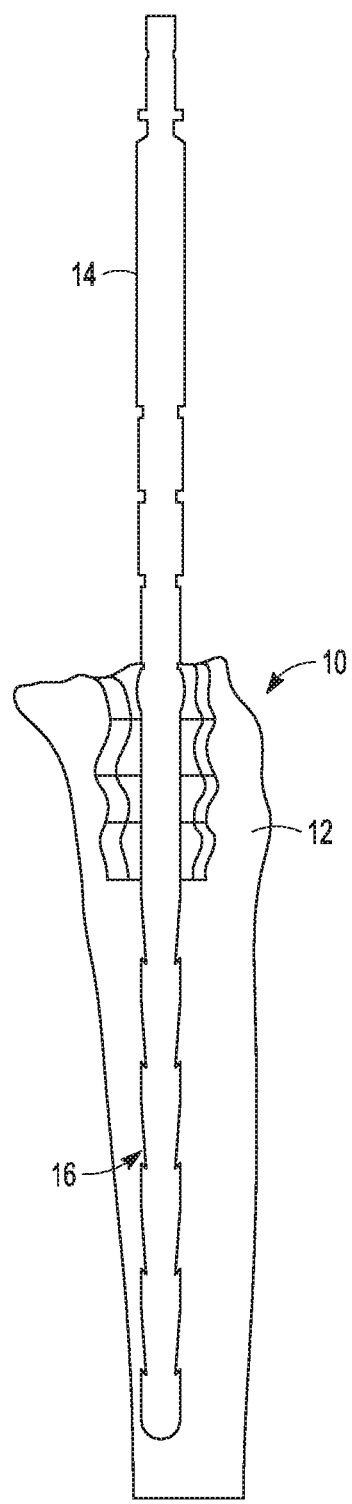
FIG. 1 shows a cross-sectional view of a reamer inserted in a bone such as a tibia in accordance with an example of the present application.

FIG. 1 illustrates a cross-sectional view of a tibia 10 and a reamer 14. Only a proximal portion 12 of the tibia 10 is shown in FIG. 1. The reamer 14 has been inserted into the tibia 10 and can be configured with flutes or sharp edged features to remove bone and create a recess 16 therein. This recess 16 can in some cases be formed at least partially by existing anatomy of the patient such as an intramedullary canal, for example. In some cases, it can be desirable to create the recess 16 and/or insert the reamer to track the intramedullary canal so as to align the provisional and implant components relative to the mechanical and anatomic axes of the tibia 10. The tibia 10 may be the subject of a revision knee arthroplasty. Thus, prior to the reaming shown in FIG. 1, the tibia 10 may have had a tibial implant component that was removed as part of the revision knee arthroplasty. As will be discussed and shown in further detail subsequently, the proximal portion 12 may have diseased or otherwise undesirable bone that may need to be removed as part of the revision knee arthroplasty prior to a new implant being disposed on the proximal portion 12.

Figure 2:
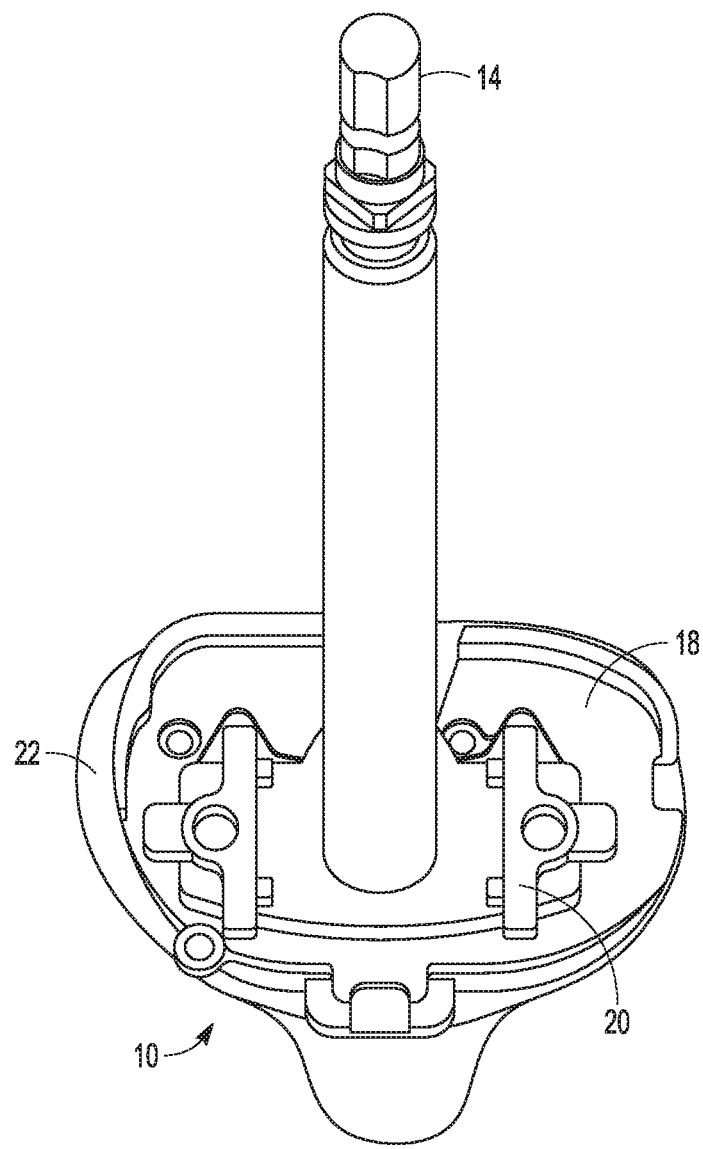
FIG. 2 shows a perspective view of the reamer with a tibial sizer and a coupler in accordance with an example of the present application.

FIG. 2 shows a perspective view of the reamer 14, a tibial sizer 18 and a coupler 20. The coupler 20 can engage the tibial sizer 18 and can be configured to receive the reamer 14. Thus, the tibial sizer 18 can be coupled to the reamer 14 via the coupler 20. The embodiment of FIG. 2 shows the coupler 20 can be configured to provide no offset for the tibial sizer 18 relative to the reamer 14. The reamer 14 via the coupler 20 can position the tibial sizer 18 on a proximal surface 22 of the tibia 10. An appropriately sized tibial sizer 18 can be selected that results in a desired amount of coverage of the proximal surface 22 with little to no overhang. An assembly with no offset for the tibial sizer 18 may be desired if the tibial sizer 18 is positioned satisfactorily atop the proximal surface 22 and is in substantial alignment with the mechanical and anatomic axes of the tibia 10 as indicated by the reamer 14. Once an appropriate size and position are determined any desired marking of the proximal tibia can occur and the tibial sizer 18 and coupler 20 can be removed leaving the reamer 14 in the tibia 10.

Figure 3:
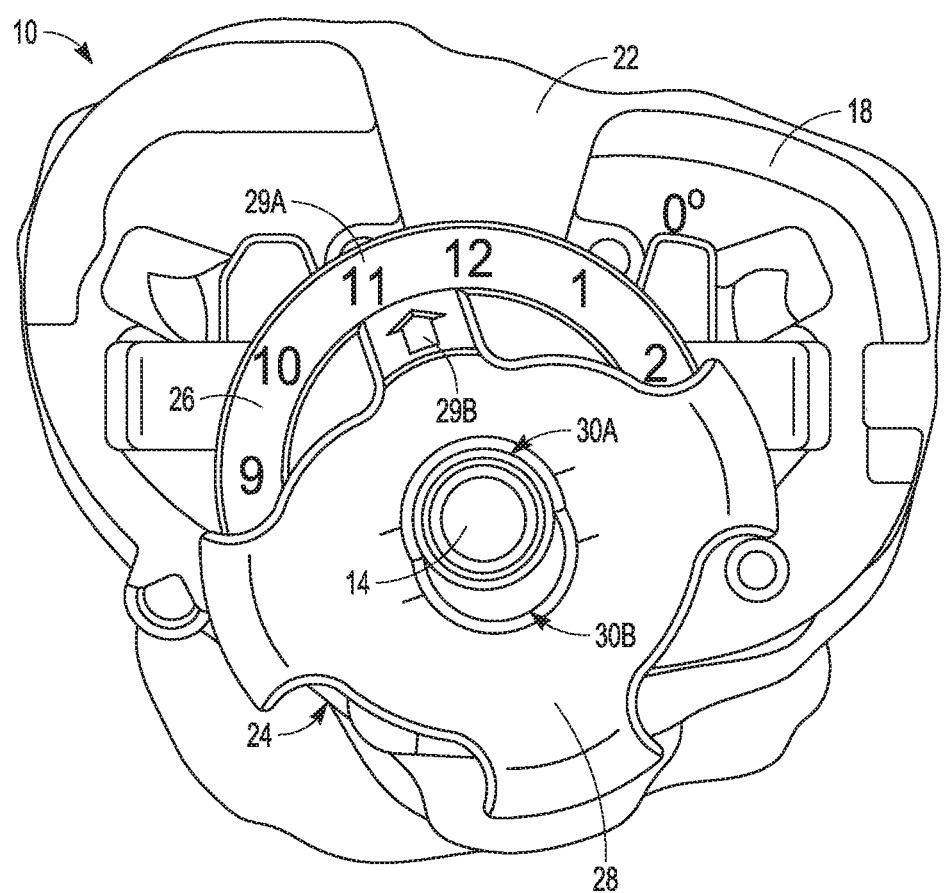
FIG. 3 shows an elevated plane view of the reamer and the tibial sizer of FIG. 2 but with an offset coupler assembly used to position the tibial sizer relative to the reamer in accordance with an example of the present application.
Figure 3A:
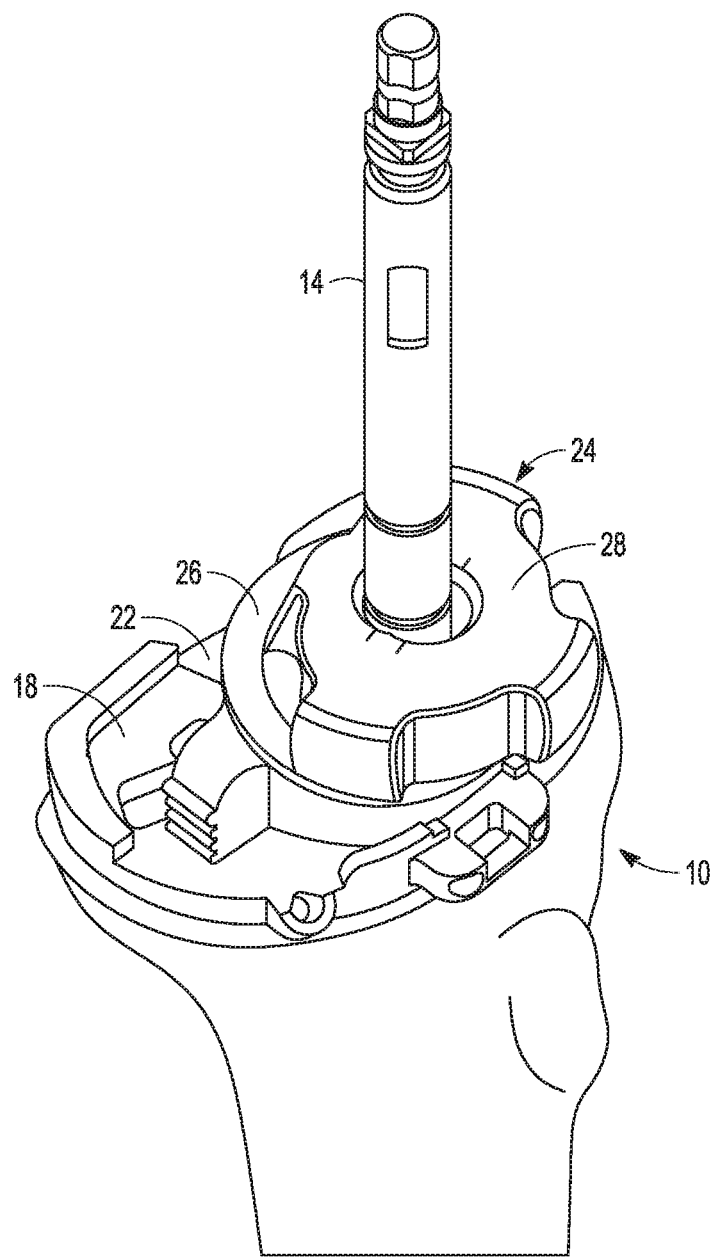
FIG. 3A shows an perspective view of the reamer, the tibial sizer and the offset coupler assembly of FIG. 3 in accordance with an example of the present application.

FIGS. 3 and 3A show an alternative assembly of the reamer 14, the tibial sizer 18 and an offset coupler 24. The offset coupler 24 can include a distal portion 26 and a proximal portion 28.

The distal portion 26 can engage the tibial sizer 18 in a similar manner to the coupler 20 of FIG. 2. However, the proximal portion 28 can be configured as a dial so as to be moveable relative to the distal portion 26. As the position of the reamer 14 is fixed relative to the tibia 10 while the tibial sizer 18 is not fixed relative to the tibia 10, movement of the proximal portion 28 relative to the distal portion 26 can move a position of the tibial sizer 18 on the proximal surface 22 of the tibia 10. The proximal portion 28 can be rotated relative to the distal portion 26 until a desired position for the tibial sizer 18 is achieved. Indicia 29A, 29B can be on the distal portion 26 and the proximal portion 28, respectively. The indicia 29A, 29B can be used to indicate the position of the tibial sizer 18 relative to the reamer 14.

As is best shown in the example of FIG. 3, the proximal portion 28 can have a plurality of through holes 30A, 30B configured to receive the reamer 14. The plurality of through holes 30A, 30B can include a first through hole 30A and a second through hole 30B. More particularly, the plurality of through holes 30A and 30B can have parallel longitudinal axes and can communicate with one another. The through holes 30A and 30B can be configured to provide varying degrees of offset for the offset coupler 24 and the tibial sizer 18 with respect to the reamer 14. For example, the first through hole 30A can provide the offset coupler 24 and the tibial sizer 18 with 3 mm of offset with respect to the reamer 14 and the second through hole 30B can provide the offset coupler 24 and the tibial sizer 18 with 6 mm of offset with respect to the reamer 14.

Figure 4:
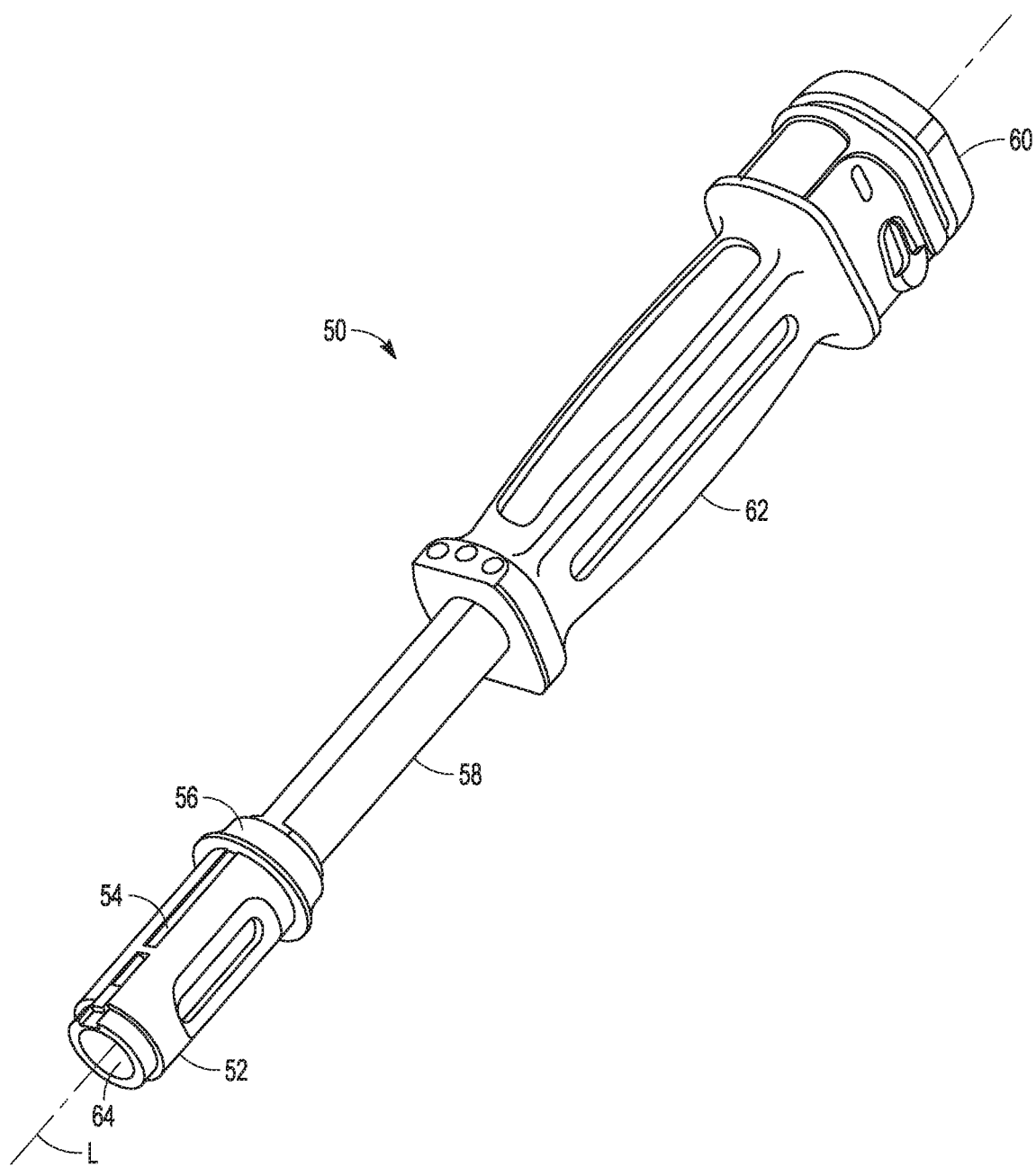
FIG. 4 shows a perspective view of a multi-purpose handle in accordance with an example of the present application.

FIGS. 4-6B show a multi-purpose handle 50. The handle 50 can also be utilized in conjunction with the apparatuses, systems and methods of FIGS. 10A-11D. As shown in FIG. 4, the tool 50 can include a distal tip 52, a pin 54, a collar 56, a shaft 58, a proximal end portion 60 and a slap hammer 62.

The handle 50 can extend along a longitudinal axis L from the distal tip 52 to the proximal end portion 60. The distal tip 52 can connect to the shaft 58. The shaft 58 can connect to the proximal end portion 60. Indeed, the shaft 58 can form the proximal end portion 60. The pin 54 can be disposed along the shaft 58 and can connect to the collar 56. The collar 56 can be disposed about the shaft 58 and can be moveable relative thereto proximal-distal (along longitudinal axis L). The slap hammer 62 can be moveably connected to the proximal end portion 60. The slap hammer 62 can be configured to be gripped by the user and moved proximal-distal (along longitudinal axis L and along shaft 58).

Figure 5:
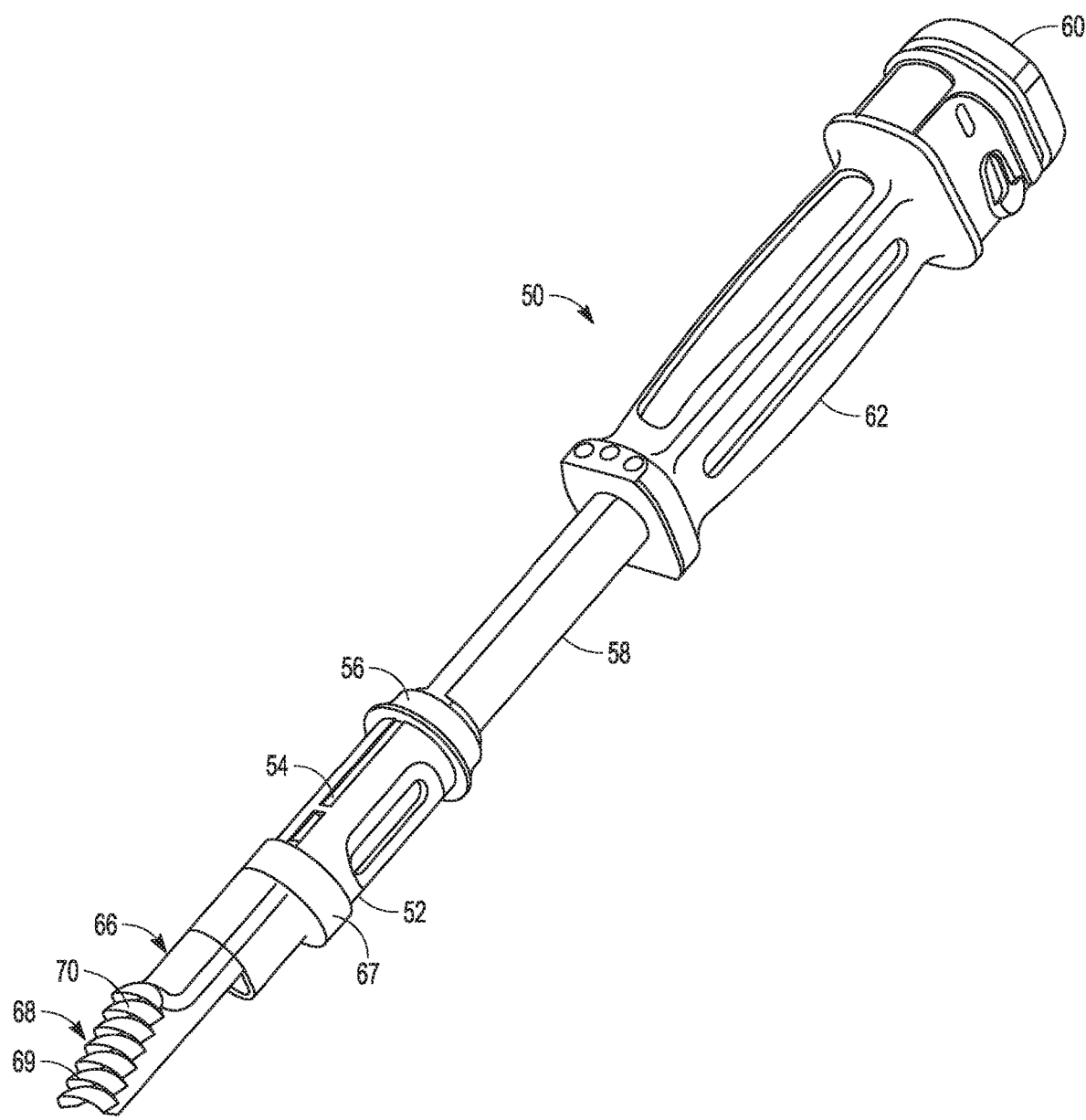
FIG. 5 show a perspective view of the multi-purpose handle of FIG. 4 coupled with an offset broach in accordance with an example of the present specification.

The distal tip 52 can be configured with one or more features 64 (FIG. 4) such as projections that are configured to engage with various other apparatuses such as the offset broach 66 of FIG. 5. The pin 54 can be moveable (extendible and retractable) generally along the longitudinal axis L of the tool 50. In an extended position, the pin 54 can engage with the apparatuses mounted to the distal tip 52 such as the offset broach of FIG. 5. The pin 54 can be biased by spring (not shown in FIG. 4 but shown in FIGS. 10A-10D and 11B) or other means into the extended position shown in FIG. 4. The collar 56 can be coupled to the pin 54 and can act as a mechanism to retract the pin 54 if desired.

FIG. 5 shows the offset broach 66 mounted to the distal tip 52 at a proximal portion 67. The proximal portion 67 of the offset broach 66 can be engaged in such position by the pin 54 to lock the offset broach 66 in such position. The offset broach 66 includes a distal portion 68 that is configured as a cutting surface 69 along only one surface 70 thereof. This cutting surface 69 can be tapered with teeth or other type of cutting edges and/or surfaces.

Figure 5A:
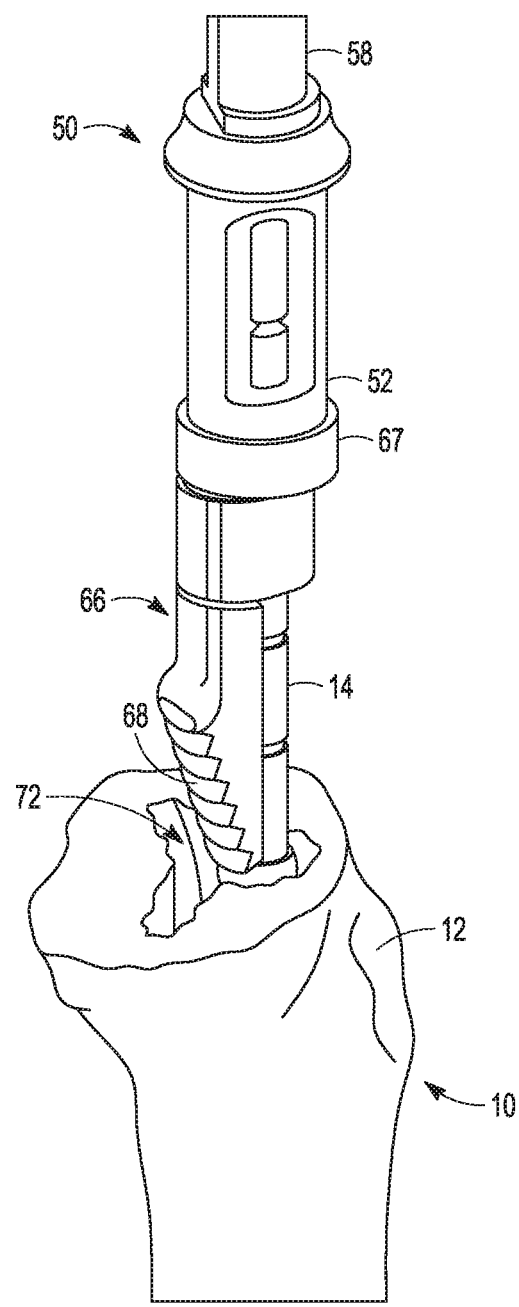
FIGS. 5A, 6A and 6B show the multi-purpose handle and offset broach being disposed longitudinally along the shaft the reamer to the tibia and removing bone from the tibia to create a recess in accordance with an example of the present application.

As shown in FIG. 5A, the offset broach 66 and handle 50 can be cannulated so as to be capable of receiving the reamer 14 therein. More particularly, the handle 50 can be cannulated along longitudinal axis L (FIG. 4) such that at least portions of the distal tip 52, the shaft 58, and/or the proximal end portion 60 (FIG. 4) are cannulated. The offset broach 66 can be similarly cannulated between distal portion 68 and proximal portion 67. As shown in FIG. 5A, such cannulated configuration allows the handle 60 and the offset broach 66 to be inserted down onto the reamer 14 in a proximal to distal manner. Once positioned and receiving the reamer 14, the offset broach 66 can be brought distal with controlled motion into contact with the proximal end 12 of the tibia 10 to remove bone. This can create a recess such as recess 72 of FIG. 5A.

Figure 6A:
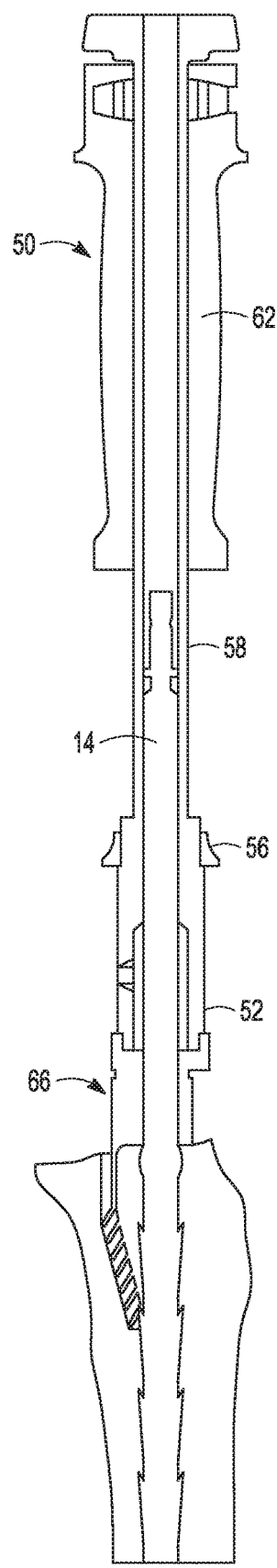
Figure 6B:
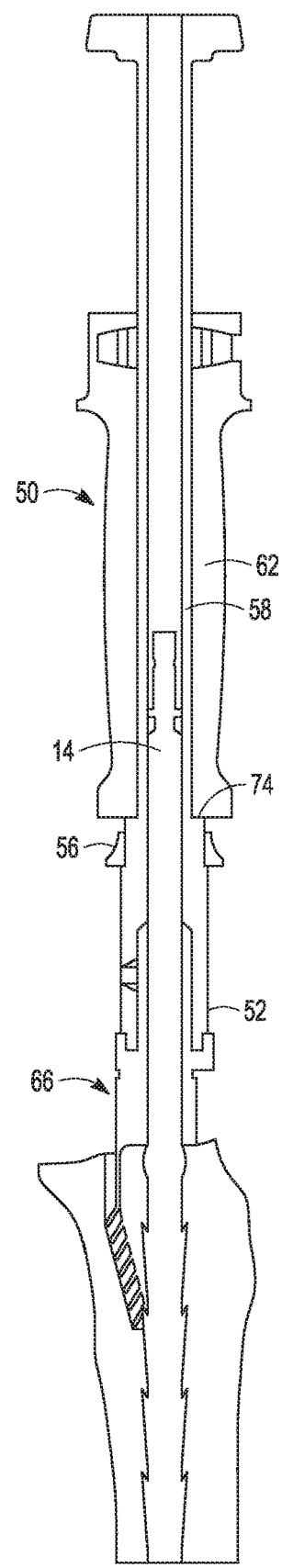

FIGS. 6A and 6B show a cross-section of the handle 50, the offset broach 66 and the reamer 14. The reamer 14 is received in the cannulated handle 50 and offset broach 66. FIG. 6B shows movement of the slap hammer 62 along the shaft 58 and the proximal end portion 60 from the position of FIG. 6A. The movement of the slap hammer 62 can be controlled movement generally proximal-distal along the longitudinal axis L (FIG. 4) which can be substantially co-aligned with a longitudinal axis of the reamer 14. The slap hammer 62 can be configured to strike an enlarged surface 74 of the shaft 58 proximal of the collar 56 as shown in FIG. 6B. This striking action provides a proximal-distal force along the shaft 58 through the distal tip 52 to the offset broach 66. This force can also cause the cutting surface 69 of the offset broach 66 to contact the bone to create the recess 72. Additionally or alternatively, the slap hammer 62 can be configured to be used to extract the offset broach 66 from the bone. In some examples, the offset broach 66 via the handle 50 can be impacted into the bone using a tool to strike the proximal end portion 60 rather than using impaction via the slap hammer 62. In some examples, the slap hammer 62 can be configured to be locked to the proximal end portion 60 or alternatively against enlarged surface 74 to restrain the slap hammer 62 from movement along the proximal end portion 60 and the shaft 58. The slap hammer 62 can be released when desired for movement as described above.

As discussed above, because the slap hammer 62 is coupled to the shaft 58 and the proximal end portion 60 movement of the slap hammer 62 and forces generated thereby are along the longitudinal axis L of the handle 50. Because the handle 50 and the offset broach 66 can be cannulated to receive the reamer 14 co-alignment between the longitudinal axis L of the handle 50 and a longitudinal axis of the reamer 14 is facilitated. Forces from the slap hammer 62 strike can be directed with the reamer 14 as a guide in a desired direction (e.g., proximal to distal) to create the recess 72. Off center striking forces in a direction tangential to that of the longitudinal axes can be avoided or minimized, thereby protecting the preparation of the bone.

Figure 7A:
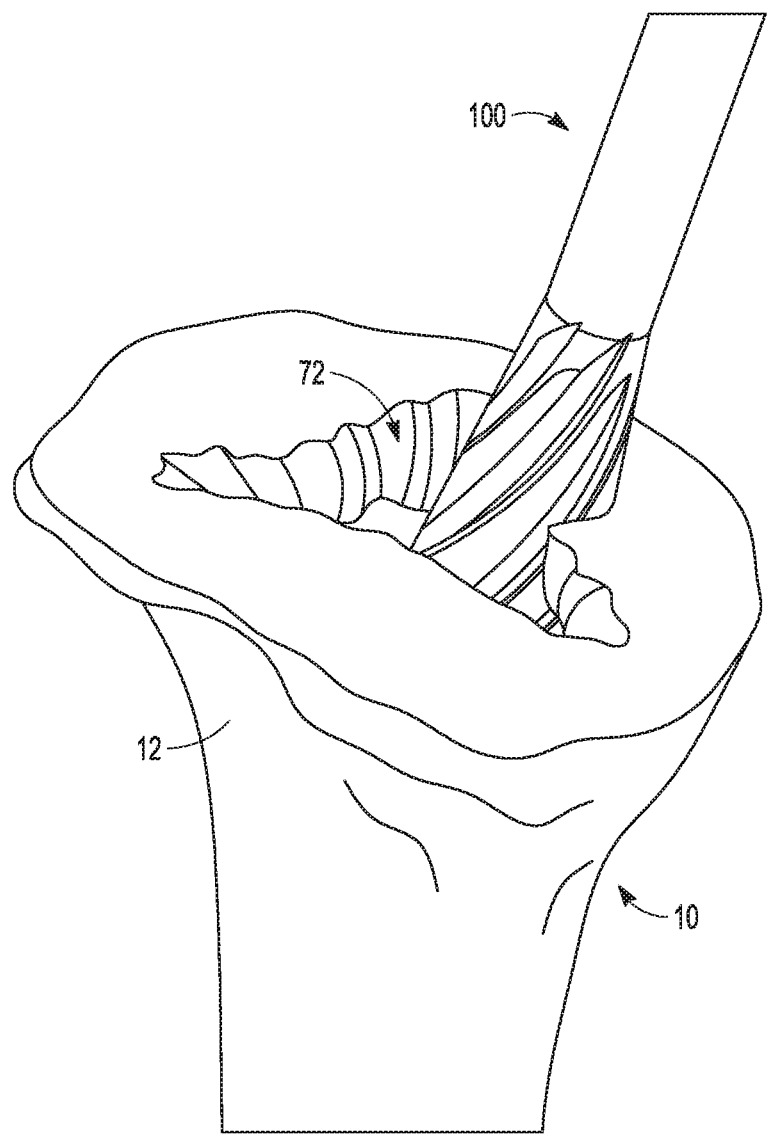
FIG. 7A is a perspective view of a tilt reamer having a tapered cutting section removing bone from the tibia to create a recess in accordance with an example of the present application.
Figure 7B:
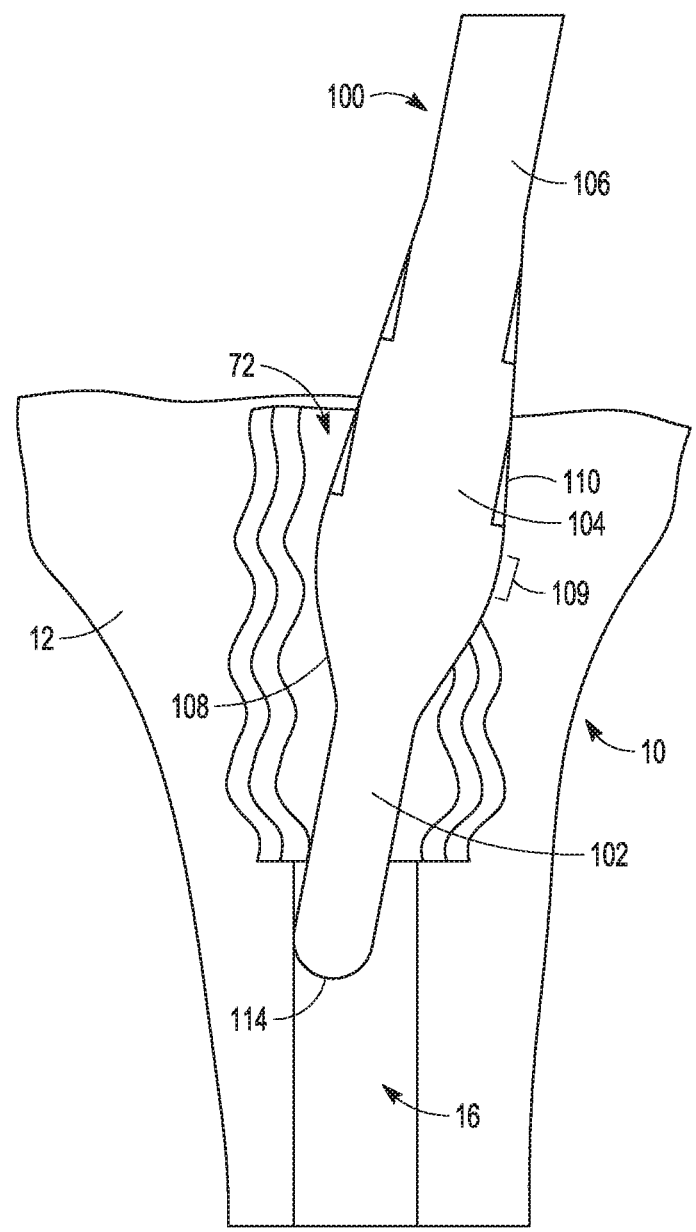
FIG. 7B is a cross-sectional view of the tilt reamer of FIG. 7A inserted in and removing bone from the tibia to create a recess in accordance with an example of the present application.
Figure 7C:
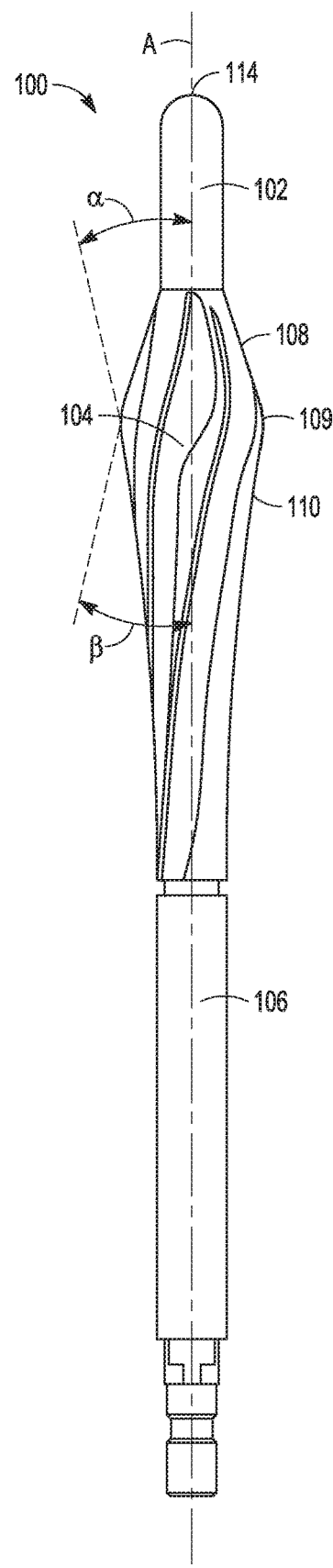
FIG. 7C is a plan view of the tilt reamer of FIGS. 7A and 7B.

FIGS. 7A and 7B show a tilt reamer 100 that can be used in addition to or in alternative to the offset broach 66 (FIGS. 5-6B). FIG. 7A shows the tilt reamer 100 can be used to remove bone from the proximal portion 12 of the tibia 10 to create the recess 72. The title reamer 100 can have a back angled taper portion to minimize the risk of over reaming the bone. FIG. 7B shows a cross-section of the tilt reamer 100 in the tibia 10. As shown in FIGS. 7B and 7C, the tilt reamer 100 can include a distal nose portion 102, a cutting portion 104 and a proximal shaft portion 106. The cutting portion 104 can include a first tapered section 108 and a second tapered section 110.

The distal nose portion 102 can extent longitudinally to the cutting portion 104. The distal nose portion 102 can be configured to reference the recess 16 of the tibia 10. The recess 16 can be the intramedullary canal of the tibia 10 and/or can be the recess formed by the reamer 14. The distal nose portion 102 can include a rounded blunt tip 114. The longitudinal length of the distal nose portion 102 can vary from embodiment to embodiment.

The cutting portion 104 can have an enlarged diameter relate to the distal nose portion 102 and the proximal shaft portion 106. The first tapered section 108 can be disposed distal of the second tapered section 110 and can connect with the distal nose portion 102. The nose portion 104 can have a length of between about 15 mm and about 70 mm as measured from the rounded blunt tip 114 to the beginning of the first tapered section 108. The rounded blunt tip 114 can have a diameter between about 6 mm and about 16 mm and can have a radius of 5 mm according to various examples.

The tapered section 108 can be a leading portion and the second tapered section 110 can be a trailing portion during surgical application. As shown in FIG. 7C, the first tapered section 108 can have a first taper angle α (also called a leading angle) of between about 10 degrees and 40 degrees as measured from the surface of the tapered section 108 to a longitudinal axis A. The length of the first tapered section 108 along the longitudinal axis A can be between about 11 mm to about 24 mm. The second tapered section 110 can have an angle of between about 4 degrees and about 16 degrees as measured from the surface of the tapered section 108 to the longitudinal axis A. The length of the second tapered section 110 along the longitudinal axis A can be between about 20 mm to about 60 mm.

The first taper angle α can differ relative to a second taper angle β of the second tapered section 110 as measured from the longitudinal axis A. The second taper angle β can be inverted in measurement direction relative to first taper angle α. In other words, the second tapered section 110 can have a back taper relative to the first tapered section 108. In some examples the longitudinal length of the first tapered section 108 differs from that of the second tapered section 110.

In other examples, the tilt reamer 100 can be configured with no first tapered section 108 but only the second tapered section 110. The second tapered section 110 can be disposed proximal of the first tapered section 108 and can connect with the proximal shaft portion 106. As shown in both FIGS. 7B and 7C, the second tapered section 110 can be separated from the first tapered section 108 by a region 109 in some examples. The region 109 can comprise a region with a largest cross-sectional diameter for the tilt reamer 100 and can be substantially flat have a surface parallel to that of the longitudinal axis A of FIG. 7C). This region 109 can comprise a sharp transition (e.g., a ridge line) between the first tapered section 108 and the second tapered section 110 in some examples. In examples where the region 109 is flat, the region 109 can have a length relative to longitudinal axis A (FIG. 7C) of a few mms in other examples. Region 109 can have a diameter between about 16 mm and about 60 mm.

The second tapered section 110 can have a decreasing diameter as measured distal-to-proximal along the longitudinal axis A (FIG. 7C) from the region 109 to the proximal shaft portion 106. In contrast, the first tapered section 108 can have an increasing diameter as measured distal-to-proximal along the longitudinal axis A from the nose portion 102 to the region 109.

Figure 8A:
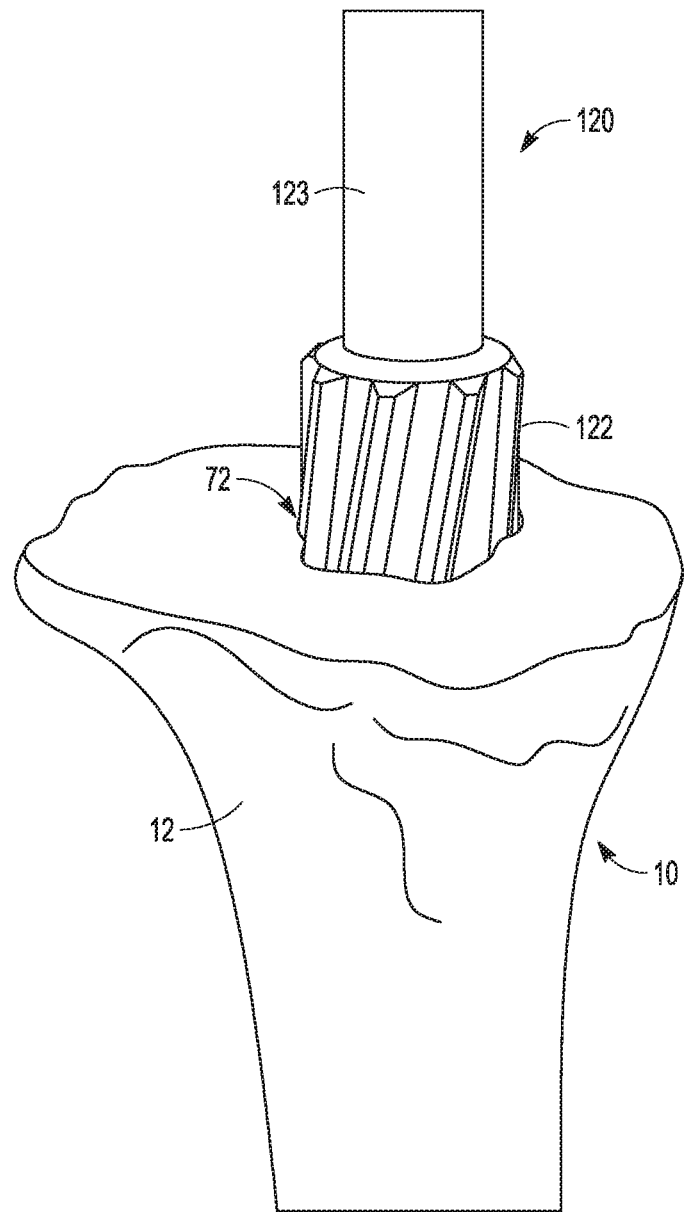
FIGS. 8A-8C show a cannulated reamer removing bone from the tibia to create a recess, the cannulated reamer can be inserted over a post coupled to a first stem provisional assembly in accordance with an example of the present application.
Figure 8B:
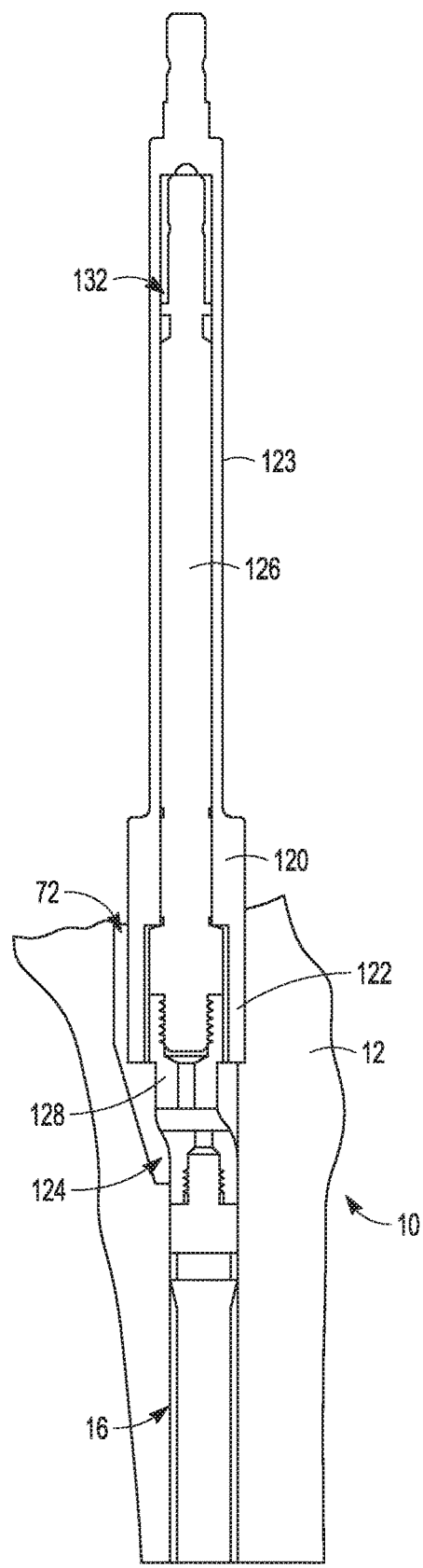
Figure 8C:
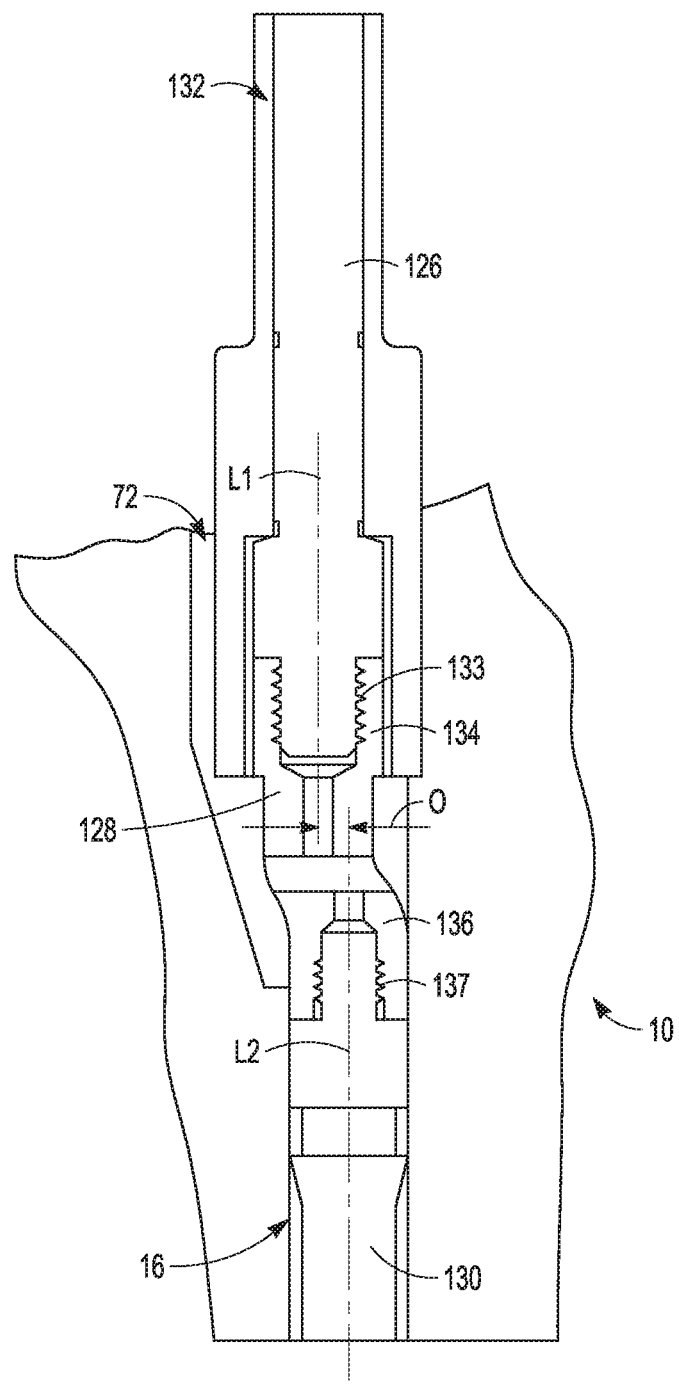

FIGS. 8A, 8B and 8C show a cannulated reamer 120 that can be used to prepare the tibia or femur for provisional stem housings and/or to remove initial bone to receive cone/sleeve broaches or tibial keel broaches. FIG. 8A shows the cannulated reamer 120 can be used to remove bone from the proximal portion 12 of the tibia 10 to create the recess 72. FIGS. 8B and 8C show a cross-section of the cannulated reamer 120 in the tibia 10. The cannulated reamer 120 can include a cutting portion 122 and a shaft portion 123. FIGS. 8B and 8C also illustrate a stem provisional assembly 124 disposed in the recesses 72 and 16 of the tibia 10. The stem provisional assembly 124 can include a post extension 126, an adaptor 128 and a stem extension 130. According to further examples, the stem provisional assembly 124 can include the post extension 126 and a monolithic stem provisional (shown subsequently).

As shown in FIGS. 8B and 8C, a passage 132 can be formed by the cutting portion 122 and a shaft portion 123. This passage 132 can be configured to receive the post extension 126 of the stem provisional assembly 124. The post extension 126 can be configured to guide the cutting portion 122 of the cannulated reamer 120 into the tibia 10 to form the recess 72.

The post extension 126 can be partially disposed within the recess 72 and can extend proximally to a position above the tibia 10 as shown in FIG. 8C. The post extension 126 can be removably coupled to the adaptor 128 by the thread 133 in FIG. 8C, for example. The cannulated reamer 120 can also be positioned over a proximal portion 134 of the adaptor 128 in the recess 72.

The adaptor 128 can be positioned in the recess 72 and can have a distal portion 136 disposed distal of the proximal portion 134 and the post extension 126. FIGS. 8B and 8C show the stem provisional assembly 124 can have an offset O provided by the adaptor 128. More particularly, the post extension 126 and the proximal portion 134 of the adaptor 128 can define a first longitudinal axis L1 that is offset O a distance from a second longitudinal axis L2 defined by the stem extension 130 and the distal portion 136 of the adaptor 128. The offset O as measured between axis L1 and axis L2 can be in one or multiple directions such as proximal, distal, medial, and lateral, for example.

The stem extension 128 can be positioned in the recess 16 and can be removably coupled to the distal portion 136 of the adaptor 128 by thread 137 (FIG. 8C), for example. The stem extension 128 can extend distal of the adaptor 126 along the recess 16.

Figure 9A:
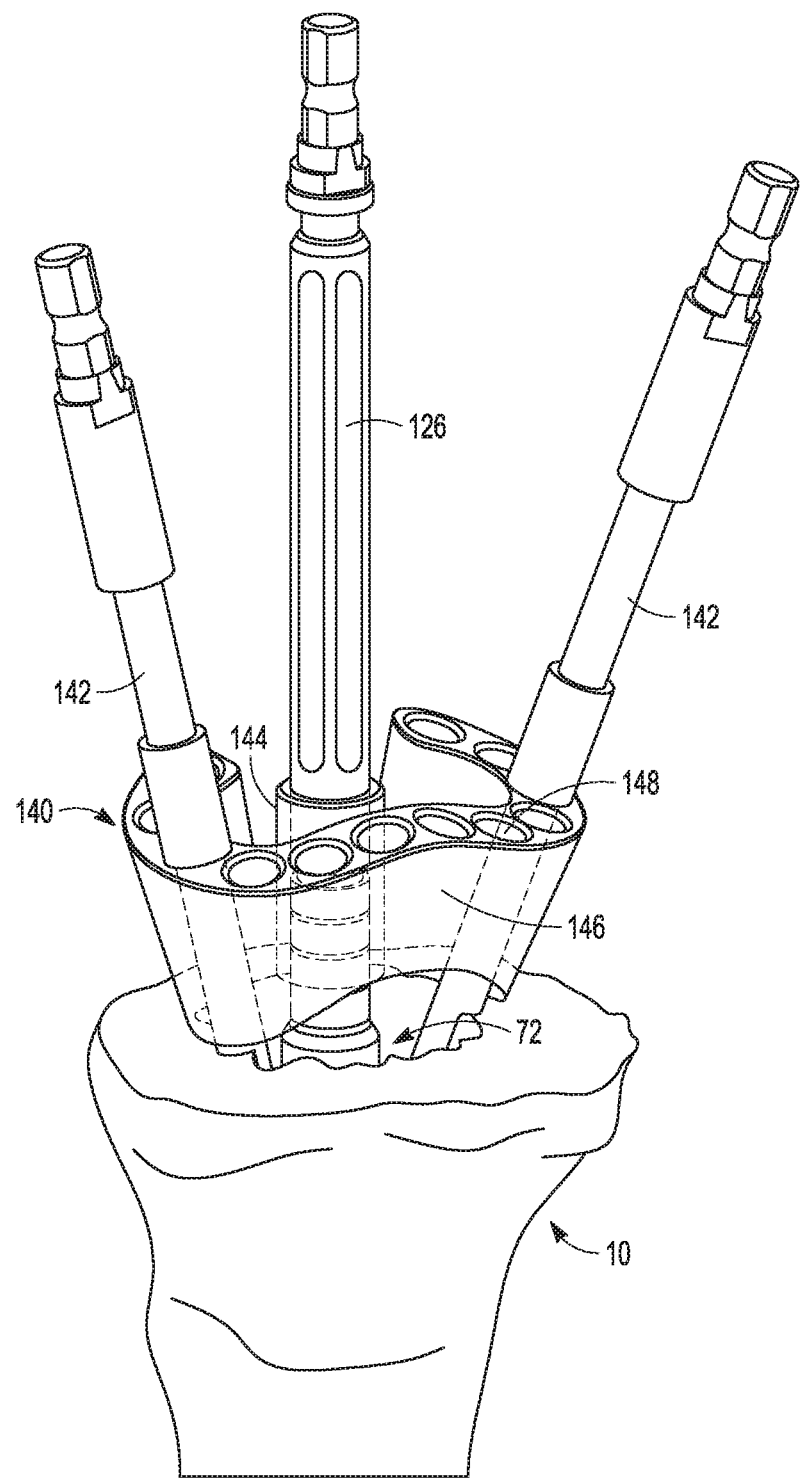
FIGS. 9A and 9B show a drill guide and drills that can be used to remove bone from the tibia to create a recess in accordance with an example of the present application.
Figure 9B:
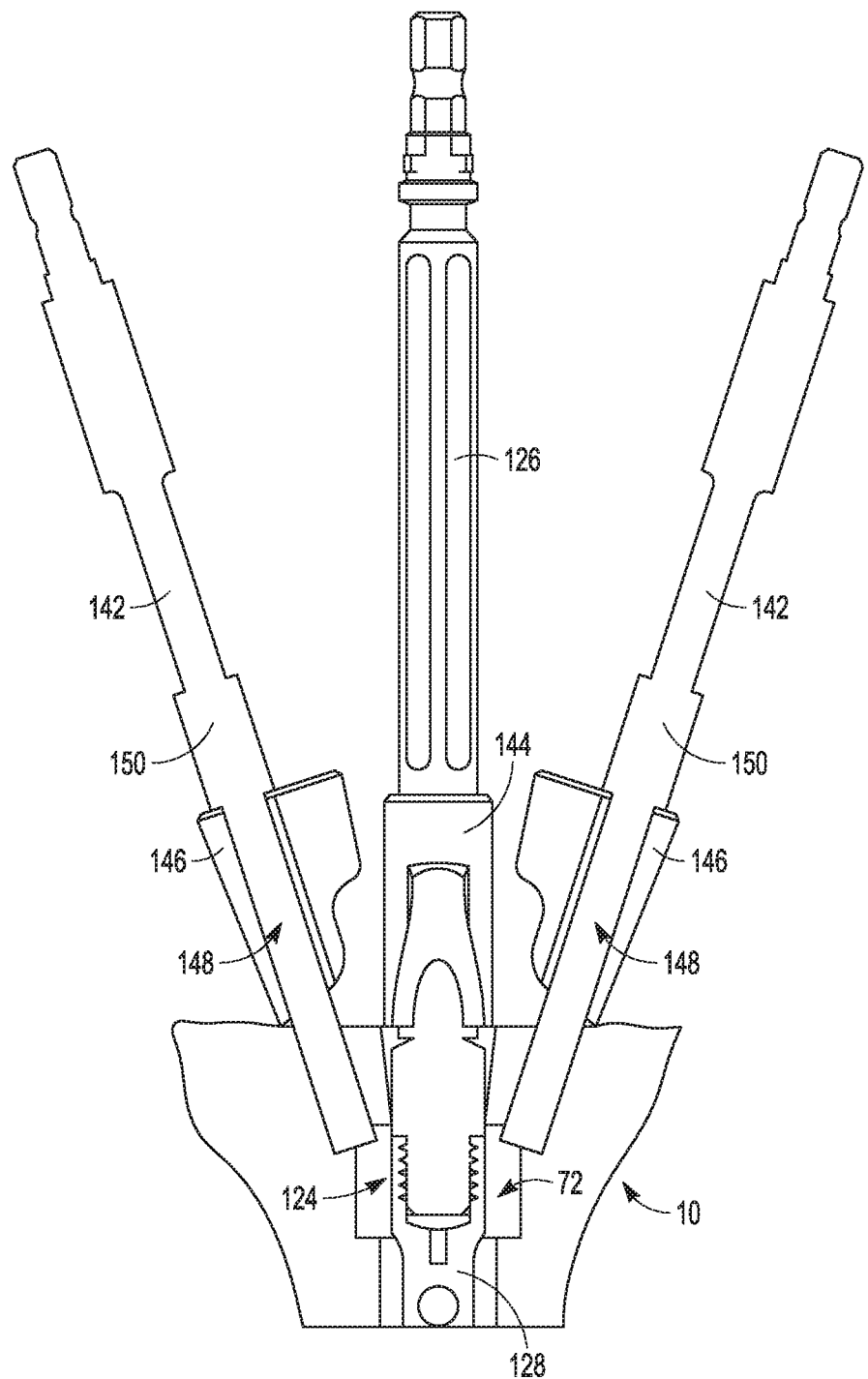

FIGS. 9A and 9B show a drill guide 140 that can be used in addition to the cannulated reamer 120 (FIGS. 8A-8C) in preparation of broaching for a cone or a sleeve implant. More particularly, the drill guide 140 can be configured to pre-drill out the bone in a desired shape and area prior to broaching for the sleeve component or the cone component. Pre-drilling the bone using the drill guide 140 can reduce the risk of bone fracture during broaching. FIG. 9A shows the drill guide 140 mounted to the post extension 126 of the stem provisional assembly 124 (FIG. 9B) and directing one or more drills 142 to remove bone from the proximal portion 12 of the tibia 10 to create the recess 72 (this recess can be larger than the recess created by the cannulated reamer 120, and can be proximal to the recess(es) created by the offset broach 66 (FIGS. 4-6B) and/or the tilt reamer 100 (FIGS. 7A and 7B). The drill guide 140 can be used to direct the one or more drills 142 along a desired pathway in order to break bone up along a perimeter or designated area to create the recess 72.

The drill guide 140 can include a coupling 144 and a body 146. The body 146 can include a plurality of apertures 148 (FIG. 9A) configured to receive the one or more drills 142. FIG. 9B shows a cross-section of the drill guide 140 and shows portions of the body 146 with two apertures 148 and the coupling 144. The coupling 144 has an aperture and is configured to receive and rest on the post extension 126. The coupling 144 can be connected to the body 146 and can retain the body 146 above the tibia 10.

FIG. 9B shows the drill guide 140 mounted to the post extension 126 proximal of the tibia 10 and recess 72. As shown in FIG. 9B, the drill guide 140 can be configured to direct the one or more drills 142 distally into the tibia 10 anterior, posterior, medial and/or lateral of the stem provisional assembly 124. The tips of the one or more drills 142 can be disposed adjacent to but spaced from the adaptor 128. Each of the one or more drills 142 can be provided with an enlarged diameter section 150 to limit the distal travel of the one or more drills 142 so contact with the adaptor 128 can be avoided.

Figure 10A:
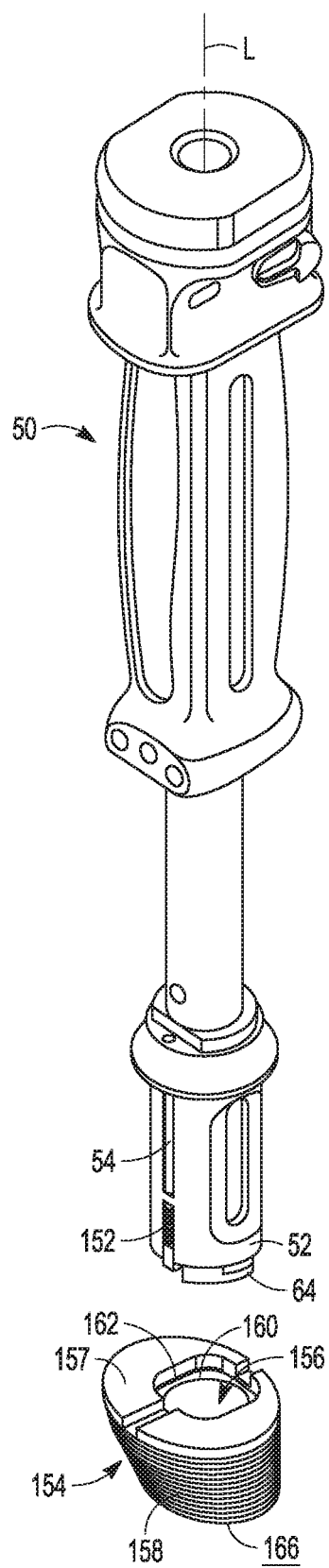
FIGS. 10A-10E show the multi-purpose handle of FIGS. 5-6B and a second provisional component configured to simulate a cone in accordance with an example of the present application.
Figure 10B:
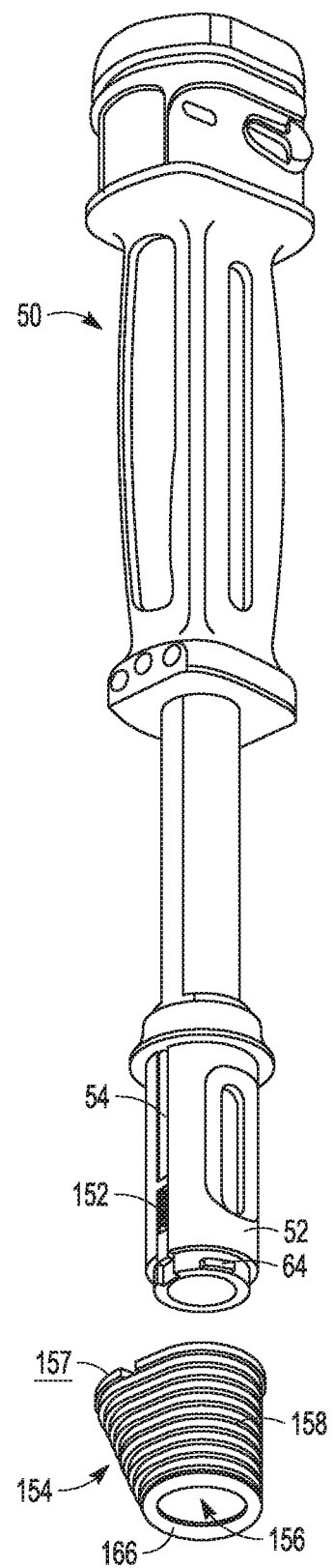

FIGS. 10A-10E again show the multi-purpose handle 50 previously shown and described in reference to FIGS. 4-6B. Thus, the details of the handle 50 will not be discussed again in great detail. FIGS. 10A-1.0E illustrate the features previously discussed including the distal tip 52 and the pin 54. FIGS. 10A-10D additionally show a bias element 152 configured to dispose the pin 54 in the extended position. FIGS. 10A-10B also show the one or more features 64 (e.g., projections) that are configured to engage with various other apparatuses such as the offset broach 66 of FIG. 5 and a second provisional component 154 of FIGS. 10A-10E.

Figure 10C:
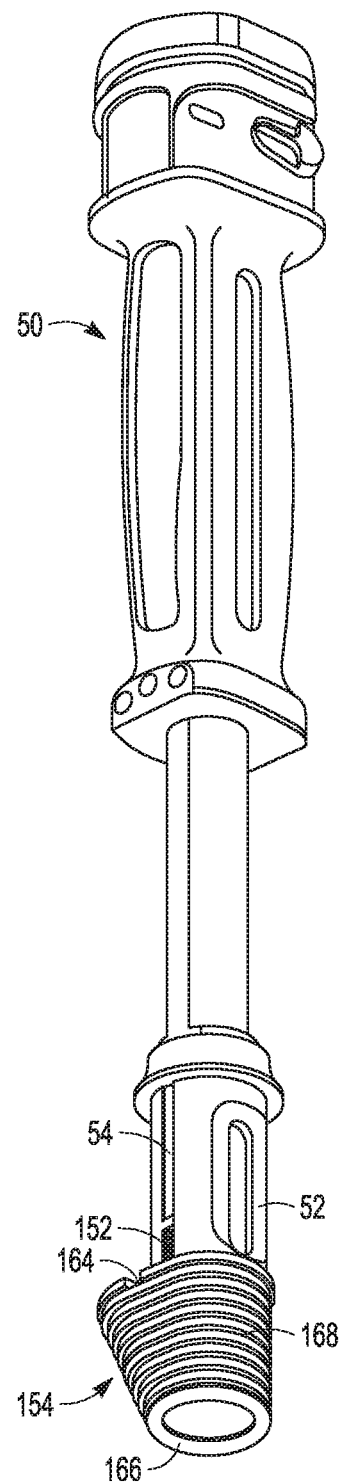
Figure 10D:
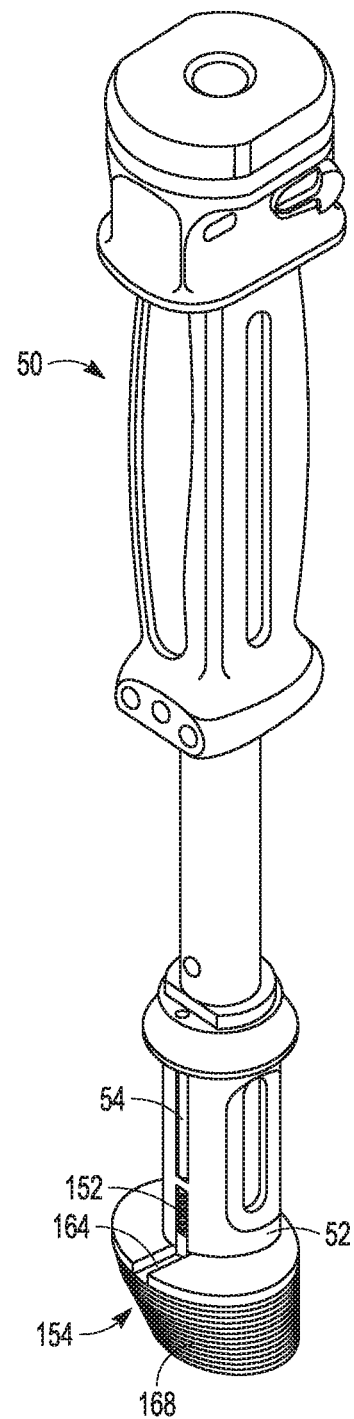
Figure 10E:
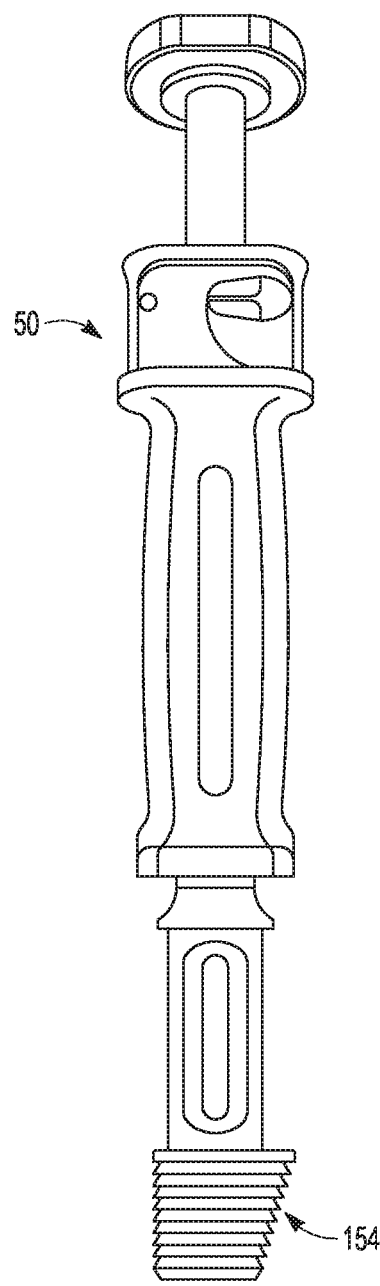

FIGS. 10A and 10B show the handle 50 disengaged from the second provisional component 154 while FIGS. 10C-10E show the handle 50 engaged with the second provisional component 154.

As shown in FIGS. 10A and 10B, the second provisional component 154 includes a recess 156, a proximal surface 157 (FIG. 10A) and side exterior surfaces 158. As shown in FIG. 10A, the recess 156 can include passages 160 that are configured to allow for passage of the one or more features 64. The second provisional component 154 can additionally include one or more lips 162 partially formed by the proximal surface 157 designed to capture the one or more features 64 upon rotation (e.g., a quarter turn rotation) of the handle 50 about the longitudinal axis L.

As shown in FIGS. 10C-10D, when the one or more features 64 are captured under the one or more lips 162, the pin 54 can extended distally into a second recess 164. Such an arrangement can secure the second provisional component 154 to the handle 50 as the pin 54 retrains rotation of the second provisional component 154 about the longitudinal axis L (FIG. 10A).

Figure 21:
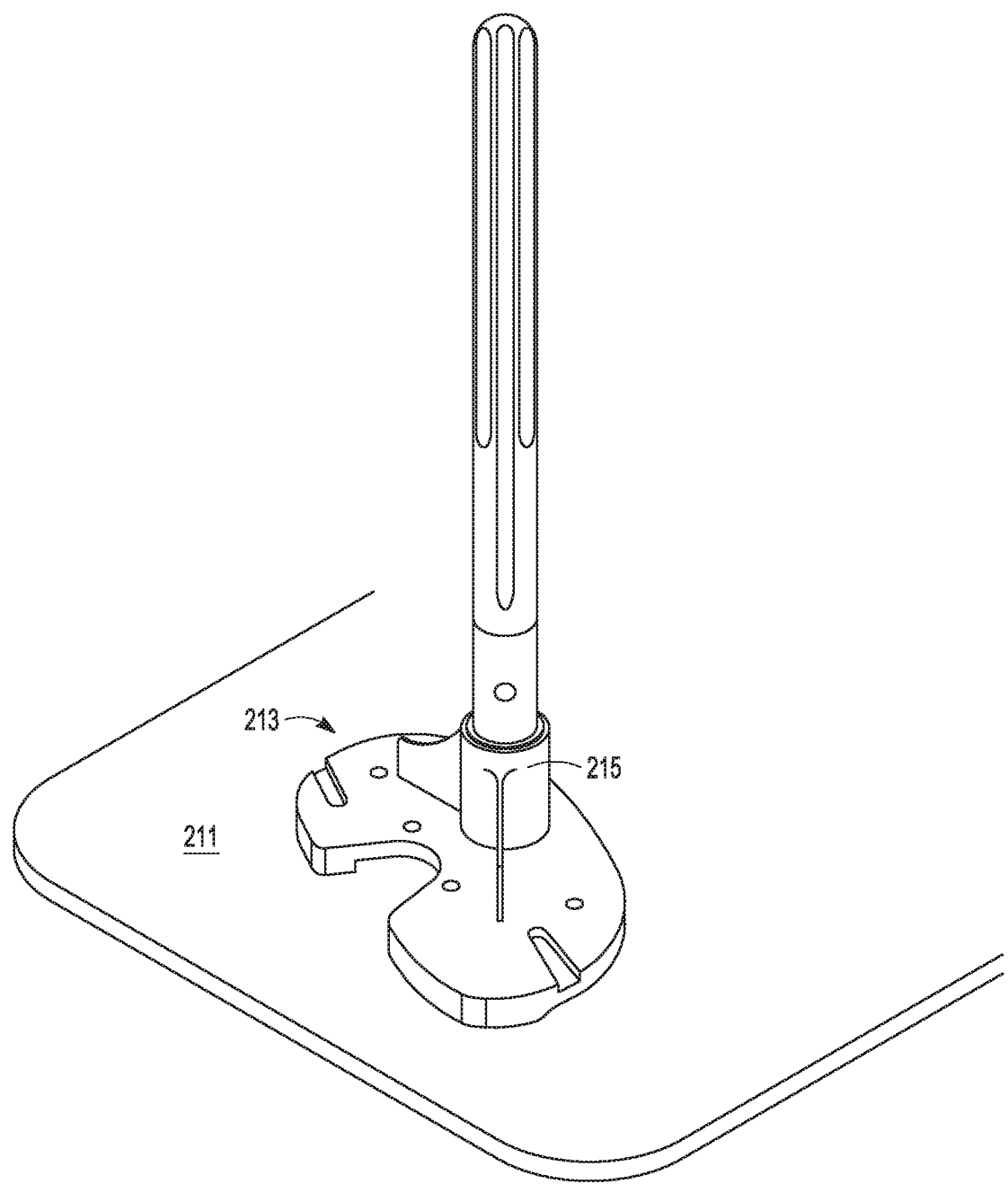
FIG. 21 shows a perspective view of an alternative provisional tibial assembly having the second provisional component configured to simulate a keel removed from the tibia and placed on a work space to be used for construction of a second tibial implant assembly in accordance with an example of the present application.

The second provisional component 154 can be configured (e.g., sized and shaped along the side exterior surfaces 158) to simulate a shape of at least one of a sleeve component or a cone component of an implant. More particularly, the second provisional component 154 can be configured (shaped and sized) to simulate a shape and size of a sleeve component of an implant. Another example is provided in subsequent discussion of FIG. 21 shows a provisional component configured to simulate a keel component of an implant.

As will be discussed and shown subsequently, the recess 156 can comprise a through hole from the proximal surface 157 to a distal surface 166 (FIGS. 10A-10C). The side exterior surfaces 158 can extend from the proximal surface 157 to the distal surface 166. According to one example, the second provisional component 154 can be configured as a broach. Thus, the side exterior surfaces 158 can include a plurality of cutting edges 168 (FIGS. 10C and 10D) that can be used with the handle 50 to at least partially create the recess in the tibia.

One or more of the side exterior surfaces 158 and portions of the recess 156 can be tapered along their longitudinal lengths according to one example. Thus a cross-sectional area of a distal portion of the second provisional component 154 can differ and/or change from that of a cross-sectional area of a proximal portion.

Figure 11A:
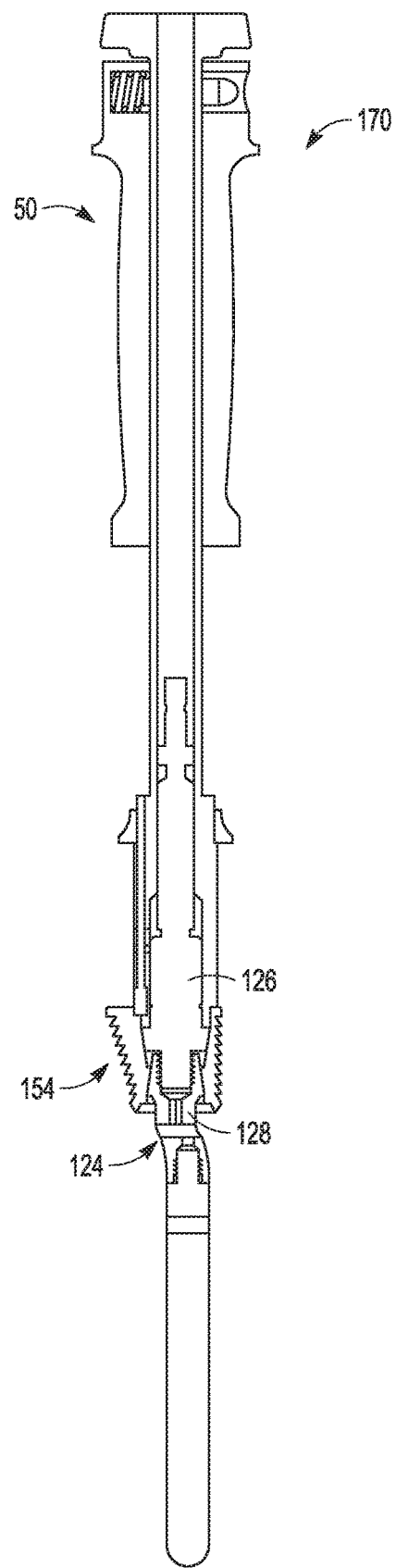
FIGS. 11A and 11B show cross-sectional views of the multi-purpose handle of FIGS. 10A-10E engaging an assembly of the second provisional component, the post and the first stem provisional assembly in accordance with an example of the present application.
Figure 11B:
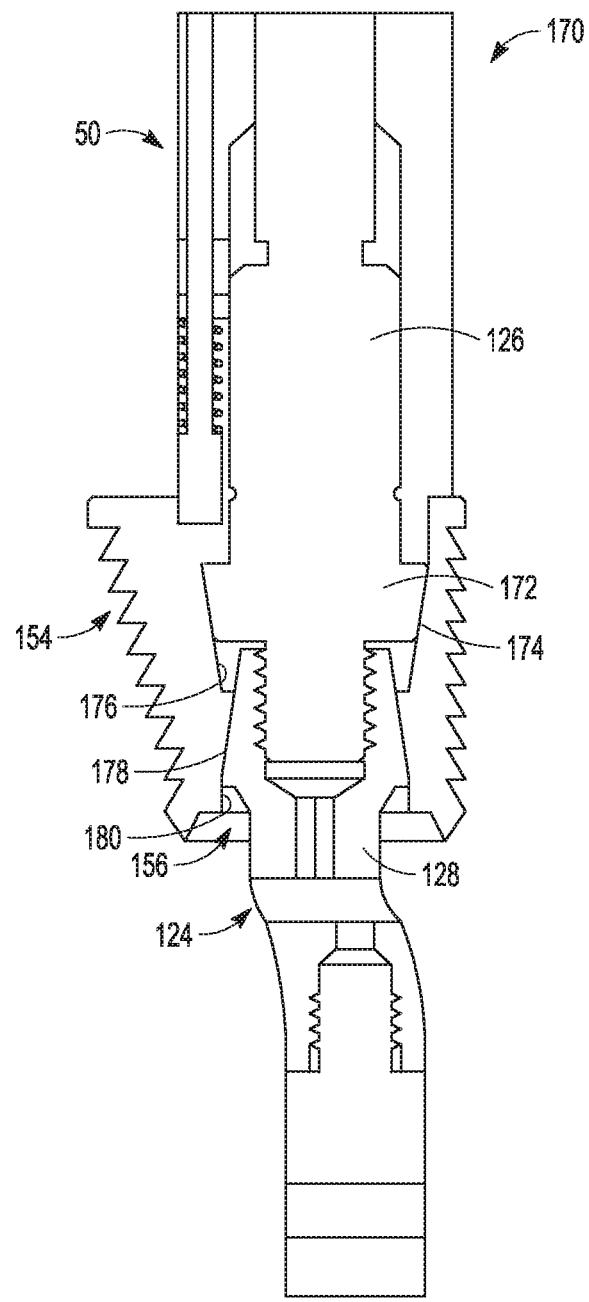

FIG. 11A shows an assembly 170 of the handle 50 with the second provisional component 154 and the stem provisional assembly 124. FIG. 11B shows an enlargement of portions of the assembly 170 including portions of the handle 50 and the stem provisional assembly 124.

FIGS. 11A and 11B show the second provisional component 154 engaged with the handle 50. The second provisional component 154 can be configured to receive portions of the stem provisional assembly 124 therein. More particularly, portions of the post extension 126 and the adaptor 128 can be disposed in the recess 156 of the second provisional component 154. The adaptor 128 can extend distally from the second provisional component 154. The post extension 126 can extend proximal of the second provisional component 154 and can be received by the handle 50. More particularly, the handle 50 can be cannulated to receive the post extension 126 therein.

As best shown in FIG. 11B, the recess the post extension 126 can have a flared section 172 with an outer surface 174 that is tapered in a manner to interface and seat against a first tapered inner surface 176 that forms part of the recess 156 of the second provisional component 154 when the post extension 126 is threaded to secure with the adaptor 128. Additionally, the adaptor 128 can include a tapered outer surface 178 configured to interface and seat against a second tapered inner surface 180 that forms part of the recess 156 of the second provisional component 154 when the post extension 126 is threaded to secure with the adaptor 128. The tapers utilized by one or more of the post extension 126, the second provisional component 154 and the stem provisional assembly 124 can be self-holding (e.g., a Morse taper or the like) according to some examples. According to other examples, the tapers utilized by one or more of the post extension 126, the second provisional component 154 and the stem provisional assembly 124 can be self-releasing.

Figure 11C:
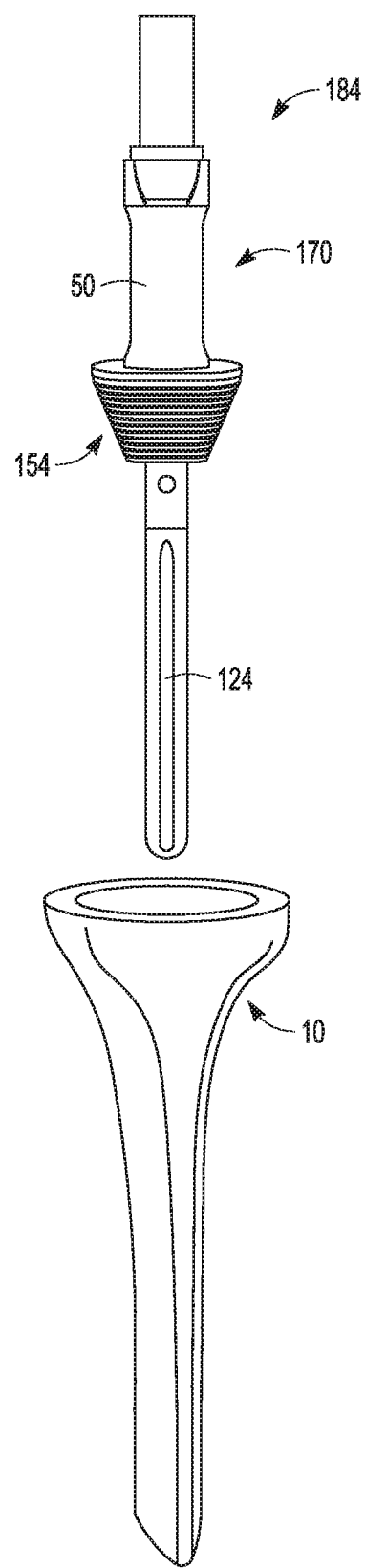
FIGS. 11C-11E are perspective views showing the handle being used to insert the assembly of the second provisional component, the post and the first stem provisional assembly into one or more recesses in the proximal tibia in accordance with an example of the present application.
Figure 11D:
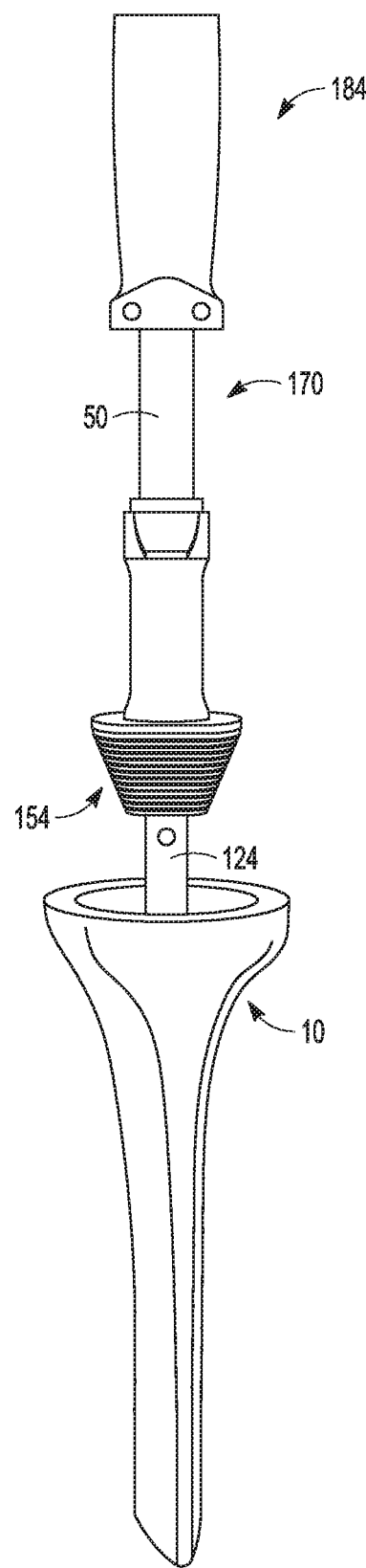
Figure 11E:
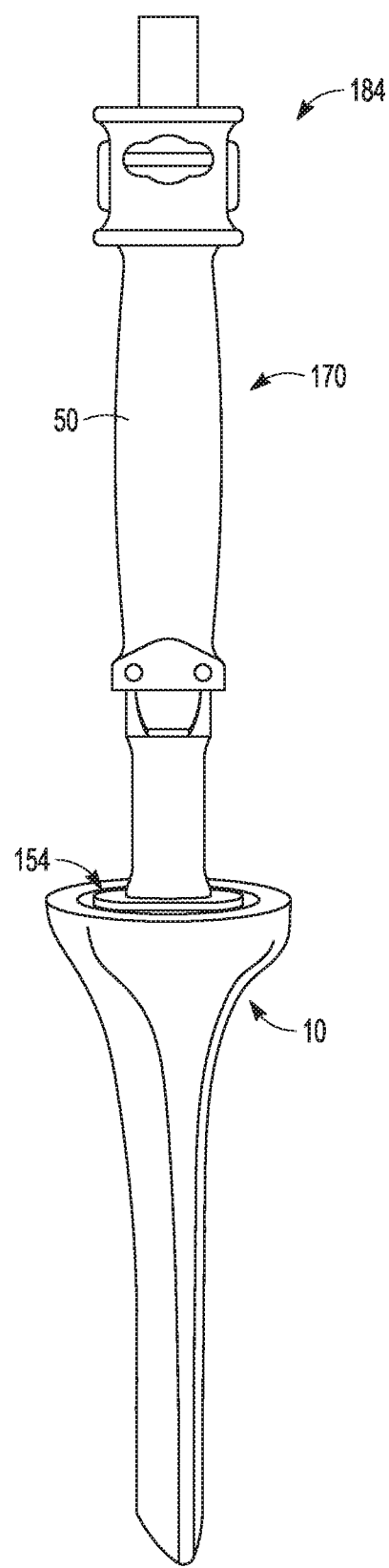

FIGS. 11C-11E show a method 184 whereby the assembly 170 of FIGS. 11A and 11B is disposed in the tibia 10. In particular, the assembly 170 is created by the process described in reference to FIGS. 10A-11B. The method 184 can include coupling the second provisional component 154 to the handle 50 and can further include coupling the stem provisional assembly 124 (FIGS. 11C and 11D) to the second provisional component 154 via the tapered surfaces and thread connection between the post extension and the adaptor discussed in reference to FIG. 11B. Coupling of the components to form the assembly 170 according to the method 184 can occur in vivo or external to the knee joint.

As shown in FIGS. 11C-11D the method 184 can include inserting the stem provisional assembly 124 and the second provisional component 154 into one or more recesses (e.g., recesses 72 and 16 of FIGS. 8B and 8C). This can allow the stem extension 130 to extend along the recess 16 (FIGS. 8B and 8C) and the second provisional component 154 to be inserted in the recess 72 (FIGS. 8B and 8C). The handle 50 can be configured to facilitate insertion of the stem provisional assembly 124 and the second provisional component 154.

Figure 12:
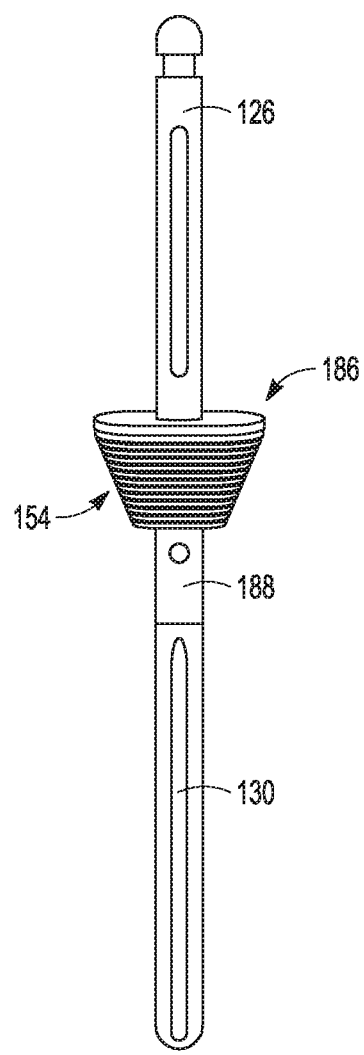
FIG. 12 shows an alternative assembly of the second provisional component, the post and a second stem provisional assembly in accordance with an example of the present application.

FIG. 12 shows a second assembly 186 comprised of the post extension 126, the second provisional component 154 and the stem extension 130 as previously described. FIG. 12 further shows a second adaptor 188 with substantially no offset along a longitudinal length thereof. Thus, the second adaptor 188 has one longitudinal axis of the second adaptor 188 that extends an entire length of the second adaptor 188.

Figure 13:
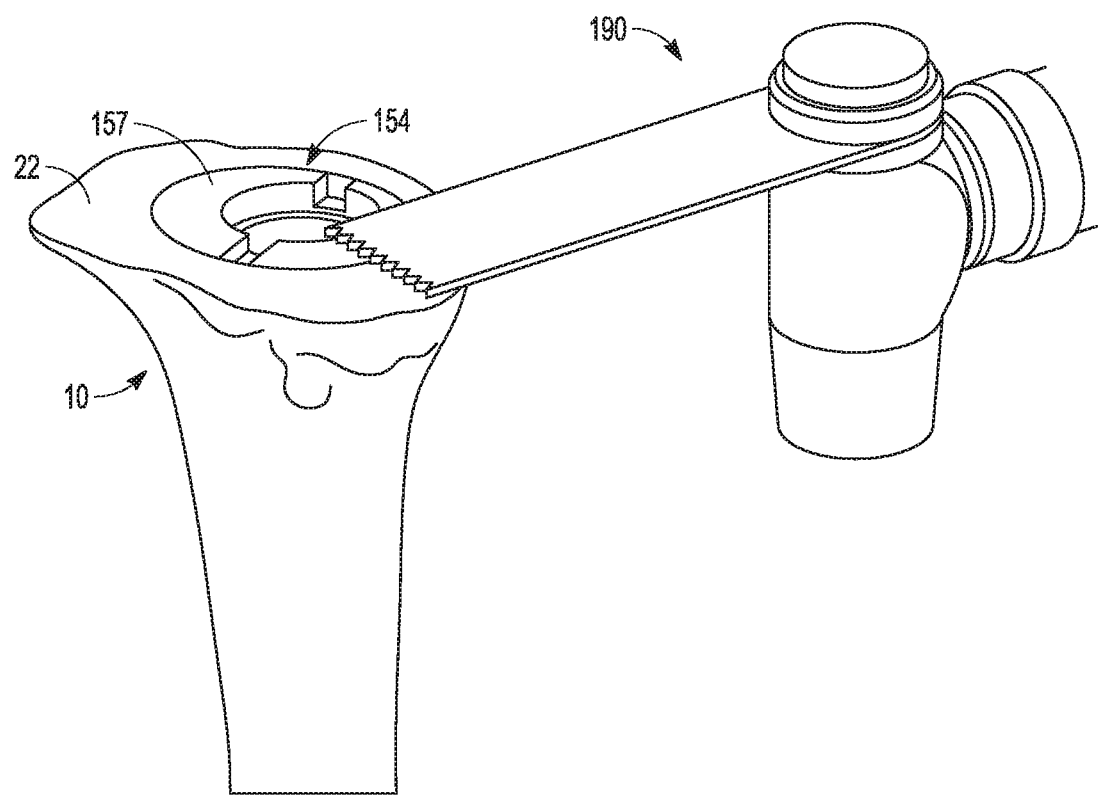
FIG. 13 shows a cutting tool resecting an end portion of the bone using a first surface of the second provisional component as a reference to set the resection plane in accordance with an example of the present application.

FIG. 13 shows a cutting instrument 190 such as a saw being used to remove portions of bone in a resection to create a resected surface that comprises the proximal surface 22 of the tibia 10. As shown in FIG. 13, the proximal surface 157 of the second provisional component 154 can be used to set a resection height for the proximal surface 22. More particularly, the tibia 12 can be resected substantially level with use of the proximal surface 157 such that the cutting instrument 190 blade is placed atop the proximal surface 157 and proximal surface 157 guides removal of the bone.

Figure 14A:
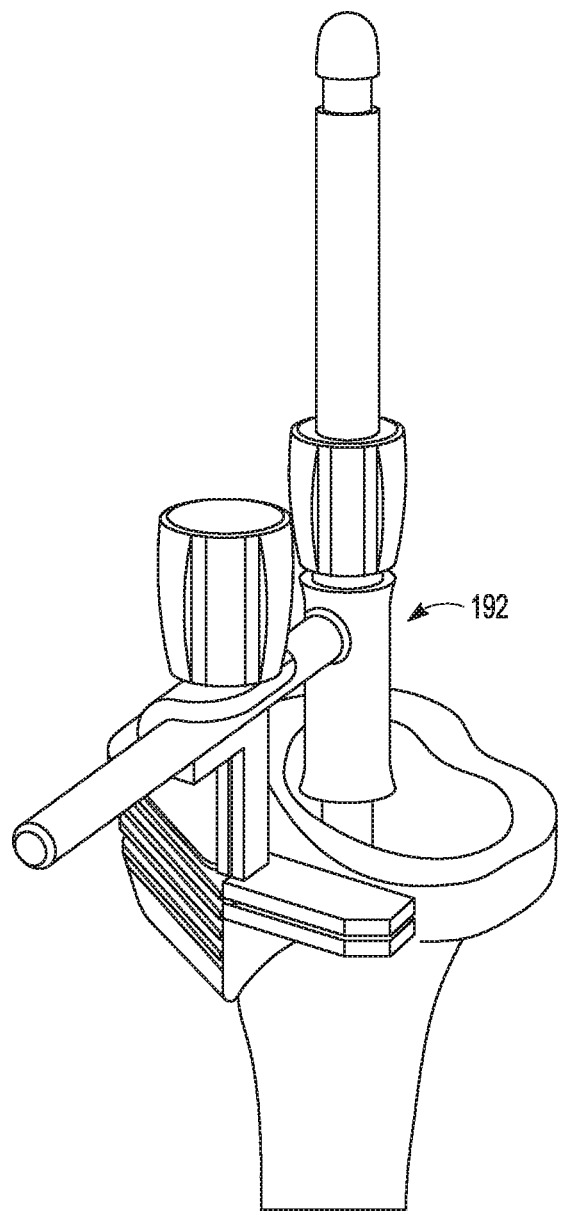
FIGS. 14A-14C show perspective views of a cut guide for guiding the cutting tool of FIG. 13 to remove the end portion of the bone in accordance with an example of the present application.
Figure 14B:
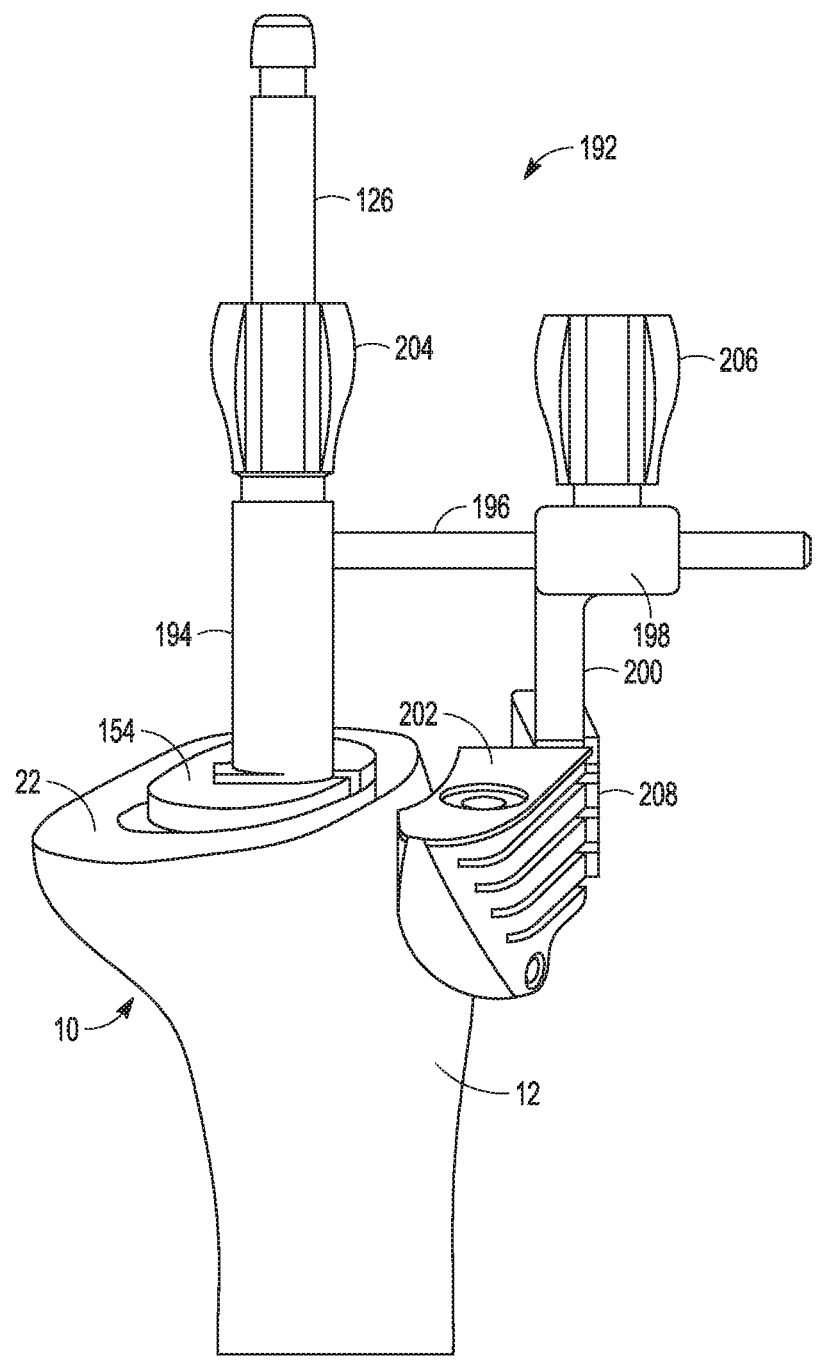
Figure 14C:
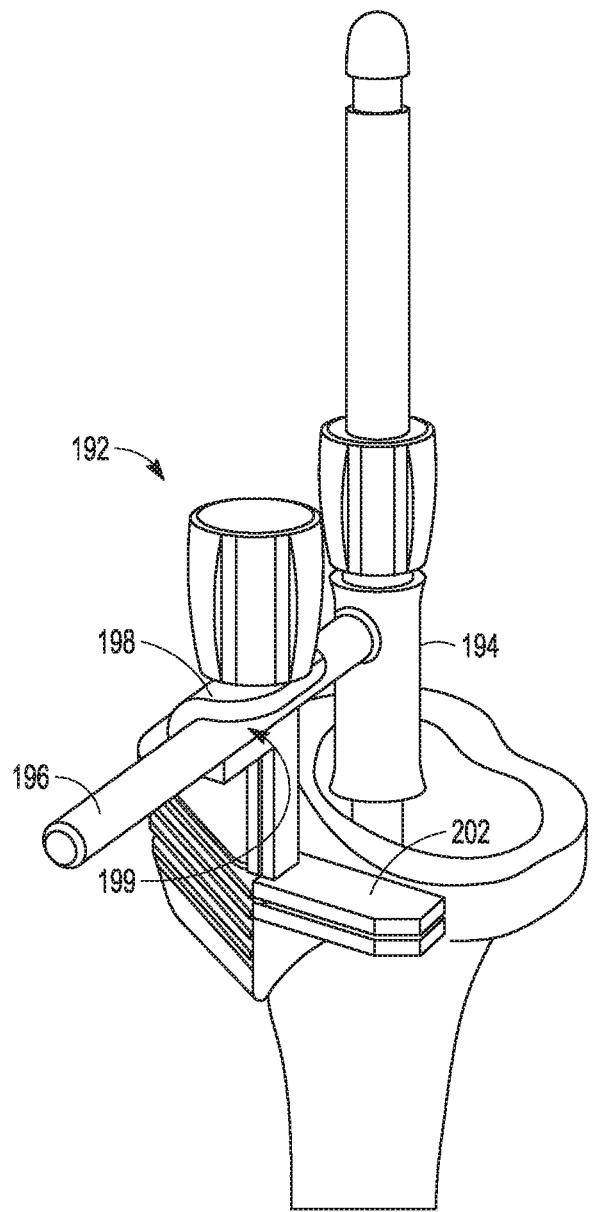

FIGS. 14A-14C show a cut guide assembly 192 that can be used with the cutting instrument 190 (FIG. 13). The cut guide assembly 192 can be used in addition to or in alternative to the resection method of FIG. 13. As shown in FIG. 14B, the cut guide assembly 192 can include a first collar 194, a first arm 196, a second collar 198, a second arm 200 and a body 202.

As shown in FIG. 14B, the cut guide assembly 192 can be assembled proximal to the second provisional component 154. The first collar 194 can comprise a boom that can be configured to couple with the post extension 126 or reamer 14. The first collar 194 can be releasably locked to the post extension 126 or reamer 14 by turning a knob 204, for example. The first arm 196 can connect with the first collar 194 and can project therefrom including in an anterior direction. The second collar 198 can be configured to receive the first arm 196. The second collar 198 can be moveable along a length of the first arm 196 and can be releasably locked thereon by turning a second knob 206, for example. As shown in FIG. 14C, the second collar 198 can have an opening 199 along a portion thereof. The opening 199 can facilitate removal of components of the cut guide assembly 192 including the first collar 194 and first arm 196 (along with the reamer 14) without having to un-pin the body 202 from the bone. In particular, the opening 199 can be sized to allow the first arm 196 to pass therethrough when not engaged by the second knob 206. Thus, the first arm 196 and first collar 194 can be removed without a position of the body 202 being changed relative to the bone.

Referring again to FIG. 14B, the second arm 200 can be connected to the second collar 198 and extends generally distal to connect to the body 202. The body 202 can be disposed forward of an anterior part of and adjacent the proximal portion 12 of the tibia 10. The body 202 can be positionally adjusted relative to the tibia 10 using the first collar 194 and the second collar 198. The body 202 can be configured with a plurality of slots 208 and pin holes therein. A physician can select one or more of the plurality of slots 208 to guide the cutting instrument 190 (FIG. 13) when making the resection to remove bone to create the proximal surface 22. In some examples, the plurality of slots 208 can be placed at predetermined intervals from one another (e.g., 5 mm increments).

Figure 15:
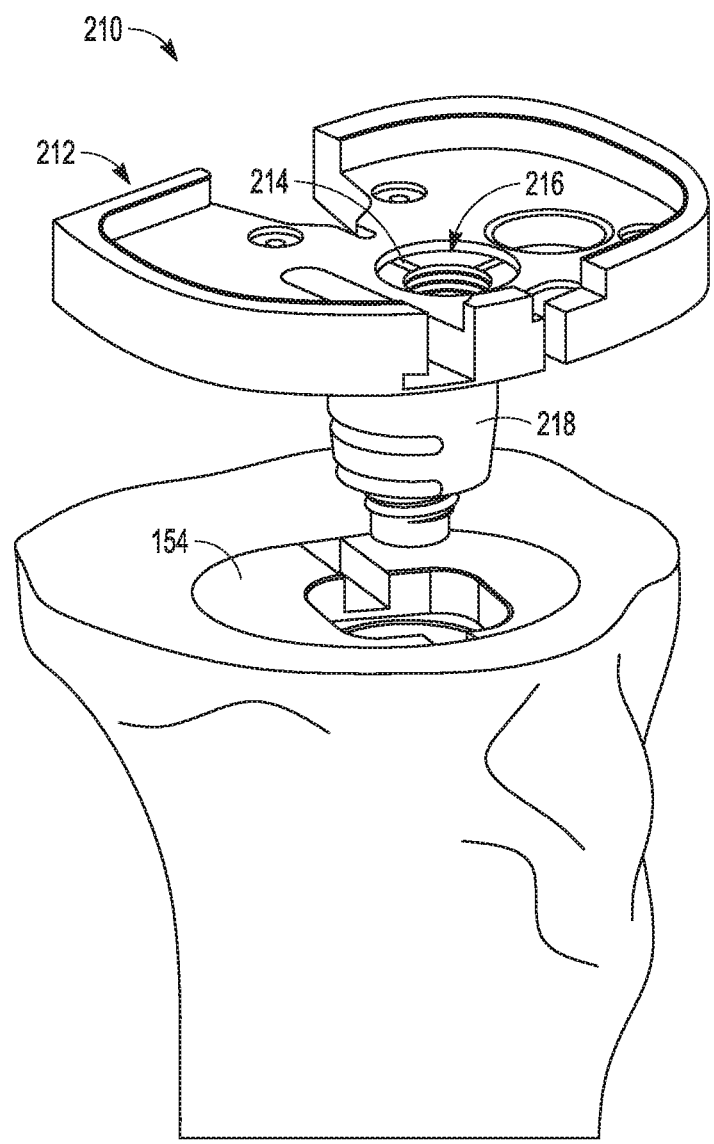
FIG. 15 shows a perspective view of a proximal end portion of the tibia with a resected surface and recess, the second provisional component positioned in the recess and a tibial tray provisional component and fastener configured to couple with the second provisional component in accordance with an example of the present application.
Figure 18:
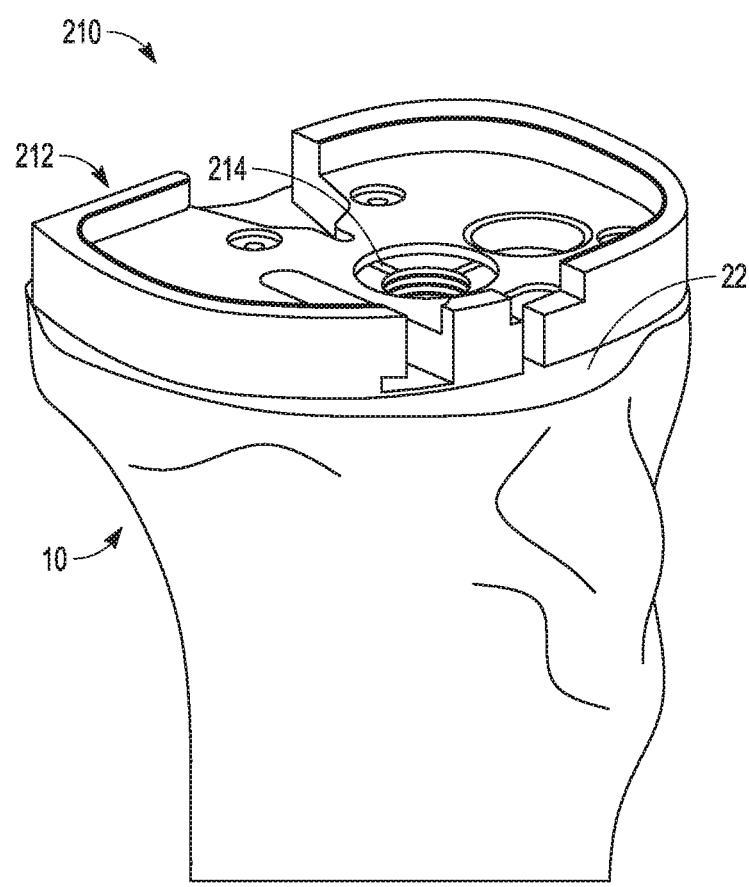
FIG. 18 shows the part of the provisional tibial assembly of FIG. 17 upon coupling of the tibial tray provisional component and the second provisional component with the fastener in accordance with an example of the present application.

FIG. 15 shows an exploded view of a portion of an assembly 210 that can include a tibial tray provisional component 212, a fastener 214, the second provisional component 154 and the stem provisional assembly 124 (e.g., FIGS. 11A-11E). FIG. 18 shows the assembly 210 with the tibial tray provisional component 212 mounted atop the proximal surface 22 of the tibia 10. In FIG. 18, the fastener 214 can be threaded to engage with the stem provisional assembly 124 (e.g., FIGS. 11A-11E) to couple together the tibial tray provisional component 212, the second provisional component 154 (FIG. 15) and the stem provisional assembly 124 (e.g., FIGS. 11A-11E).

FIG. 15 shows the tibial tray provisional component 212 and the fastener 214 disassembled from the second provisional component 154. The tibial tray provisional component can have an aperture 216 configured to receive the fastener 214 and can have a distal extending projection 218 that is configured to couple with the second provisional component 154 in a manner shown subsequently in reference to FIG. 19.

Figure 16:
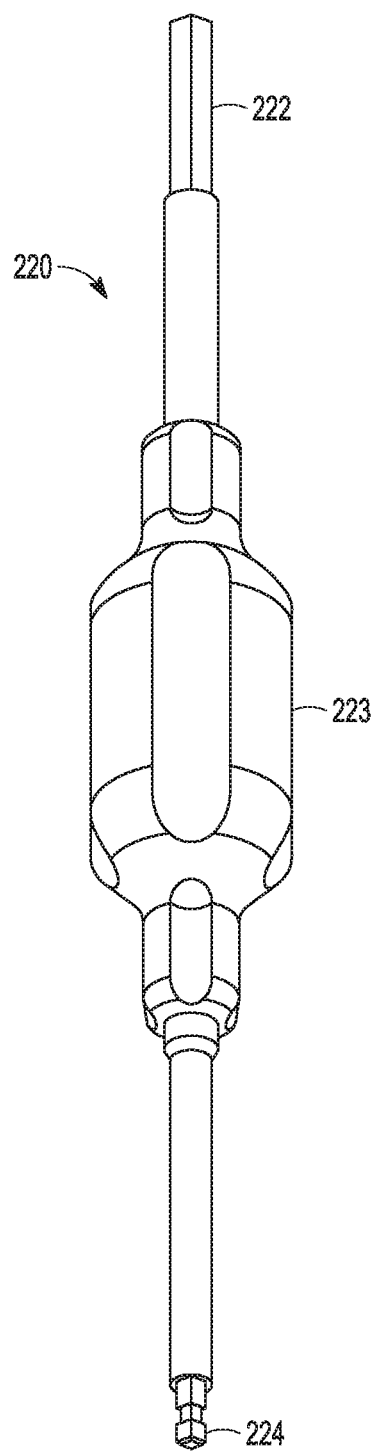
FIG. 16 shows a perspective view of a driver tool in accordance with an example of the present application.

FIG. 16 shows a driver 220 that can be configured to engage with various components of the assembly 210 (FIGS. 15 and 18) including the fastener 214 and the stem provisional assembly 124 (e.g., FIGS. 11A-11E). The driver 220 includes a first head 222, a handle 223 and a second head 224.

Figure 17:
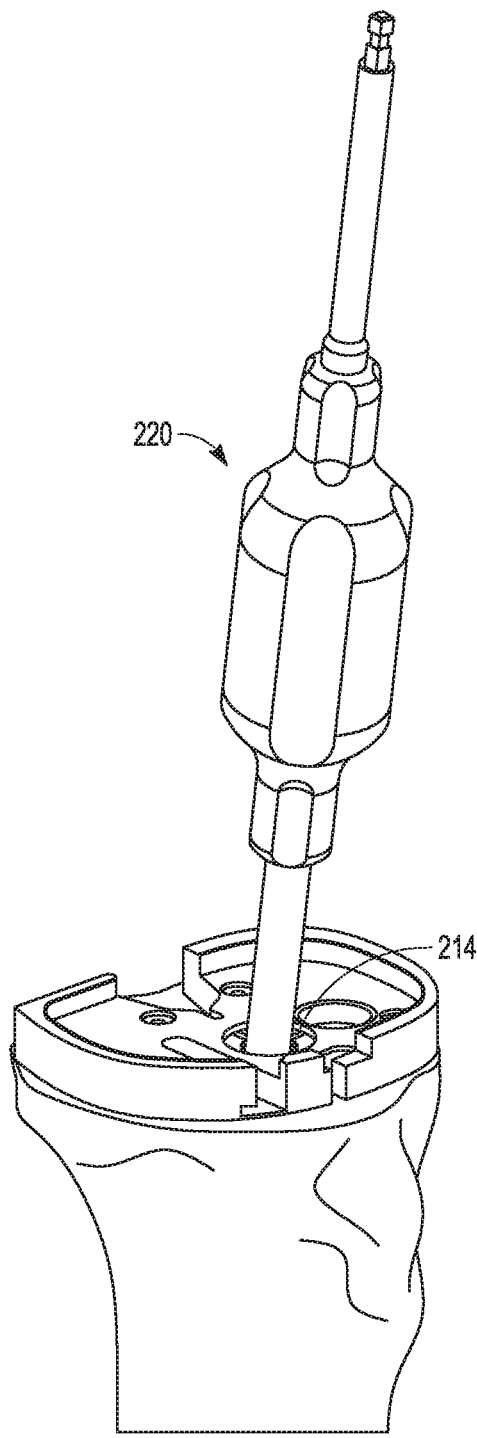
FIG. 17 shows the driver tool of FIG. 16 inserted in and engaging the fastener of FIG. 15 to engage the fastener to couple the second provisional component to the tibial tray provisional component thereby form part of a provisional tibial assembly in accordance with an example of the present application.

The driver 220 first head 222 can be configured to couple with and engage the fastener 214 to actuate the fastener 214 to rotate and thread to engage with the adaptor 128 (e.g., FIGS. 11A-11E) to thread the fastener 214 with the adaptor 128 as shown in FIG. 17. The second head 224 can be disposed opposite the first head 222 from the handle 223 and can be differently sized from the first head 222. More particularly, the second head 224 can be smaller than the first head 222 so as to configured to access portions of the adaptor 128 distal of those portions engaged by the first head 222 as will be discussed and illustrated subsequently in reference to FIG. 19.

Figure 19:
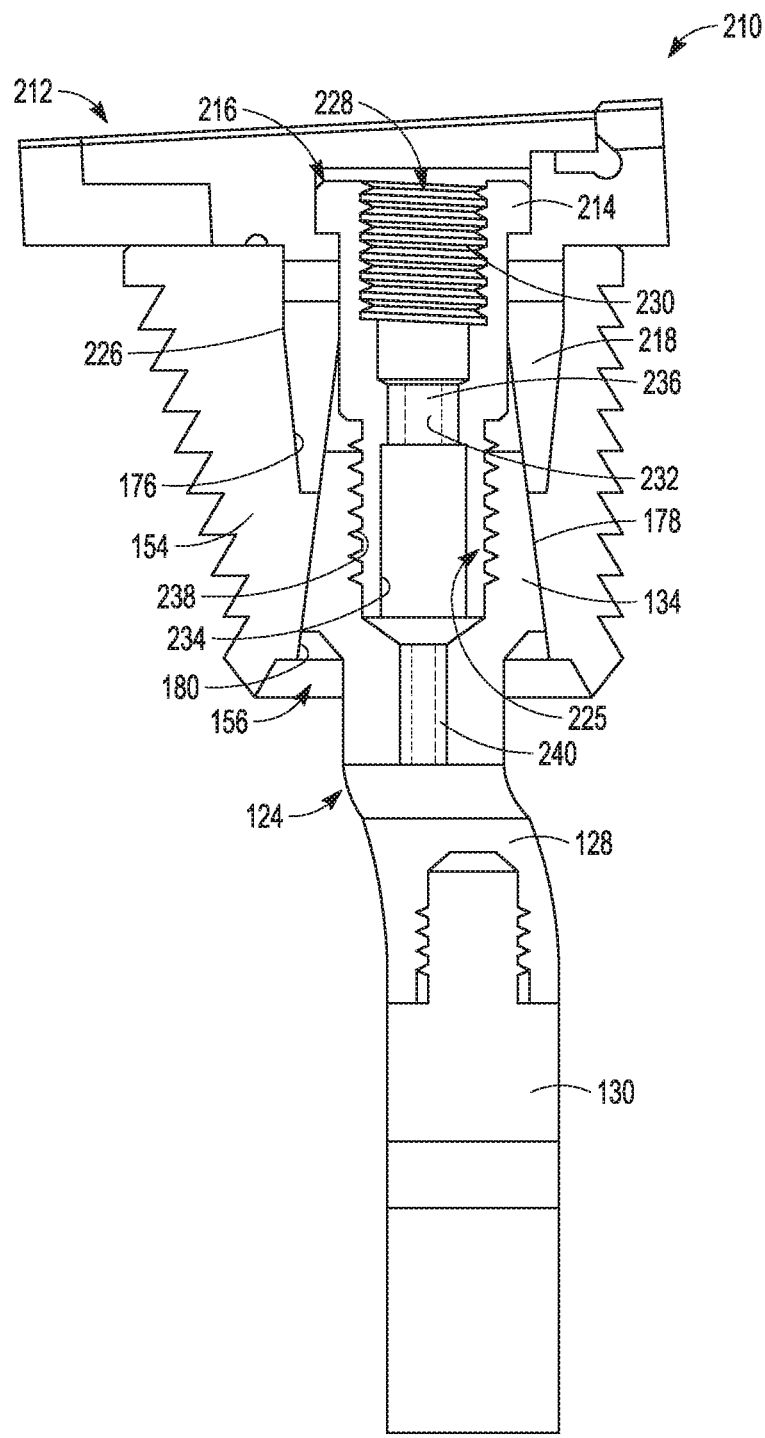
FIG. 19 shows a cross-sectional view of the entire provisional tibial assembly including the part of the provisional tibial assembly shown in FIGS. 17 and 18, the entire provisional tibial assembly including the tibial tray provisional component, the fastener and further including the second provisional component and the stem provisional assembly in accordance with an example of the present application.

FIG. 19 shows a cross-sectional view of the assembly 210 that can include the tibial tray provisional component 212, the fastener 214, the second provisional component 154 and the stem provisional assembly 124 as previously, illustrated and described. The stem provisional assembly 124 can include the adaptor 128 and the stem extension 130. A similar assembly but for the femur is shown in reference to FIGS. 26 and 26A.

As shown in FIG. 19, the fastener 214 can extend through the aperture 216 and can be at least partially received in the distal extending projection 218 of the tibial tray provisional component 212. The fastener 214 can extend into a threaded bore 225 of the adaptor 128 and can have treading configured to couple with the treading of the treaded bore 225. The second provisional component 154 can be disposed about the distal extending projection 218 of the tibial tray provisional component 212. The proximal portion 134 of the adaptor 128 can be received in the recess 156 of the second provisional component 154. The adaptor 128 and stem extension 130 can extend distal of the tibial tray provisional component 212 and the second provisional component 154. The adaptor 128 can be configured to provide the offset along a longitudinal length thereof as previously described in reference to FIGS. 8B and 8C.

The fastener 214 can thread to couple with the proximal portion 134 of the adaptor 128 in the threaded bore 225. The distal extending projection 218 of the tibial tray provisional component 212 can have an outer tapered surface 226 that is tapered in a manner to interface and seat against the first tapered inner surface 176 that forms part of the recess 156 of the second provisional component 154 when the fastener 214 is threaded to secure with the adaptor 128. Additionally, the adaptor 128 can include the tapered outer surface 178 configured to interface and seat against the second tapered inner surface 180 that forms part of the recess 156 of the second provisional component 154 when the fastener 214 is threaded to secure with the adaptor 128. The tapers utilized by one or more of the distal extending projection 218, the second provisional component 154 and the stem provisional assembly 124 can be self-holding (e.g., a Morse taper or the like) according to some examples. According to other examples, the tapers utilized by the distal extending projection 218, the second provisional component 154 and the stem provisional assembly 124 can be self-releasing.

As shown in FIG. 19, the fastener 214 can include a passage 228 therein. The passage 228 can extend the entire longitudinal length of the fastener 214 and can comprise a through hole and can be defined by a proximal portion 230, a central portion 232 and a distal portion 234. The central portion 232 of the fastener 214 that defines the passage 228 can comprise a first engagement feature 236. The proximal portion 232 can be threaded along the passage 228 (thus can have an internal thread) for coupling with a second fastener to lock down a tibial bearing component (not shown). The distal portion 234 can include an external thread 238 configured for coupling with the threaded bore 225.

The first engagement feature 236 can be configured to engaged by the first head 222 of the driver 220 (FIG. 16). Such engagement can a facilitate rotation of the fastener 214 to couple or decouple the fastener 214 from the adaptor 128 via the thread connection.

Figure 22A:
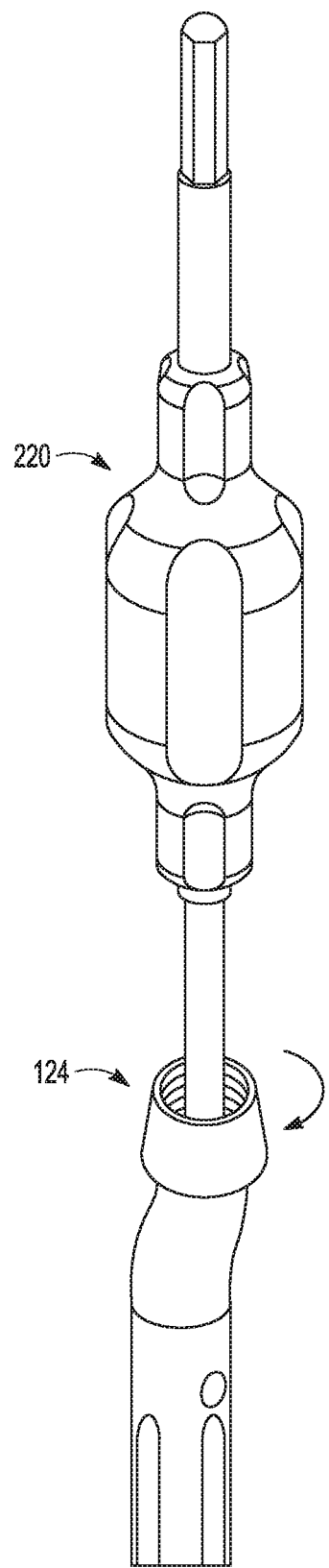
FIGS. 22A and 22B show a process of positioning of the stem provisional assembly with the driver tool, the tibial tray provisional component and the second provisional component not shown to further illustrate engagement between the driver and the stem provisional assembly in accordance with an example of the present application.
Figure 22B:
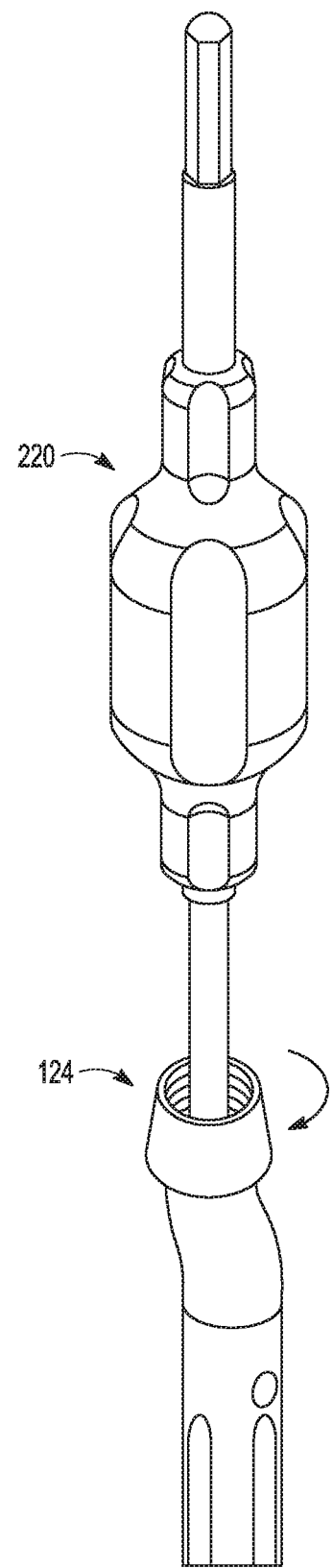
Figure 23A:
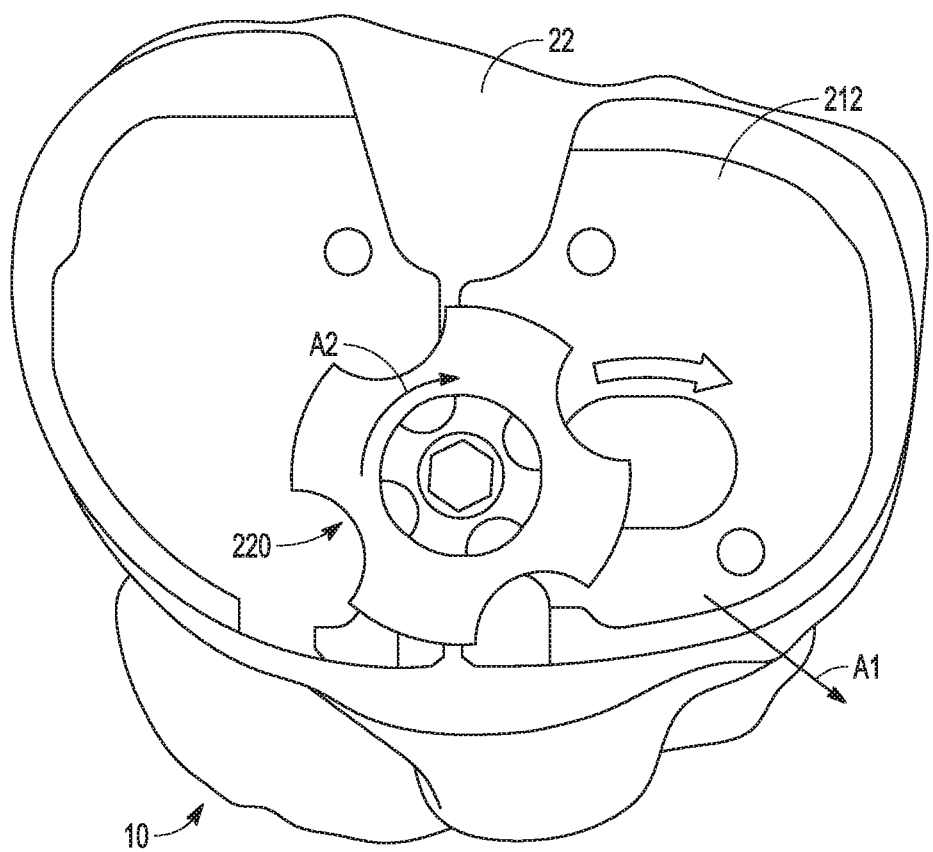
FIGS. 23A and 23B show the process of FIGS. 22A and 22B from an elevated plan view and showing the positioning process can be done in vivo and positioning of the stem provisional assembly can alter positioning of the tibial tray provisional component on a resected proximal surface of the tibia in accordance with an example of the present application.
Figure 23B:
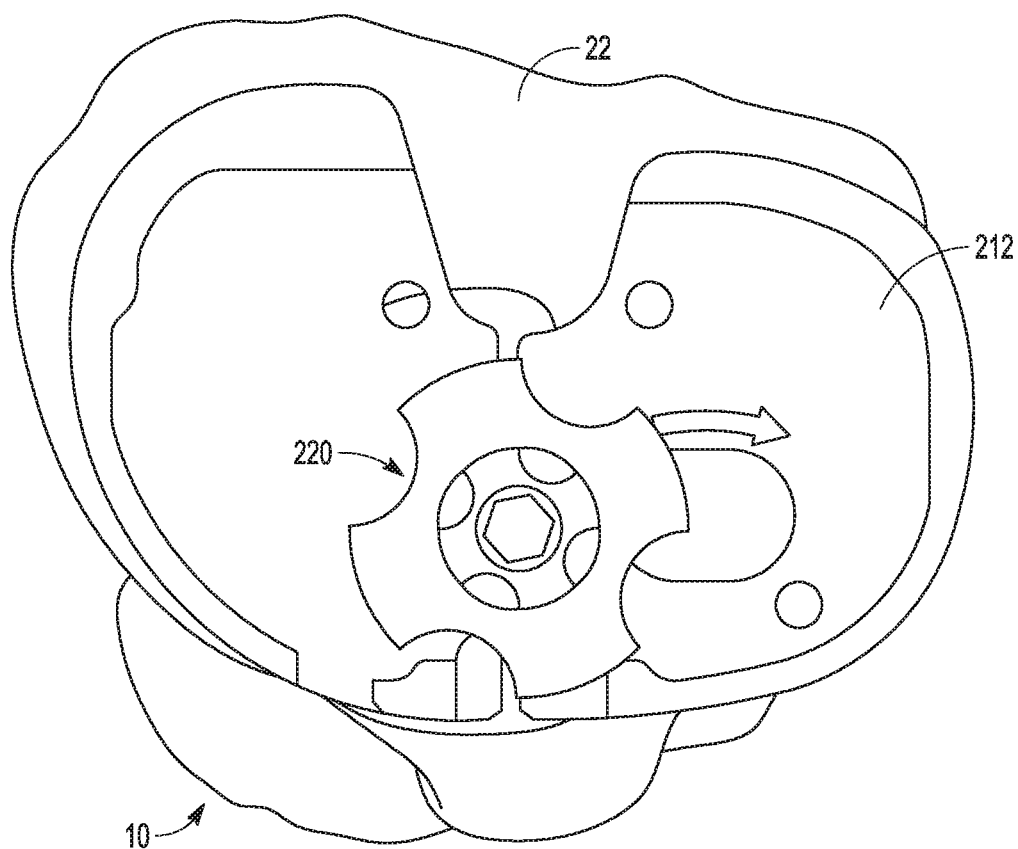
Figure 27:
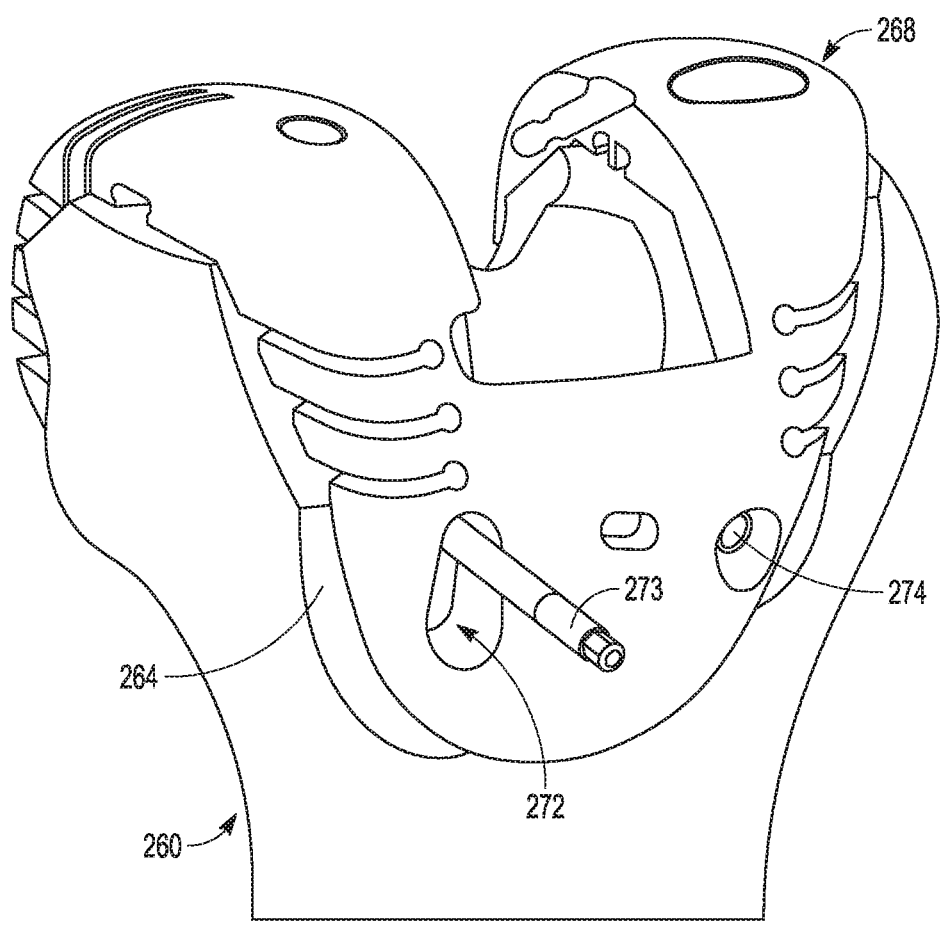
FIGS. 27 and 28 show the femoral provisional component of FIGS. 26 and 26A can include an elongated slot that allows a position of the femoral provisional component to be adjusted proximal-distal as desired relative to a distal portion of the femur in accordance with an example of the present application.
Figure 28:
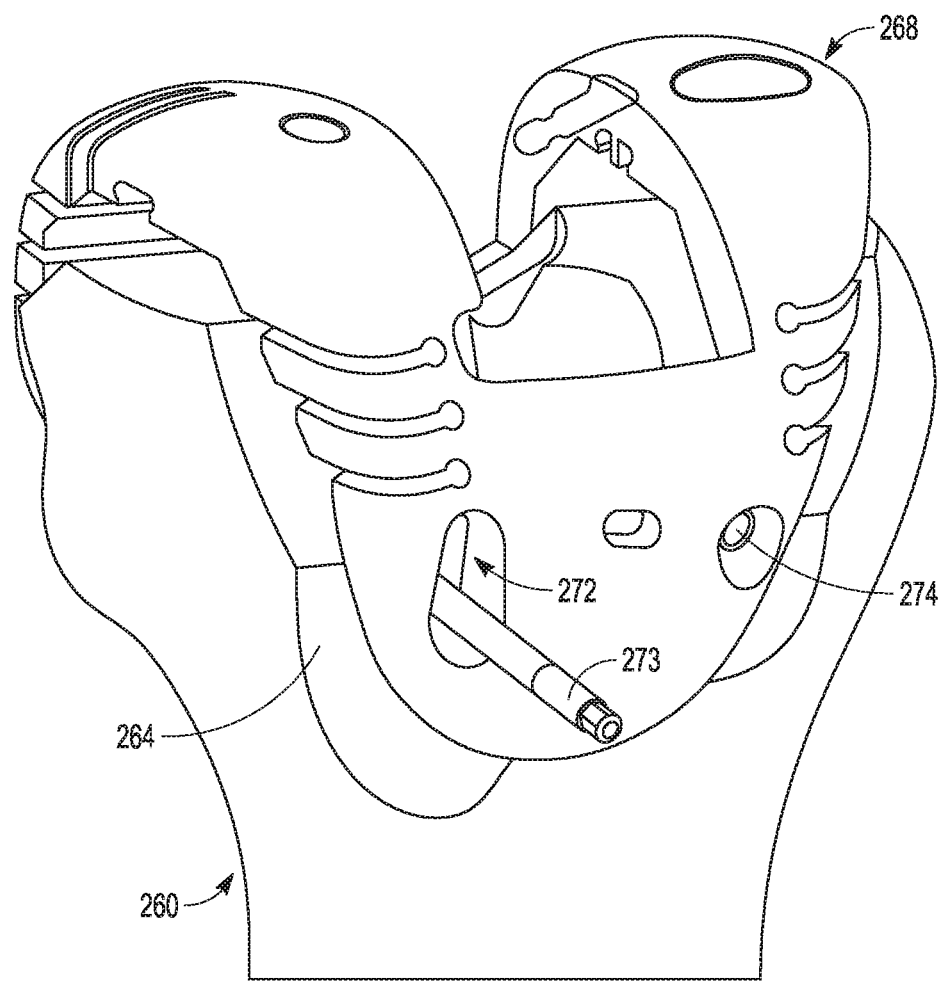

Additionally, the adaptor 128 can include a second engagement feature 240 disposed within the adaptor 128 distal of but communicating with the threaded bore 225. The second engagement feature 240 can be configured to engaged by the second head 224 of the driver 220 (FIG. 16). Such engagement can a facilitate movement of the tibial tray provisional component 212 as shown in FIGS. 23A and 23B should a change in the positioning of the tibial tray provisional component 212 be desired. This can allow the tibial tray provisional component 212 or the femoral provisional component 268 of FIG. 26A to better match the perimeter of the tibia as shown in FIGS. 23A and 23B (or femur as shown in FIGS. 27 and 28 in the case of the femoral provisional). The engagement of the stem provisional assembly 124 with the driver 220 is shown in FIGS. 22A and 22B. Such engagement can rotate the stem provisional assembly 124 in vivo, such rotation is illustrated in FIGS. 22A and 22B.

The second engagement feature 240 can be accessed by the driver 220 because a shaft and the second head 224 can be sized small enough to pass through the passage 228 including the first engagement feature 236 of the fastener 214 and the threaded bore 225 to access the second engagement feature 240. Thus, positioning of the tibial tray provisional component 212 and/or engagement to facilitate coupling or decoupling the fastener 214 from the adaptor 128 via the thread connection can be accomplished with most of the driver 220 disposed proximal of the tibial tray provisional component 212 (i.e., one of the positions shown in FIG. 17).

Positioning and/or engagement to facilitate coupling or decoupling the fastener 214 from the adaptor 128 via the thread connection is shown in reference to FIGS. 17-23B. This can be accomplished in vivo with the tibial tray provisional component 212 disposed atop the resected proximal surface 22 of the tibia 10 and the second provisional component 154 and the stem provisional assembly 124 disposed in one or more recesses as shown in FIGS. 17, 23A and 23B. In the case of the femur, the femoral provisional component 268 (FIG. 26A) can be positioned in vivo with the femoral provisional component 268 disposed atop a resected distal surface of the femur and the second provisional component 154 and the stem provisional assembly 124 disposed in one or more recesses in the femur.

It should be noted that as illustrated in FIGS. 23A and 23B, a position of the tibial tray provisional component 212 atop the resected proximal surface 22 of the tibia 10 can be altered (as indicated by arrow A1 in FIG. 23A) by actuating the driver 220 (indicated by arrow A2 in FIG. 23A) to engage and rotate the position of the stem provisional assembly 124 as shown in FIGS. 22A and 22B. This allows for a change in positioning of the tibial tray provisional component 212 on the resected proximal surface 22 and with respect to the stem provisional assembly 124 after implantation of the second provisional component 154 and the stem provisional assembly 124. Use of the driver and the stem provisional assembly 124 for adjustment of the femoral provisional component 268 (FIG. 26-28) on the femur and/or the femoral sizing cut guide 262 (FIG. 25) on the femur is also contemplated.

Figure 20:
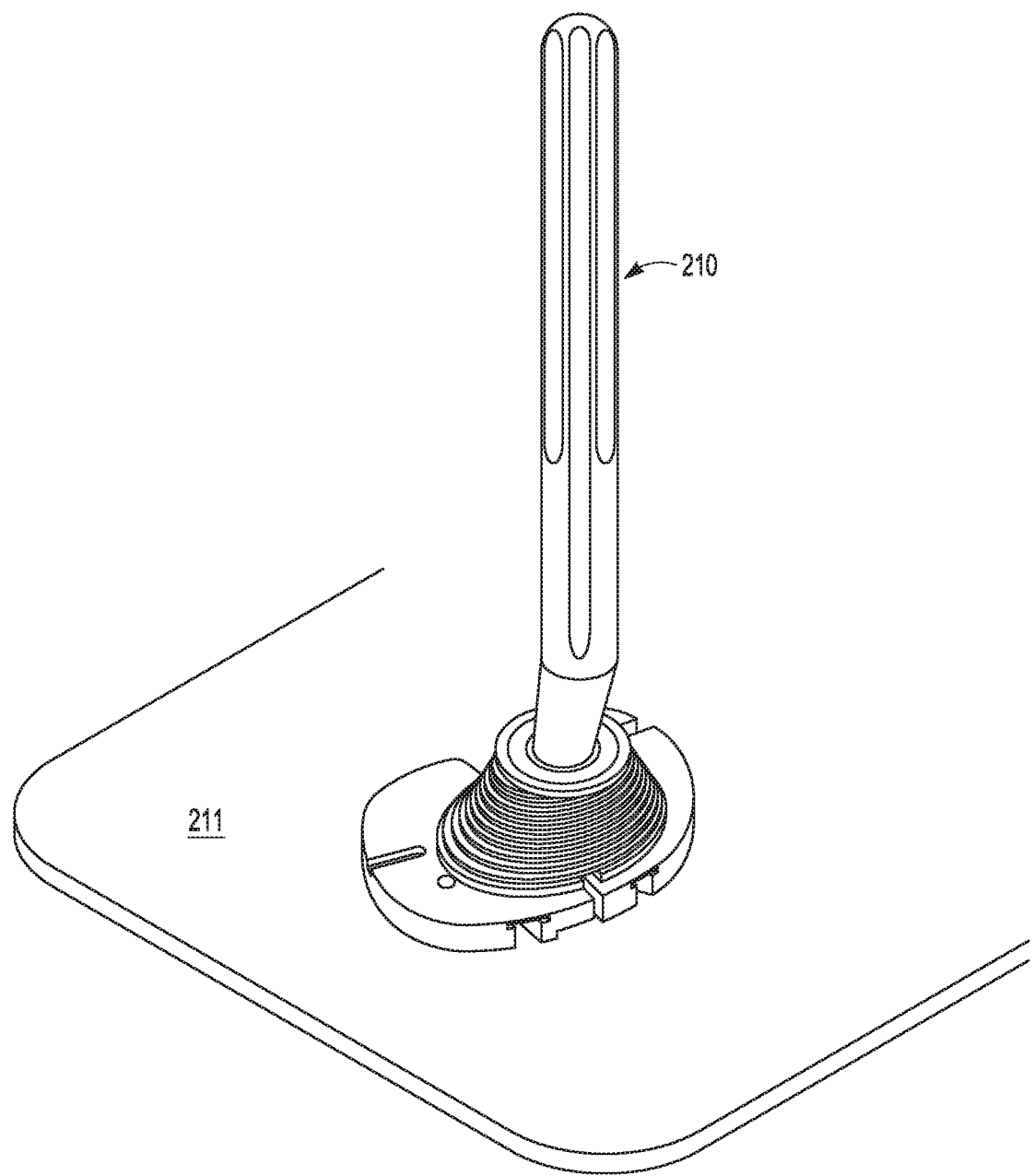
FIG. 20 shows a perspective view of the entire provisional tibial assembly removed from the tibia and placed on a work space to be used for construction of a first tibial implant assembly in accordance with an example of the present application.

FIG. 20 shows once the desired relative positions for the various components of the assembly 210 is achieved, the assembly 210 can be removed from patient together and can be placed on a work surface 211. More particularly, after being assembled and positionally adjusted in vivo the assembly 210 can then be removed from the patient with the positions of each component maintained relative to one another. This can allow permanent implants to more easily and timely be created based upon the provisional assembly as the positions of the individual provisional components need not be documented or otherwise indicated in great detail. Rather, the entire provisional assembly with relative desired positions for each part relative to the others can be maintained for easy reference.

FIG. 21 shows an alternative assembly 213 that can be assembled and positionally adjusted in vivo as previously described and then removed together and placed on the work surface 211. The example of FIG. 21 includes a second provisional component 215 designed to simulate a configuration of a keel implant.

Figure 24:
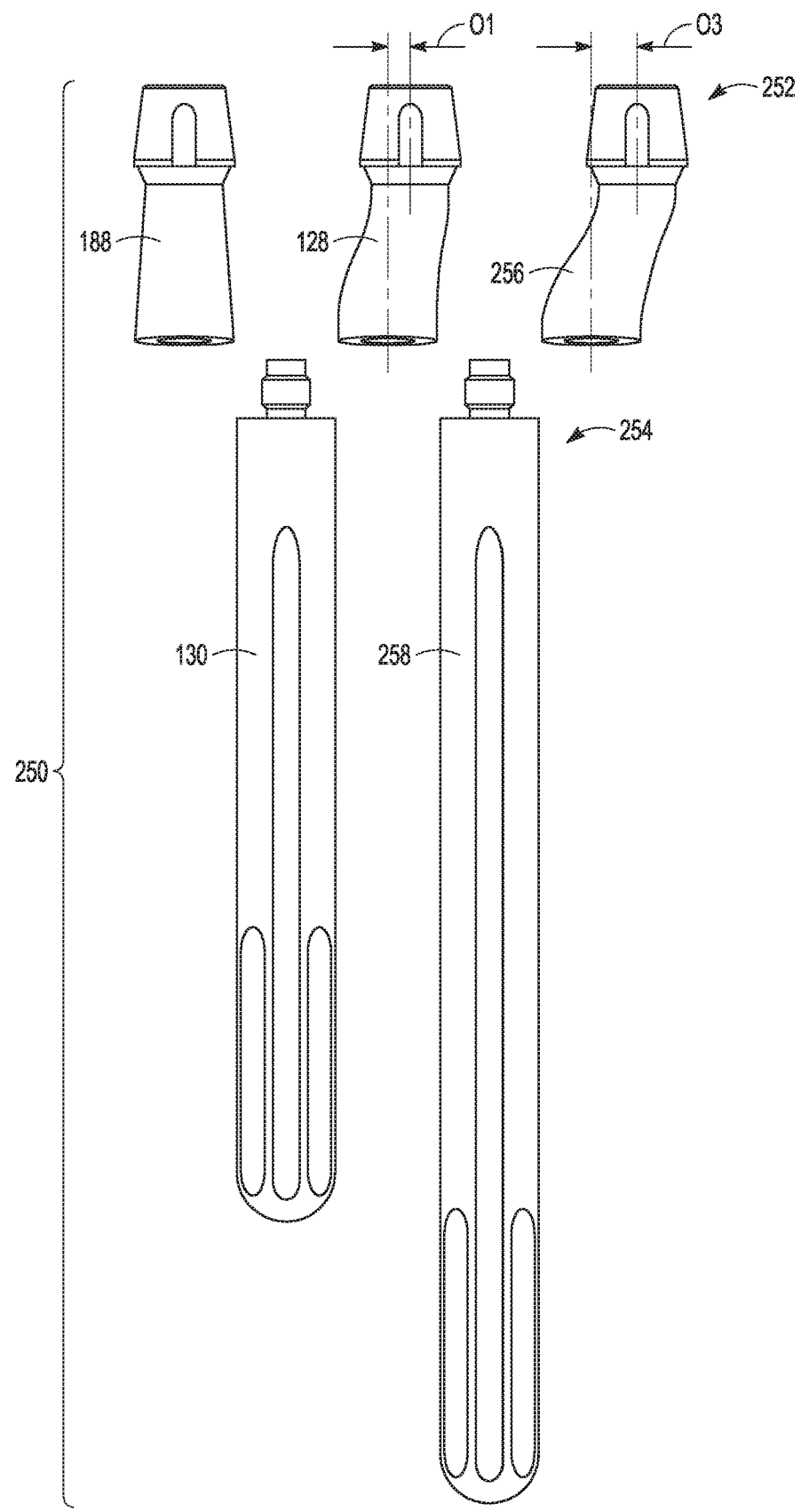
FIG. 24 shows a system that can be utilized to construct various configurations of the stem provisional assembly as desired in accordance with an example of the present application.
Figure 38:
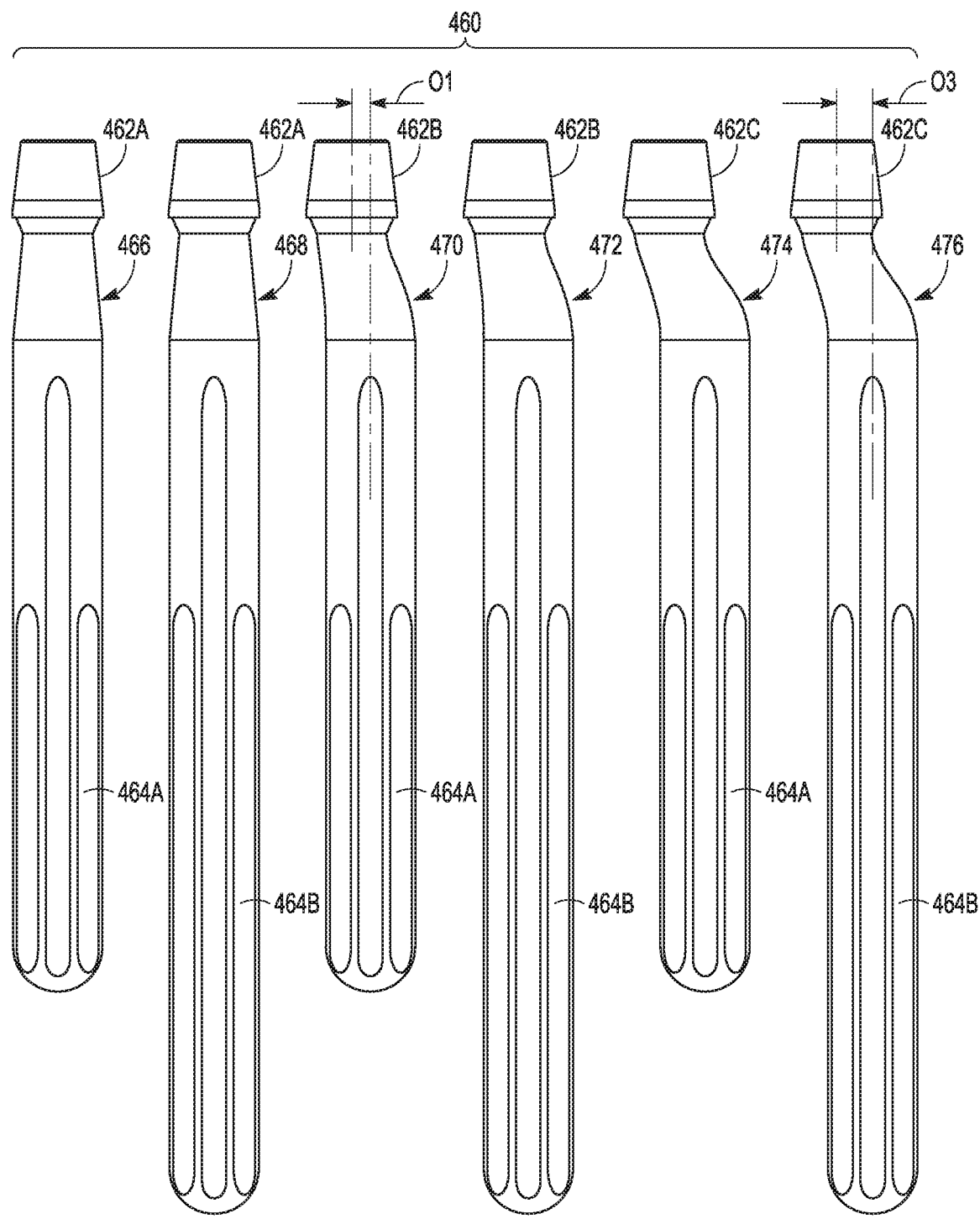
FIG. 38 shows a system of monolithic stem provisional assemblies that can be used in alternative to the system of FIG. 24 in accordance with an example of the present application.

FIG. 24 shows a system 250 of components that can be assembled to comprise the stem provisional assembly 124 or another stem provisional assembly for example. Alternatively, a system with monolithic versions of the stem provisional assembly (single piece adaptor part and stem extension part) can be provided as shown in FIG. 38.

As shown in the example of FIG. 24, the system 250 can include a plurality of adaptors 252 and a plurality of stem extensions 254. The plurality of adaptors 252 can include the first adaptor 128, the second adaptor 188 and a third adaptor 256. The plurality of stem extensions 254 can include the stem extension 130 and a second stem extension 258.

The plurality of adaptors 252 can be used interchangeably with the plurality of stem extensions 254 to provide varying amounts of offset in the longitudinal direction. For example, the adaptor 128 can provide for a first amount of offset O1. The second adaptor 188 can provide for substantially no offset. The third adaptor 256 can provide for a third amount of offset O3 that can differ from the offset O1 and the no offset provided by the first adaptor 128 and the second adaptor 188. According to one example, the first amount of offset O1 comprises 3 mm and the offset O3 comprises 6 mm.

The plurality of stem extensions 254 provide for a varying longitudinal length. For example, the stem extension 130 can have 135 mm of longitudinal length and the stem extension 258 can have 175 mm of longitudinal length. Various diameters for each of the plurality of stem extensions 254 can be provided as part of the system 250.

The system 250 can be used interchangeably as a kit with either a tibial provisional components or femoral provisional components to reduce the overall component count and thereby reduce costs and weight of the provisional systems illustrated herein. According to other examples, the system 250 may differ, for example further adaptors having different offsets can be provided. According to some examples, rather than a modular system, an integral stem provisional assembly with the stem extension and adaptor as a single component as shown in FIG. 38.

Figure 25:
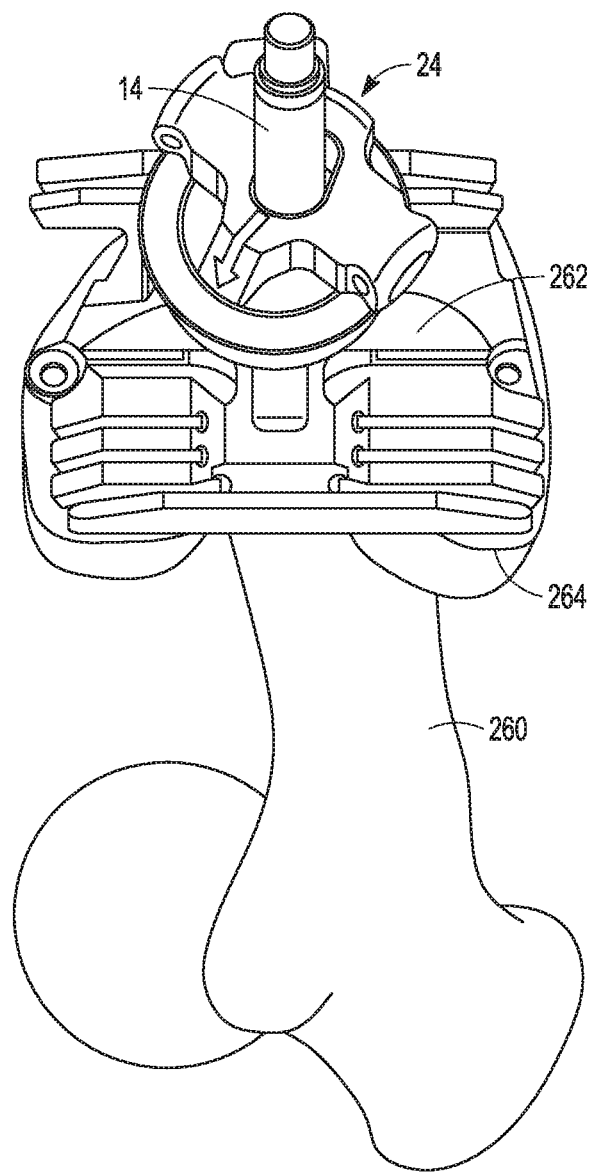
FIG. 25 shows a perspective view of a femur with a reamer inserted therein and the offset coupler assembly being used to position a cut guide on a distal end of the femur in accordance with an example of the present application.

FIG. 25 shows a femur 260 with the reamer 14, a femoral cut guide 262, and the offset coupler 24. The offset coupler 24 can have the construction previously described in reference to FIGS. 3 and 3A. It is important to note that all the instruments, components, systems, methods and techniques previously described in reference to FIGS. 1-24 can be used with and are equally applicable to the femur 260 as well as the tibia 10.

In FIG. 25, the offset coupler 24 is coupled with the reamer 14 and can couple with the femoral cut guide 262. The offset coupler 24 can be used in the manner previously described in reference to FIGS. 3 and 3A to adjust the position of the femoral cut guide 262 as desired on a distal end portion 264 of the femur 250. The femoral cut guide 262 can comprise a 4-in-1 cut guide with a plurality of slots 256 configured to guide resection of the distal end portion 264 of the femur 250 at various desired angles.

Figure 26:
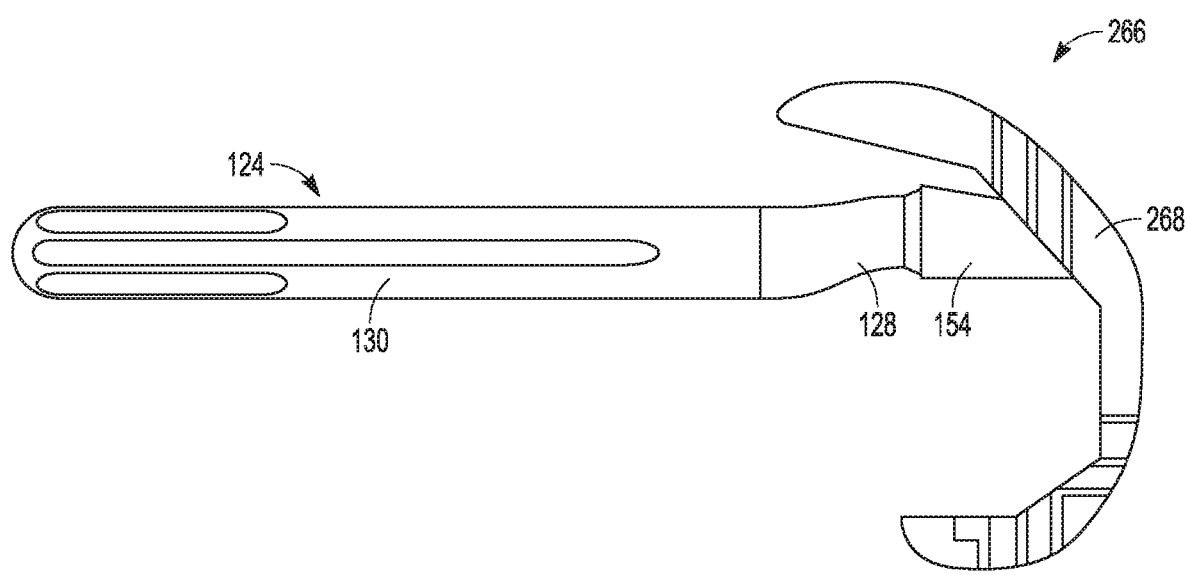
FIGS. 26 and 26A show a femoral provisional assembly that includes a femoral provisional component, the second provisional component and the stem provisional assembly in accordance with an example of the present application.
Figure 26A:
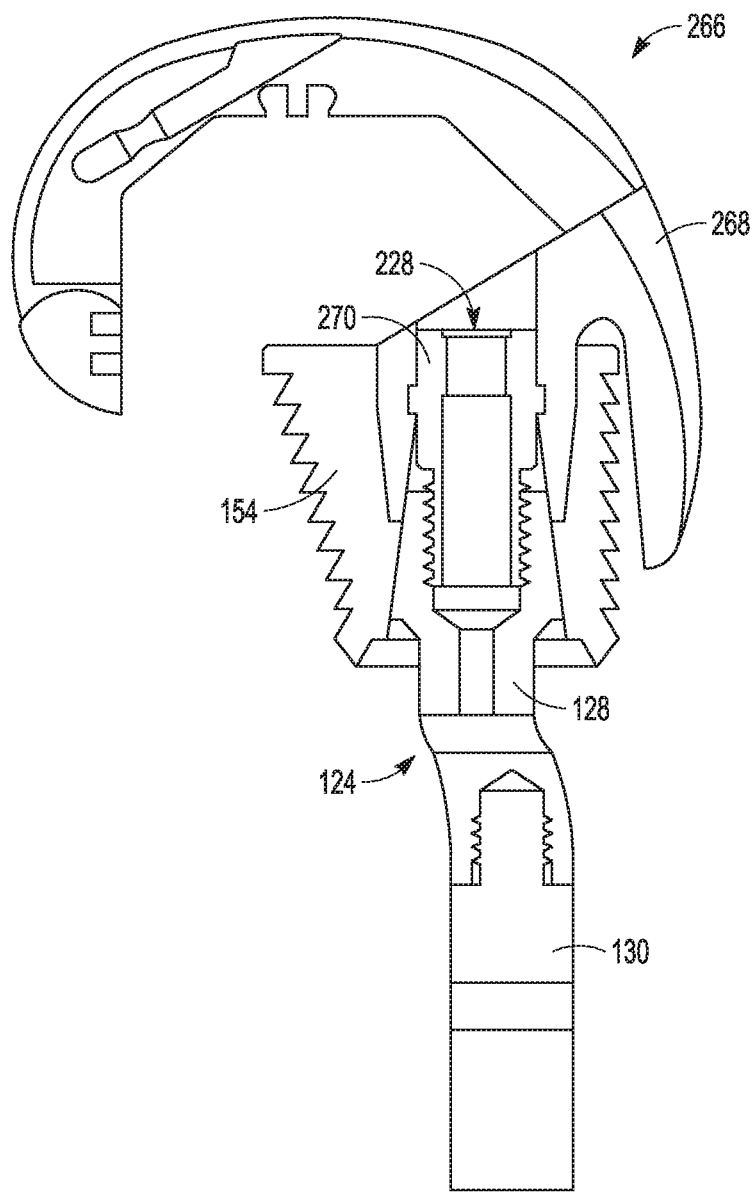

FIGS. 26 and 26A show an assembly 266 that includes a femoral provisional component 268, a fastener 270 (FIG. 26A), the second provisional component 154 and the stem provisional assembly 124 as previously illustrated and described. The stem provisional assembly 124 includes the adaptor 128 and the stem extension 130.

The fastener 270 can be configured in a manner similar to that of fastener 214 (FIG. 19) previously described but can have a longitudinal length and proximal end portion of a different configuration as no bearing component needs to be coupled to the fastener 262. The fastener 262 can include the passage 228 to provide access to the adaptor 128 to provide for adjustment of the positioning of the stem provisional assembly 124 in the manner previously described.

As shown in FIGS. 27 and 28, according to some examples the femoral provisional component 268 can include an elongated slot 272. This elongated slot 272 can be configured to receive a pin 273 therein. The elongated slot 272 can be positioned to allow for proximal-distal adjustment of the femoral provisional component 268 on the end portion 264 of the femur 260 as illustrated in FIGS. 26 and 27. More particularly, with the pin 273 in place and received in the elongated slot 272, medial-lateral movement and internal-external rotation of the femoral provisional component 268 can be constrained. However, adjustment of the proximal-distal position of the femoral provisional component 268 due to the shape and orientation of the slot 272 can be possible. When a desired location for the femoral provisional component 268 is achieved, a second pin (not shown) can be passed through aperture 274 into the femur 260. This can hold the femoral provisional component 268 in a desired position.

The femoral provisional component 268 can include various slots for making augment cuts and can include an intercondylar recess configured to couple with an insert to perform a box cut if desired.

FIGS. 29-32 show stem extension implants that are configured to be insensitivity to stem rotation angle. This can allow the stem extension implants to flex in any direction. In contrast, to prior known slotted stem implants are configured to be direction sensitive, and therefore, only allow for flexing of the implant in a limited number of direction(s).

Figure 29:
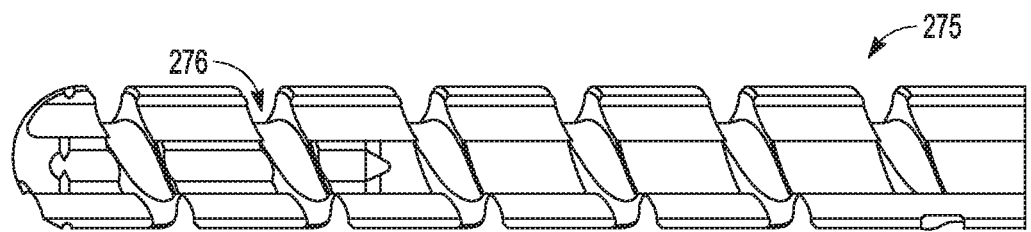
FIGS. 29-32 show various alternative configurations for stem extensions that can be used with the stem provisional assembly in accordance with examples of the present application.

FIG. 29 shows an alternative design for a distal portion of a stem extension implant 275 according to one example. The stem extension implant 275 can include a spiraling passage 276 along a portion of the longitudinal length thereof. Such a configuration can provide additional flexibility to the stem extension implant 275 if desired that is not dependent on a certain rotational placement in the bone.

Figure 30:
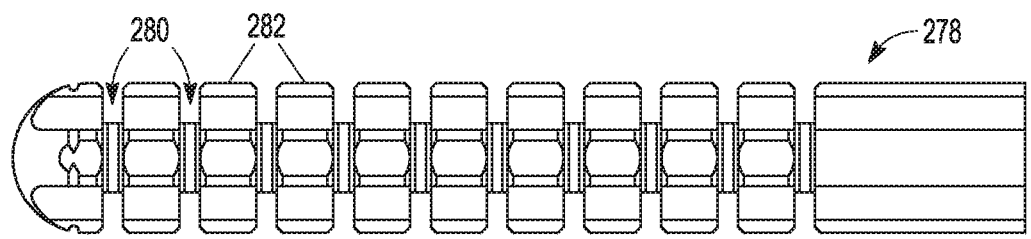

FIG. 30 shows another alternative design for a distal portion of a stem extension implant 278. The stem extension implant 278 can include a plurality of gaps 280 spaced from one another along a portion of the longitudinal length of the stem extension implant 278. These plurality of gaps 280 create spaced apart segments 282 having a cross-sectional area that differs from that of a cross-sectional area taken through the plurality of gaps 280. Such a configuration can provide additional flexibility to the stem extension implant 278 if desired that is not dependent on a certain rotational placement in the bone.

Figure 31:
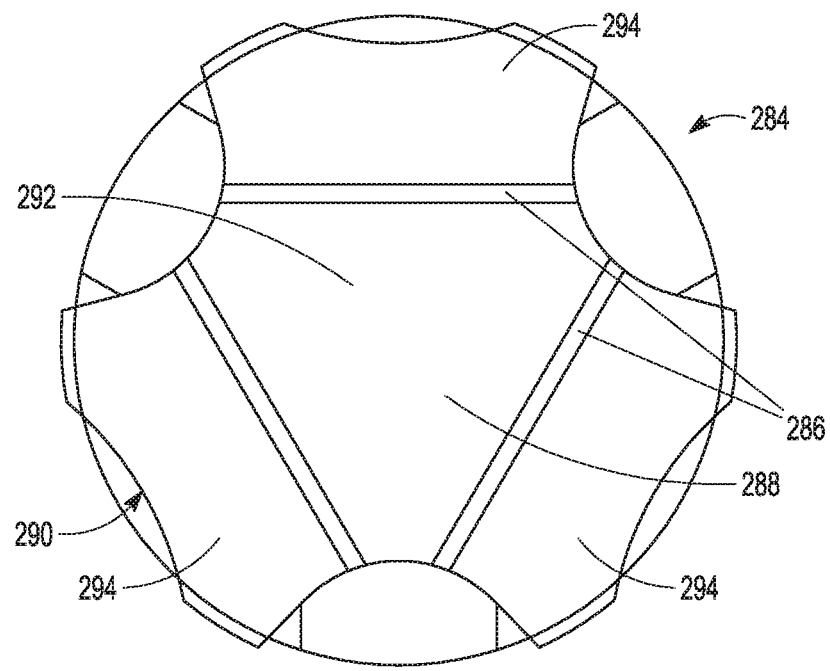
Figure 32:
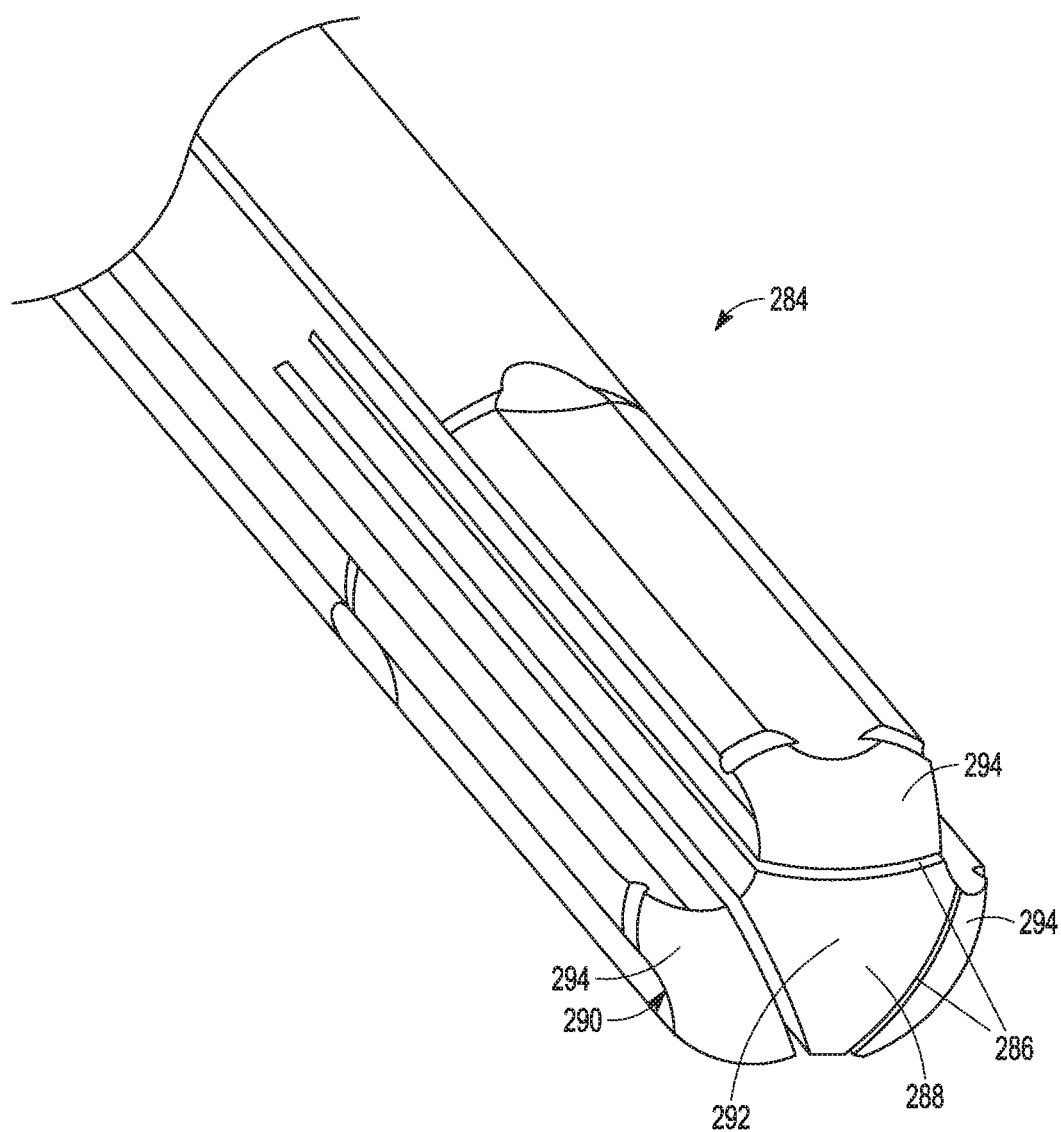

FIGS. 31 and 32 show yet another alternative design for a distal portion of a stem extension implant 284. The stem extension implant 284 can include a plurality of slots 286 therein. These slots 286 can extend a portion of the longitudinal length of the stem extension implant 284 and can extend to a distal tip 288 thereof. The plurality of slots 286 can separate the stem extension implant 284 into a plurality of sections 290 including a central section 292 and a plurality of outer sections 294. Such a configuration can provide additional flexibility to the stem extension implant 284 if desired, while providing increased bending stiffness through contact of 294 with the central core (288 or 292).

It should be noted that rather than having three slots 286 as shown according to other embodiments more or less slots can be provided. For example, rather than central section 292 having a generally triangular shaped when viewed in a cross-section perpendicular to the longitudinal axis L due to three slots 286 being utilized, the central section can have a generally square shape if four slots are utilized.

Figure 33:
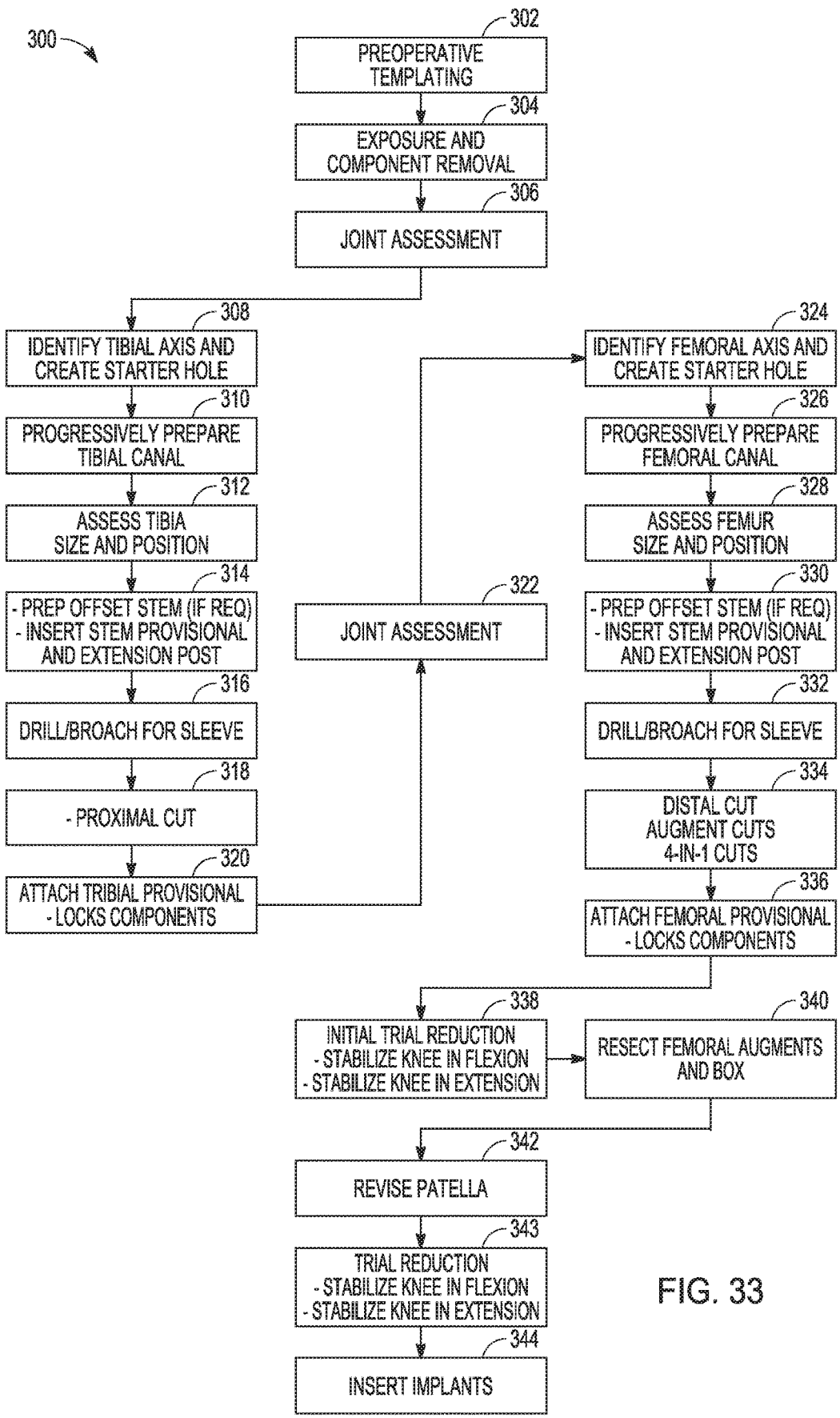
FIG. 33 show a method for a revision knee arthroplasty in accordance with an example of the present application.

FIG. 33 shows a method 300 according to one example. The method 300 can utilized the systems, instruments and components previously described in reference to FIGS. 1-32. According to one example the method 300 can include a preoperative step. This can include imaging the knee joint using a medical imaging technique, such as a computed tomography (CT scan), x-ray or a magnetic resonance imaging (MRI), to obtain imaging data representing the knee joint. Imaging data can be obtained or gathered during a pre-operative planning stage based on two or three-dimensional computer images of the corresponding anatomy reconstructed from image scans of the patient by computer imaging methods according to some examples. Such imaging can be used to identify diseased bone and or tissue of one in the tibia and/or femur that would require removal as well as implants requiring removal in the case of a revision. The imaging can also be used to identify one or more axes of the knee joint such as the mechanical or anatomic axes of the tibia and femur. A model of the joint can be present to the surgeon as part of the preoperative plan. The surgeon can review the three-dimensional model and can provide direction via electronic input in some examples.

In step 304, the joint can be exposed and one or more existing implants can be removed. A preliminary joint assessment 306 can also be carried out. A tibial joint revision stage of the method 300 can then be implemented. The surgeon can identify 308 the tibial mechanical axis based on image data and/or observation and experience. A starter hole may also be created. The tibial canal (e.g., intramedullary canal, diaphysis and/or metaphysis can be prepared 310 using the reamer 14 previously illustrated and discussed, for example. An assessment of tibia size and position 312 can be occur. If an offset stem provisional assembly is desired, this or another stem provisional assembly can be prepared and inserted 314 into the one or more recesses in the tibia. Any desired drilling, broaching or reaming can be carried out 316 using the instruments and/or techniques discussed in reference to FIGS. 5-10E, for example. A resection of the proximal tibia can be performed 318 using the instruments and/or techniques of FIGS. 13-14B, for example. A tibial tray provisional component can be attached 320 and assembly can occur as discussed in reference to FIGS. 15-23B. A joint assessment 322 can be carried out. In some examples, the tibia assembly can be removed for the creating of an implant assembly as discussed in reference to FIGS. 20 and 21.

A femoral joint revision stage of the method 300 can then be implemented. The surgeon can identify 324 the femoral mechanical and/or anatomic axis based on image data and/or observation and experience. A starter hole may also be created. The femoral canal (e.g., intramedullary canal, diaphysis and/or metaphysis can be prepared 326 using the reamer 14 previously illustrated and discussed, for example. An assessment of femur size and position 328 can be occur. If an offset stem provisional assembly is desired, this or another stem provisional assembly can be prepared and inserted 330 into the one or more recesses in the tibia. Any desired drilling, broaching or reaming can be carried out 332 using the instruments and/or techniques discussed in reference to FIGS. 5-10E, for example. A resection of the distal femur can be performed 334 using the instruments and/or techniques of FIGS. 25-28, for example. A femoral provisional component can be attached 336 and assembly can occur as discussed in reference to FIGS. 15-28.

The method 300 can further include an initial trialing and reduction 338 and resection for femoral augments and the performance of a box resection 340. The method 300 can also include a revision of the patella 342 and final trialing stage 343 where the knee can be stabilized in flexion and extension. The method 300 can conclude with insertion of one or more implants 344.

Figure 34:
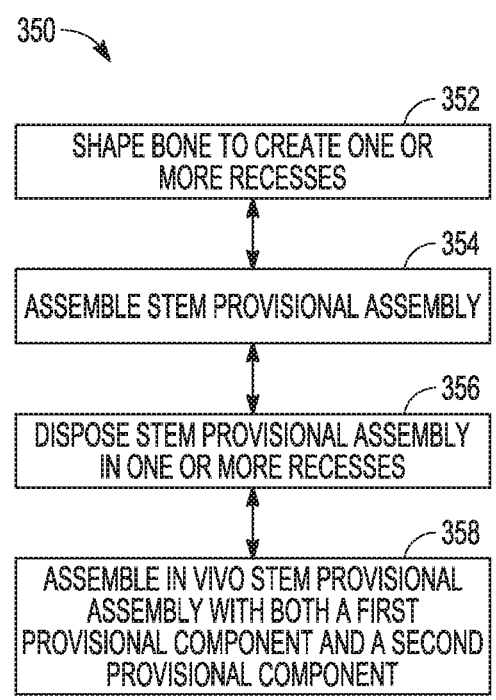
FIG. 34 shows a method that can be used as part of the method of FIG. 33 in accordance with an example of the present application.

FIG. 34 shows further details of another method 350 that can be used as part of the method 300 of FIG. 33. The method 350 can include shaping 352 a bone of a patient to create one or more recesses therein. The method 350 can include assembling 354 a stem provisional assembly comprising an adaptor and a stem extension and disposing 356 the stem provisional assembly within the one or more recesses. The method 350 can also include assembling 358 in vivo the stem provisional assembly with both a first provisional component configured to simulate a shape of one of a tibial tray implant or a femoral implant and a second provisional component configured to simulate a shape of at least one of a sleeve component or a keel component of an implant. In some examples, this assembling can include selecting the adaptor from a plurality of adaptors each of the plurality of adaptors having a longitudinal axis extending between a proximal end and a distal end, wherein the plurality of adaptors include at least a first adaptor with no offset of the longitudinal axis and at least a second adaptor with some amount of offset of the longitudinal axis, and selecting the stem extension from a plurality of stem extensions each configured to couple with the plurality of adaptors, wherein the plurality of stem extensions each have a different longitudinal extent between a proximal end and a distal end. In further examples, this assembling can include one or more of engaging a fastener to thread the fastener into a threaded recess of the stem provisional assembly, and passing a tool through a passage in the fastener to engage the stem provisional assembly distal of the threaded recess The method 350 can additionally include temporarily coupling the second provisional component and the stem provisional assembly together with a handle configured to insert over a post extension, and inserting the stem provisional assembly and the second provisional component together into the one or more recesses. The method 350 can include identifying an axis of the bone, and determining if an offset construct for the stem provisional assembly is desirable according to one example. The method 350 can include moving the stem provisional assembly in vivo to position the stem provisional assembly in a desired location in the one or more recesses and to position the first provisional component on a resected surface of the bone according to one example. The method 350 can include removing at least the tibial tray provisional component, the second provisional component and the stem provisional assembly together from the bone and the one or more recesses with the positions of each maintained relative to one another according to one example. Additionally, the method 350 can include constructing an implant assembly based upon the positions of the tibial tray provisional component, the second provisional component and the stem provisional assembly.

Figure 35A:
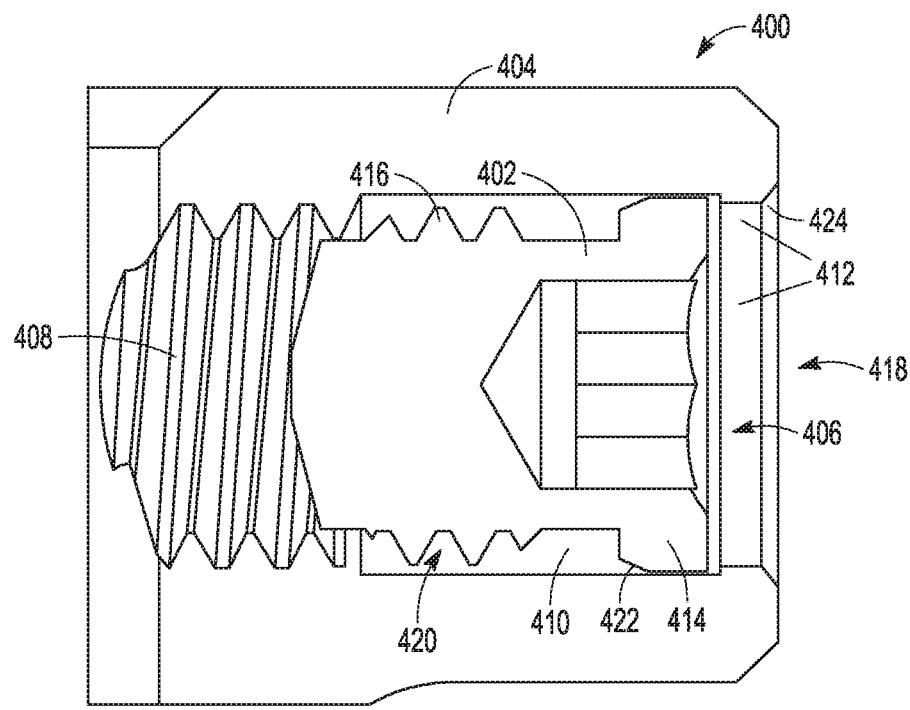
FIGS. 35A and 35B show cross-sections of an assembly of a fastener with a component, the component having a pocket and restriction for retaining the fastener such that it can be non-removable from the component once received in the pocket in accordance with an example of the present application.
Figure 35B:
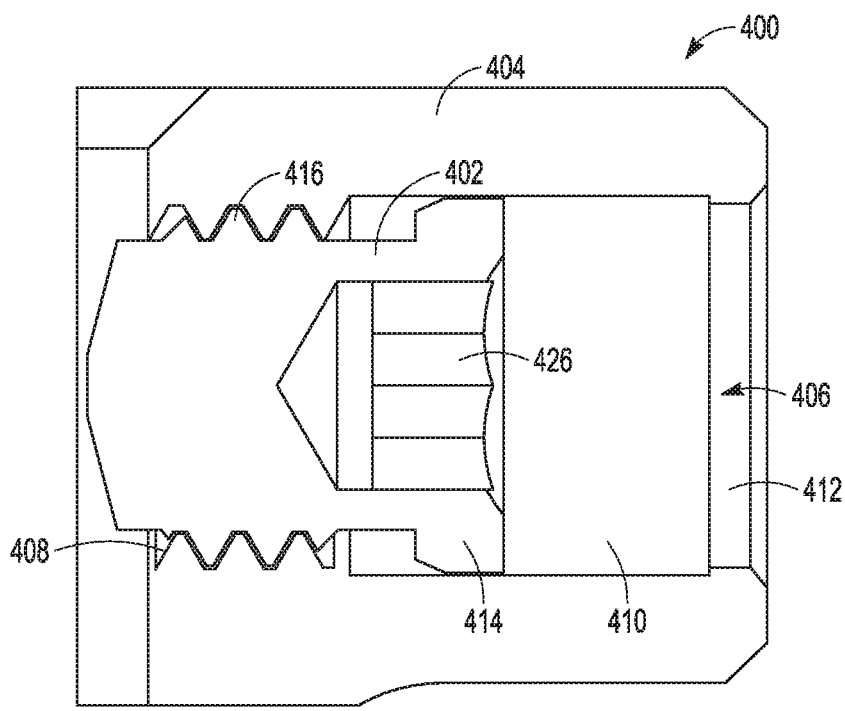

FIGS. 35A and 35B show an assembly 400 of a set screw 402, a fastener 402 and a component 404. The component 404 can comprise practically any orthopedic instrument or device and can include the instruments and devices described herein, such as the drill guide 140 (FIGS. 9A and 9B), the offset coupler 24 and the femoral cut guide 262 of FIG. 25, for example.

According to the example of FIGS. 35A and 35B, the component can include a bore 406 with a thread portion 408, a pocket portion 410 and a restriction 412. The fastener 402 can comprise a set screw with a head portion 414 and a thread portion 416.

The bore 406 can be configured such that the thread portion 408 is disposed adjacent and communicates with the pocket portion 410 and the pocket portion 410 is disposed adjacent and communicates with the restriction 412. The restriction 412 can be disposed at or closely adjacent an opening 418 to the bore 406 according to some examples. However, this arrangement is not the case in other examples. The thread portion 416 of the fastener 402 can connect with the head portion 414.

As shown in FIG. 35A, the fastener 402 can be disengaged from the component 404 such that the thread portion 408 is not coupled with the thread portion 416. Thus, the fastener 402 including the thread portion 416 and the head portion 414 can reside in the pocket portion 410 with some space 420 thereabout. More particularly, the pocket portion 410 can be sized to receive the fastener 402 therein allowing for the space 420 between a sidewall of the pocket portion 410 and parts of the surface of the fastener 402 that form the head portion 414 and the thread portion 416. This space 420 can allow sterilizing solution access to the thread portion 408, the pocket 410 and the fastener 402 through the opening 418 and around the head portion 414, for example.

FIG. 35A shows that the pocket portion 410 can be sized with a diameter larger than that of the head portion 414 to provide for some degree of spacing therefrom. However, the restriction 412 can have a diameter substantially equal to or somewhat smaller than that of the head portion 414. Thus, an interference fit would occur between the restriction 412 and the head portion 414. In FIG. 35A, the fastener 402 has been inserted through this interference fit into the pocket portion 410. Such insertion can be accomplished by use of flexible materials for the component and/or the fastener, application of sufficient force on the fastener 402 to accomplish insertion, application of a temperature differential between the fastener and component (to cause an expansion and/or contraction of the relative parts), for example. To facilitate such insertion the head portion 414 can include a chamfered surface 422 that can act as a ramp to facilitate insertion of the fastener 402 into the restriction 412. Additionally or alternatively, the restriction 412 can include a chamfered surface 424 that can act as a ramp. In an example where both chamfered surfaces 424 and 422 are utilized, the chamfered surface 422 can be shaped and positioned to initially interact with the chamfered surface 424 during insertion of the fastener 402 into the pocket portion 410.

Once captured in the pocket portion 410, the restriction 410 can be configured (sized) relative to the head portion 414 such that the fastener 402 cannot be backed out of the bore 406 past the restriction 412 due to the interference fit between the restriction 412 and the head portion 414. Thus, the fastener 402 can be non-removable after insertion into the pocket portion 410 and can be retained by the restriction 410.

FIG. 35B shows the fastener 402 after having been engaged at an engagement feature 426 in the head portion 414 and rotated to bring the thread portion 416 into engagement with the thread portion 408. Such thread engagement can tighten down two portions of the component 404, for example.

Figure 36A:
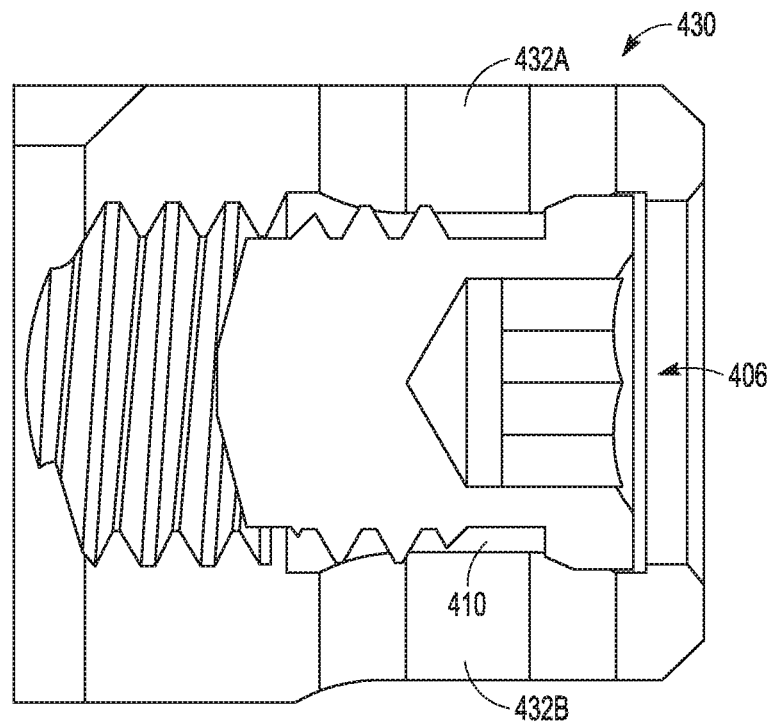
FIGS. 36A and 36B show cross-sections of another example assembly configured in a manner similar to that of FIGS. 35A and 35B but including a passageway in accordance with an example of the present application.
Figure 36B:
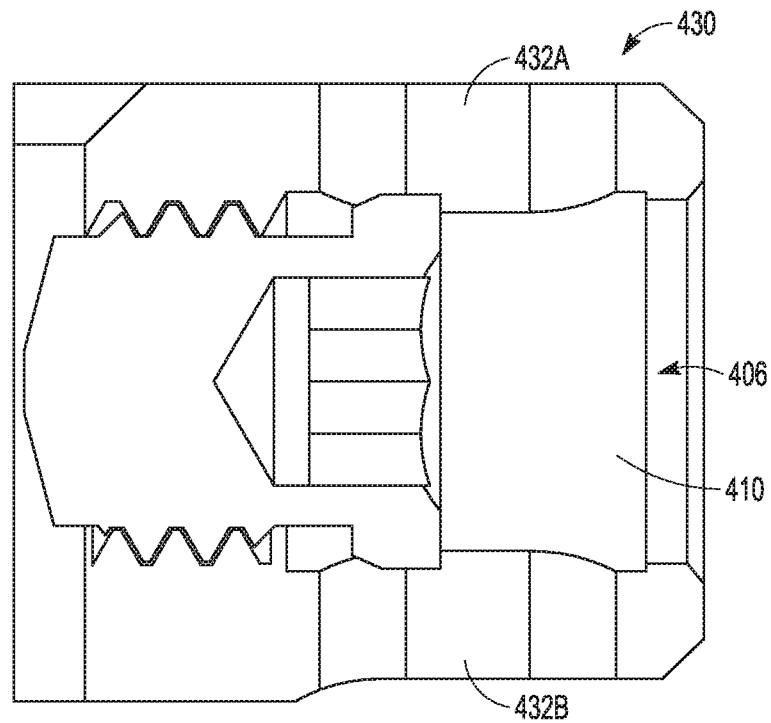

FIGS. 36A and 36B show an alternative assembly 430 of very similar construction to that of the assembly 400 of FIGS. 35A and 35B. Thus, the particular features of the assembly 430 will not be discussed in great detail as they include the features previously discussed in reference to FIGS. 35A and 35B. The example of FIGS. 36A and 36B differs from that of FIGS. 35A and 35B in that a passageway 432A and 432B is provided that communicates with the pocket portion 410. This passageway 432A and 432B can extend substantially transverse to the longitudinal axis of the bore 406, for example. The passageway 432A and 432B can facilitate the passage of sterilizing solution if desired.

Figure 37A:
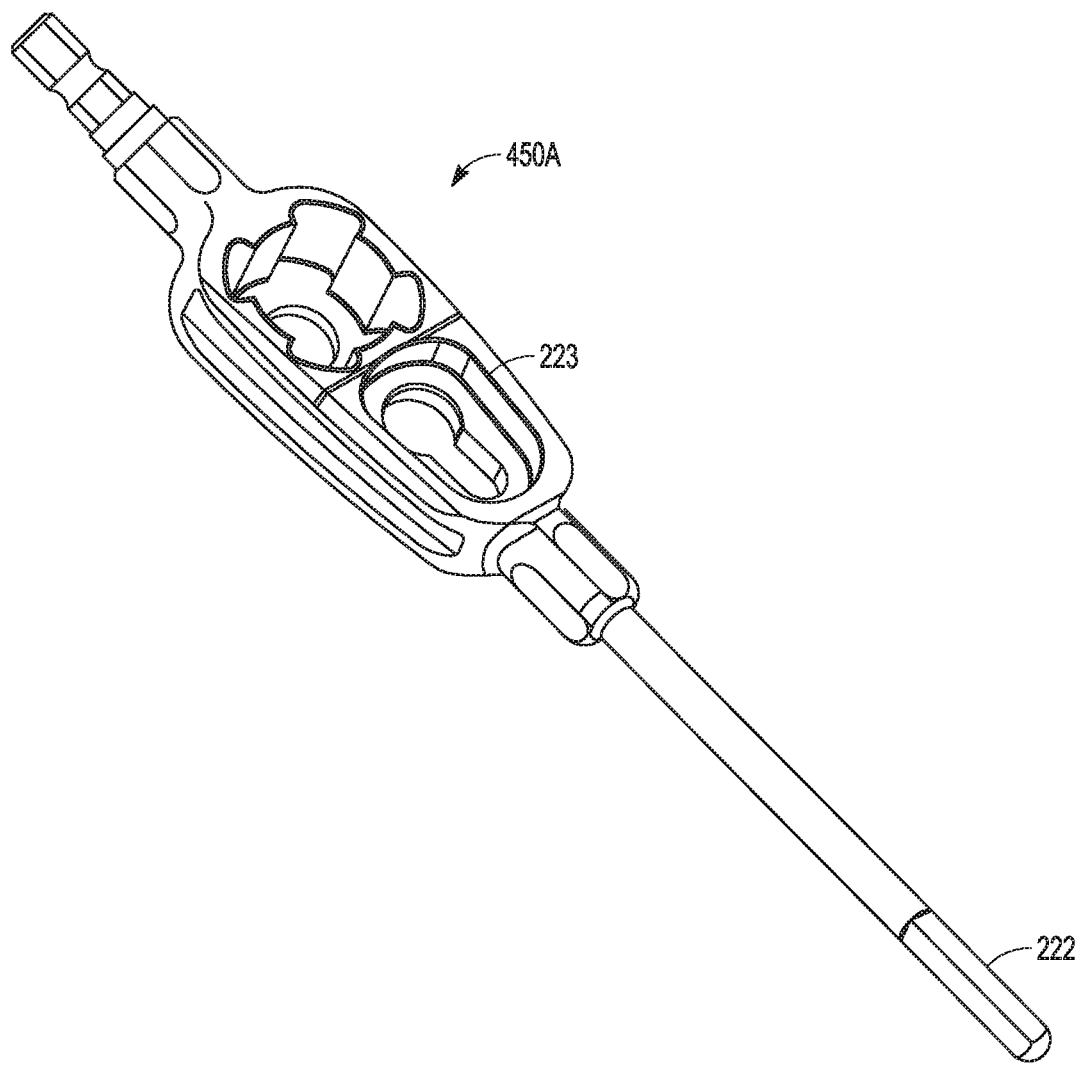
FIGS. 37A and 37B show two driver tools that can be used in alternative to the driver tool of FIG. 16 in accordance with an example of the present application.
Figure 37B:
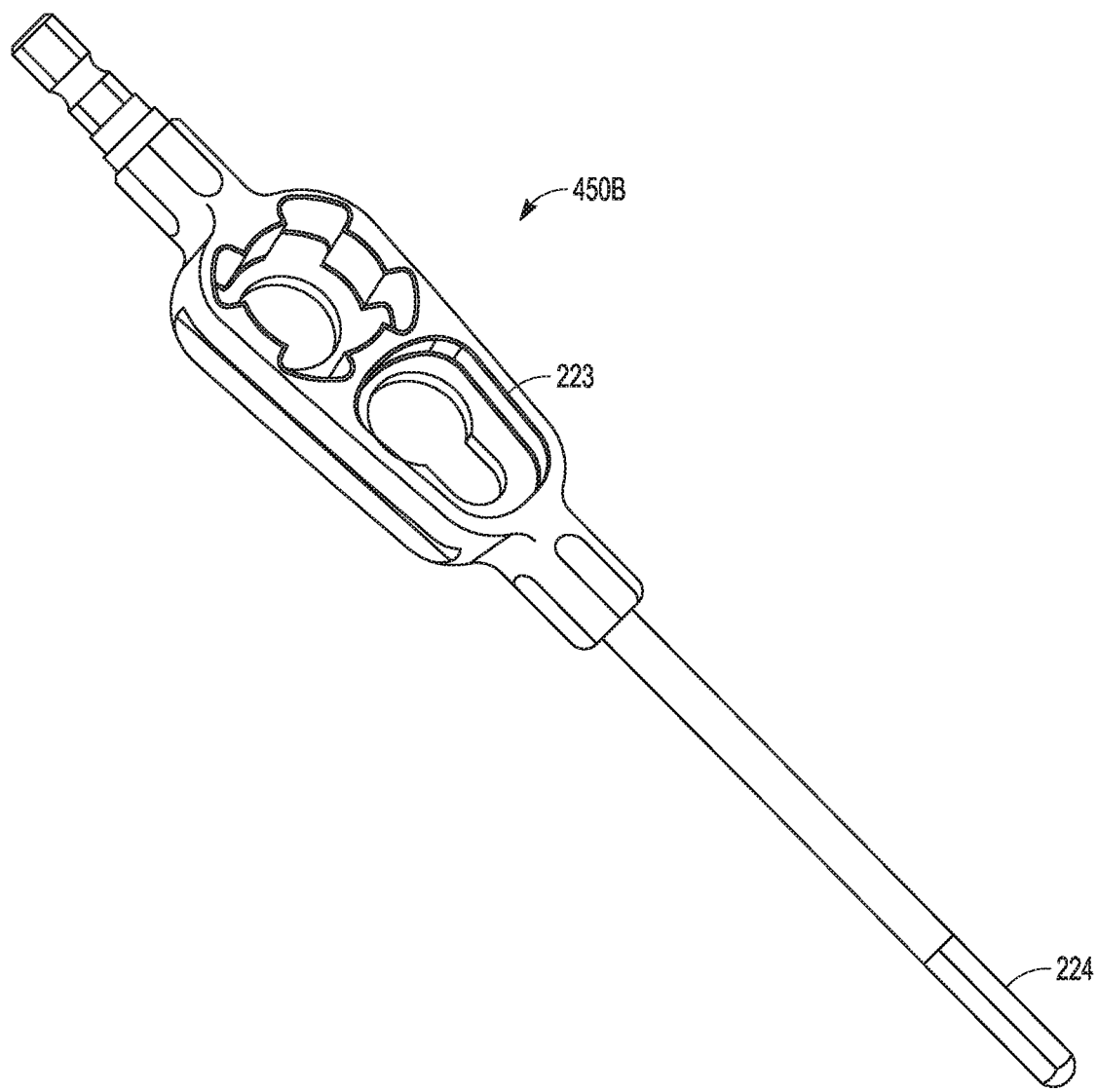

FIGS. 37A and 37B show two drivers 450A and 450B that can be utilized in alternative to driver 220 of FIG. 16. The driver 450A of FIG. 37A can be configured to engage with various components such as the assembly 210 (FIGS. 15 and 18) specifically, the fastener 214. Thus, the driver 450A can include the first head 222 and the handle 223 as previously described. The first head 222 of the driver 450A can be configured to couple with and engage the fastener 214 to actuate the fastener 214 to rotate and thread to engage with the adaptor 128 (e.g., FIGS. 11A-11E) to thread the fastener 214 with the adaptor 128 as shown in FIG. 17. According to the example of FIG. 37A the first head 222 can comprise a hex head with a 5 mm size.

The driver 450B of FIG. 37B can include the handle 223 and the second head 224. The driver 450B can be configured to engage with the stem provisional assembly 124 as previously shown and described in reference to FIGS. 11A-11E and 22A-22B. The second head 224 can be differently sized from the first head 222 (FIG. 37A). More particularly, the second head 224 can be smaller (e.g., a hex head of 3 mm size) than the first head 222 so as to configured to access portions of the adaptor 128 distal of those portions engaged by the first head 222 as was discussed and illustrated in reference to FIG. 19.

FIG. 38 shows a system 460 of monolithic components that can be assembled to comprise the stem provisional assembly for example. This system 460 can be used in alternatively to the modular system (separate adaptor and stem extension) of FIG. 24.

The system 460 can utilize monolithic versions of the stem provisional assembly (i.e. comprise a single component having one adaptor part 462A, 462B, 462C and one stem extension part 464A and 464B) as shown in FIG. 38.

At a base level, the system 460 can include a plurality of components 466, 468, 470, 472, 474 and 476. Each of the plurality of components 466, 468, 470, 472, 474 and 476 can have one of the plurality of adaptor parts 462A, 462B, 462C and one of the plurality of stem extension parts 464A and 464B.

The plurality of stem extension parts 464A and 464B can be configured to provide for different longitudinal length. For example, the stem extension part 464A can have 135 mm of longitudinal length and the stem extension part 464B can have 175 mm of longitudinal length. Various diameters for each of the plurality of stem extensions 464A and 464B can be provided as part of the system 460.

The plurality of adaptor parts 462B and 462C can be configured to provide different amounts of offset in the longitudinal direction. For example, the adaptor part 462B can provide for a first amount of offset O1. The adaptor part 462A can provide for substantially no offset. The third adaptor part 462C can provide for a third amount of offset O3 that can differ from the offset O1 and the no offset provided by the adaptor parts 462A and 462B. According to one example, the first amount of offset O1 comprises 3 mm and the offset O3 comprises 6 mm.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim.

Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A method for revision knee arthroplasty comprising:
shaping a bone of a patient to create one or more recesses therein;
selecting a stem provisional;
disposing the stem provisional within the one or more recesses; and
assembling in vivo the stem provisional with both a first provisional component configured to simulate a shape of one of a tibial tray implant or a femoral implant and a second provisional component configured to simulate a shape of at least one of a sleeve component, a cone component or a keel component of an implant; wherein the step of assembling includes:
engaging a fastener to thread the fastener into a threaded recess of the stem provisional; and
passing a tool through a passage in the fastener to engage the stem provisional distal of the threaded recess.

2. The method of claim 1, wherein prior to the assembling in vivo, the second provisional component and the stem provisional are initially coupled together via a handle configured to insert over a post extension prior to insertion into the patient, and further comprising:
inserting the stem provisional and the second provisional component together into the one or more recesses;
disengaging handle and the post extension from the second provisional component and the stem provisional; and
removing the handle and the post extension.

3. The method of claim 1, further comprising:
identifying an axis of the bone; and
determining if an offset construct for the stem provisional is desirable.

4. The method of claim 1, wherein selecting the stem provisional comprises:
selecting a monolithic stem provisional having an adaptor and a stem extension part; or
selecting the adaptor from a plurality of adaptors each of the plurality of adaptors having a longitudinal axis extending between a proximal end and a distal end, wherein the plurality of adaptors include at least a first adaptor with no offset of the longitudinal axis and at least a second adaptor with some amount of offset of the longitudinal axis; and
selecting the stem extension from a plurality of stem extensions each configured to couple with the plurality of adaptors, wherein the plurality of stem extensions each have a different longitudinal extent between a proximal end and a distal end.

5. The method of claim 1, further comprising rotating the stem provisional in vivo with the tool to position the first provisional component in a desired location on a resected surface of the bone.

6. The method of claim 1, further comprising removing at least the first provisional component, the second provisional component and the stem provisional together from the bone and the one or more recesses with the positions of each maintained relative to one another.

7. The method of claim 6, further comprising constructing an implant assembly based upon the positions of the first provisional component, the second provisional component and the stem provisional.

8. The method of claim 7, further comprising:
coupling a multi-purpose handle to one or more of the second provisional component and an offset broach; and
extracting the offset broach from the bone using movement of a slap hammer of the multi-purpose handle.

9. The method of claim 1, wherein shaping the bone of the patient to create one or more recesses therein comprises:
coupling a drill guide to the stem provisional, the drill guide having a plurality of apertures configured to receive and guide a drill into the bone; and
broaching the bone.

10. The method of claim 1, further comprising resecting the bone with a tibial cut guide assembly to form a resected surface, wherein resecting includes:
positioning a body of the tibial cut guide assembly adjacent a proximal portion of a tibia with a boom arm;
pinning the body to the proximal portion; and
removing the boom arm without removing the body from a position pinned to the proximal portion.

11. A method for revision knee arthroplasty comprising:
shaping a bone of a patient to create one or more recesses therein;
selecting a stem provisional;
disposing the stem provisional within the one or more recesses;
assembling in vivo the stem provisional with both a first provisional component configured to simulate a shape of one of a tibial tray implant or a femoral implant and a second provisional component configured to simulate a shape of at least one of a sleeve component, a cone component or a keel component of an implant
constructing an implant assembly based upon the positions of the first provisional component, the second provisional component and the stem provisional;
coupling a multi-purpose handle to one or more of the second provisional component and an offset broach; and
extracting the offset broach from the bone using movement of a slap hammer of the multi-purpose handle, wherein the offset broach has a cutting surface along only a first side thereof and a second side thereof opposing the first side is configured to receive and interface with a reamer, wherein the offset broach is configured to offset a first portion of the one or more recesses relative to a second portion of the one or more recesses.

12. A method for revision knee arthroplasty comprising:
shaping a bone of a patient to create one or more recesses therein;
selecting a stem provisional;
disposing the stem provisional within the one or more recesses; and
assembling in vivo the stem provisional with both a first provisional component configured to simulate a shape of one of a tibial tray implant or a femoral implant and a second provisional component configured to simulate a shape of at least one of a sleeve component, a cone component or a keel component of an implant, wherein shaping the bone of the patient to create one or more recesses therein comprises: performing a reaming of the bone with a tilt reamer having distal nose portion and a cutting portion with a back angled taper having a decreasing diameter as measured distal-to-proximal along a longitudinal axis of the tilt reamer.

* * * * *